United States Patent [19]

Froehler et al.

[11] Patent Number: 5,594,121
[45] Date of Patent: Jan. 14, 1997

[54] ENHANCED TRIPLE-HELIX AND DOUBLE-HELIX FORMATION WITH OLIGOMERS CONTAINING MODIFIED PURINES

[75] Inventors: Brian Froehler, Belmont; Mark Matteucci, Burlingame, both of Calif.

[73] Assignee: Gilead Sciences, Inc., Foster City, Calif.

[21] Appl. No.: 479,248

[22] Filed: Jun. 7, 1995

Related U.S. Application Data

[63] Continuation of Ser. No. 50,698, Apr. 19, 1993, abandoned, which is a continuation-in-part of Ser. No. 787,920, Nov. 7, 1991, abandoned.

[51] Int. Cl.$^6$ .......................... C07H 21/00; C07H 19/00; C07H 19/16; C12Q 1/68
[52] U.S. Cl. .................. 536/23.5; 536/23.1; 536/24.3; 536/24.5; 536/27.2; 536/27.6; 536/27.81; 435/6; 435/91.1
[58] Field of Search .................. 536/23.1, 24.1, 536/24.3, 25.3, 25.6, 24.5, 27.2, 27.21, 27.6, 27.7, 27.81; 519/44; 435/6, 91.2, 91.1

[56] References Cited

U.S. PATENT DOCUMENTS

| | | | |
|---|---|---|---|
| 3,309,358 | 3/1967 | Hanze | 536/25.6 |
| 3,337,530 | 8/1967 | Hanze | 536/25.6 |
| 3,962,211 | 6/1976 | Townsend et al. | 536/27.2 |
| 4,415,732 | 11/1983 | Caruthers et al. | 536/26.5 |
| 4,458,066 | 7/1984 | Caruthers et al. | 536/25.34 |
| 4,711,955 | 12/1987 | Ward et al. | 536/25.32 |
| 4,725,677 | 2/1988 | Köster et al. | 536/25.34 |
| 4,959,463 | 9/1990 | Froehler et al. | 536/25.3 |
| 5,053,499 | 10/1991 | Kojima et al. | 536/27.14 |
| 5,136,030 | 8/1992 | Chen | 536/27.11 |
| 5,264,564 | 11/1993 | Matteucci | 536/23.1 |
| 5,446,139 | 8/1995 | Seela et al. | 536/26.7 |
| 5,449,767 | 9/1995 | Ward et al. | 536/24.3 |
| 5,484,908 | 1/1996 | Froehler et al. | 536/24.31 |

FOREIGN PATENT DOCUMENTS

| | | |
|---|---|---|
| 1311201 | 12/1992 | Canada . |
| 0021293A3 | 1/1981 | European Pat. Off. . |
| 0057548A3 | 8/1982 | European Pat. Off. . |
| 0251786A3 | 1/1988 | European Pat. Off. . |
| 0286028A2 | 10/1988 | European Pat. Off. . |
| 375408 | 6/1990 | European Pat. Off. . |
| 0450102A1 | 10/1991 | European Pat. Off. . |
| WO89/12060 | 12/1989 | WIPO . |
| WO89/12380 | 12/1989 | WIPO . |
| WO90/03370 | 4/1990 | WIPO . |
| 90/06934 | 6/1990 | WIPO . |
| 92/10590 | 6/1992 | WIPO . |
| WO93/03736 | 3/1993 | WIPO . |
| WO93/09127 | 5/1993 | WIPO . |
| 93/12130 | 6/1993 | WIPO . |

OTHER PUBLICATIONS

Cocuzza, Anthony J., "Total Synthesis of 7–IODO–2', 3'–Dideoxy–7–Deazapurine Nucleosides, Key Intermediates In the Preparation of Reagents for the Automated Sequencing of DNA," Tet Lett 29(33):4061–4064 (1988).

Cottam et al., "Synthesis and Biological Activity of Certain 6–Substituted and 2,6–Disubstituted 2'–Deoxytubercidins Prepared via the Sterospecific Sodium Salt Glycosylation Procedure," J Med Chem 28:1461–1467 (1985).

Secrist III, et al., "Studies Directed toward a Total Synthesis of Nucleoside Q. The Annulation of 2,6–Diaminopyrimidin–4–one with alpha–Halo Carbonyls to Form Pyrrolo[2,3–d]pyrimidines and Furo[2,3–d]pyrimidines," J Org Chem 43(20):3937–3941 (1978).

Crisp et al, "Synthesis of 5–aryluridines and 5–Aryl–2'–deoxyuridines," Synthetic Comm 20(3):413–422 (1990).

Ikehara et al, "Polynucleotides. III. Synthesis of Four Trinucleoside Diphosphates containing Tubercidin (7–Deazaadenosin) and N6–Dimethyladenosine," Chem Pharm Bull 14:1338–1346 (1966).

Seela et al, "Alternating d(G–C)3 and d(C–G)3 hexanucleotides containing 7–deaza–2'–deoxyguanosine or 8–aza–7–deaza–2'–deoxyguanosine in place of dG," Nuc Acids Res 17(3):901–910 (1989).

Seela et al, "Poly(7–deazaguanylic acid), the Homopolynucleotide of the Parent Nucleoside of Queuosine," Biochem 21:4338–4343 (1982).

Seela et al, "Poly(adenylic acids) containing the antibiotic tubercidin–base pairing and hydrolysis by nuclease S1," Nuc Acids Res 10(4):1389–1397 (1982).

Collier et al, "Site–Specific Intercalation at the Triplex–Duplex Junction Induces a Conformational Change Which is Detectable by Hypersensitivity to Diethylpyrocarbonate," Nuc Acids Res 19(15):4219–4224 (1991).

Wagner et al, "Antisense Gene Inhibition by Oligonucleotides Containing C–5 Propyne Pyrimidines," Science 160:1510–1513 (1993).

Maher, et al., "Inhibition of DNA Binding Proteins by Oligonucleotide–Directed Triple Helix Formation," Science (1989) 245:725–730.

(List continued on next page.)

Primary Examiner—John L. Leguyader
Assistant Examiner—Thomas G. Larson
Attorney, Agent, or Firm—Daryl D. Muenchau

[57] ABSTRACT

Novel oligomers are disclosed which have enhanced ability with respect to forming duplexes or triplexes compared with oligomers containing only conventional bases. The oligomers contain 7-deaza-7-substituted purines or related analogs. The oligomers of the invention are capable of (i) forming triplexes with various target sequences such as virus or oncogene sequences by coupling into the major groove of a target DNA duplex at physiological pH or (ii) forming duplexes by binding to single-stranded DNA or to RNA encoded by target genes. The oligomers of the invention can be constructed to have any desired sequence, provided the sequence normally includes one or more bases that is replaced with the analogs of the invention. Compositions of the invention can be used for diagnostic purposes in order to detect viruses or disease conditions.

58 Claims, 29 Drawing Sheets

OTHER PUBLICATIONS

Moser and Dervan, "Sequence–specific Cleavage of Double Helical DNA by Triple Helix Formation," *Science* (1987) 238:645–650.

Cooney et al., "Site–Specific Oligonucleotide Binding Represses Transcription of the Human c–myc Gene In Vitro," *Science* (1988) 241:456–459.

Beal and Dervan, "Second Structural Motif for Recognition of DNA by Oligonucleotide–Directed Triple–Helix Formation,"*Science* (1990) 251:1360–1363.

Griffin and Dervan, "Recognition of Thymine–Adenine Base Pairs by Guanine in a Pyrimidine Triple Helix Motif," *Science* (1989) 245:967–971.

Postel et al., "Evidence that a Triple–Forming Oligodeoxyribonucleotide Binds to the c–myc Promoter in HeLa Cells, Thereby Reducing c–myc mRNA Levels," *Proc. Natl. Acad. Sci.* (USA) (1991) 88:8227–8231.

Durland et al., "Binding of Triple Helix Forming Oligonucleotides to Sites in Gene Promoters," *Biochemistry* (1991) 38:9246–9255.

Williamson et al., "Monovalent Cation–Induced Structure of Telomeric DNA: The G–Quartet Model," *Cell* (1989) 59:871–880.

Seela et al., "7–Deaza–Isostere non 2'–Deoxyxanthosin and 2'–Desoxyspongosin–Synthase via Glycosylieiring von 2,4–Dichlor–7H–pyrrolo[2,3–d] pyrimidin," *Liebigs Ann Der Chemie* (1985) pp. 312–320 (translation unavailable).

Praseuth et al., "Sequence–specific Binding and Photocrosslinking of α and β Polydeoxynucleotides to the Major Groove of DNA via Triple–Helix Formation," *Proc. Natl. Acad. Sci.* (USA) (1988) 85:1349–1353.

Vlassov et al.,"Sequence Specific Chemical Modification of Double–stranded DNA with Alkylating Oligodeoxy Nucleotide Derivatives," *Gene* (1988) 313–322.

Fedorova et al., "Complementary Addressed Modification of Double–stranded DNA within a Ternary Complex," *FEBS* (1988) 288:273–276.

Capobionco et al., "One Pot Solution Synthesis of Cyclic Oligodeoxyribonucleotides," *Nucleic Acids Res.* (1990) 18:2661–2669.

van de Sande et al., "Parallel Stranded DNA," *Science* (1988) 241:551–557; and.

Horn and Dervan, "Recognition of Mixed–Sequence Duplex DNA by Alternate–Strand Triple–Helix Formation," *J. Am. Chem. Soc.* (1990) 112:2435–2437.

Winkler et al. (1984) "Synthesis and Furanoside/Pyranoside Isomerization of 7–deaza–2'–deoxy–7–methylguanosim Liebigs," *Annals of Chemistry* 4 (1984) abstract.

Krawczyk et al., "Oligonucleotide–Mediated Triple Helix Formation Using an N3–protonated Deoxycytidine Analog Exhibiting pH–independent Binding within the Physiological Range," *PNAS* (1992) 89:3761–3763.

Kawasaki et al., "Uniformly Modified 2'–Deoxy–2'–fluoro Phosphorothioate Oligonucleotides as Nuclease–Resistant Antisense Compounds with High Affinity and Specificity for RNA Targets," *J. Med. Chem.*, 36:831–841 (1993).

Uhlman et al., "Antisense Oligonucleotides: A New Therapeutic Principle," *Chem. Reviews* (1990) 90:543–584.

Van der Krol et al., "Modulation of Eukaryotic Gene Expression by Complementary RNA or DNA Sequences," *Biotechniques* (1988) 6:958–976.

Vlassov et al., "Complementary addressed modification and cleavage of a single stranded DNA fragment with alkylating oligonucleotide derivatives," *Nucleic Acids Res.* (1986) 14:4065–4076.

Knorre et al., "Reactive oligonucleotide derivatives and sequence–specific modification of nucleic acids," *Biochemie* (1985) 67:785–789.

Iverson et al., "Nonenzymatic Sequence–Specific Cleavage of Single–Stranded DNA to Nucleotide Resolution. DNA Methyl Thioether Probes," *J. Am. Chem. Soc.* (1987) 109:1241–1243.

Meyer, Jr. et al., "Efficient Specific Cross–Linking and Cleavage of DNA by Staple, Synthetic Complementary Oligonucleotides," *J. Am. Chem. Soc.* (1989) 111:8517–8519.

Lee et al., "Interaction of Psoralen–Derivatized Oligodeoxyribonucleoside Methylphosphonates with Single–Stranded DNA," *Biochemistry* (1988) 27:3197–3203.

Webb et al., "Sequence–Specific Cross–linking of Deoxyoligonucleotides via Hybridization–Triggered Alkyation," *J. Am. Chem. Soc.* (1986) 108:2764–2765.

Webb et al., "Hybridization triggered cross–linking of deoxyoligonucleotides," *Nucleic Acids Res.* (1986) 14:7661–7674.

Shaw et al., "Specific High–Efficiency, Triple–Helix–Mediated Cross–Linking to Duplex DNA," *J. Am. Chem. Soc.* (1991) 113:7765–7766.

Matteucci et al., "Synthesis and Crosslinking Properties of a Deoxyoligonucleotide Containing $N^6,N^6$–ethanodeoxyadenosine," *Tetrahedron Letters* (1987) 28:2469–2472.

Froehler et al., "Triple–Helix Formation and Cooperative Binding by Oligodeoxynucleotides with a 3'–3' Internucleotide Junction," *Biochemistry* (1992) 31:1603–1609.

Young et al., "Triple helix formation inhibits transcription elongation in vitro," *PNAS* (1991) 88:10023–10026.

Froehler et al., "Oligodeoxynucleotides Containing C–5 Propyne Analogs of 2'–Deoxyuridine and 2'–Deoxycytidine," *Tetrahedron Letters* (1992) 33:5307–5310.

Froehler et al., "Oligonucleotides Derived from 5–(1–Propenyl)–2'–O–Allyl–Uridine and 5–(1–Propenyl)–2'–O–Allyl–Cytidine: Synthesis and RNA Duplex Formation," *Tetrahedron Letters* (1993) 34(6):1003–1006.

Seela et al., "Palindromic Octa– and Dodecanucleotides Containing 2'–Deoxytubercidin: Synthesis, Hairpin Formation, and Recognition by the Endodeoxyribonuclease EcoRI," *Biochemistry* (1987) 26:2232–2238.

Seela et al., "Palindromic oligonucleotides 7–deaza–2'–deoxyguanosine: solid–phase synthesis of d[(p)GG*AATTCC] octamers and recognition by the endodeoxyribonuclease ECoRI," Nucleic Acids Res. (1986) 14:2319–2332.

Seela et al., "Oligomers with Alternating Thymidine and 2'–Deoxytubercidin: Duplex Stabilization by a 7–Deazapurine Base," *Biochemistry* (1985) 24:7556–7561.

Prober et al., "A System for Rapid DNA Sequencing with Fluorescent Chain–Terminating Dideoxynucleotides," *Science* (1987) 238:336–341.

Arcadi et al., "Palladium–Catalysed Coupling of Aryl and Vinyl Triflates or Halides with 2–Ethynylaniline; An Efficient Route to Functionalized 2–Substituted Indoles," *Tetrahedron Letters*, 30(19):2581–2584 (1989).

Badone et al., "Palladium–Catalyzed Coupling of Aryl Arenesulfonates with Organostannanes," *J. Org. Chem.*, 57:6321–6323 (1992).

Bergstrom et al., "Pyrrol[2,3–d]pyrimidine Nucleoside Antibiotic Analogues. Synthesis via Organopalladium Intermediates Derived from 5–Mercuritubercidin," *J. Org. Chem.*, 46:1423–1431 (1981).

Crisp et al., "Synthesis of 5–aryluridines and 5–Aryl–2'–deoxyuridines," *Synthetic Communications*, 10(3):413–422 (1990).

Edstrom et al., "Synthesis of a Novel Pyrrolo[2,3–d]pyrimidine Alkaloid, Rigidin," *J. Org. Chem.*, 58:403–407 (1993).

Farina et al., "Palladium–catalyzed Approach to 5–substituted Uracil and Uridine Derivatives," *Synlett*, pp. 157–159 (Mar. 1991).

Iritani et al., "Palladium Catalyzed Reaction of 2–alkynylanilines with Allyl Chlorides, Formation of 3–allylindoles," *Tetrahedron Letters*, 29(15):1799–1802 (1988).

Larock et al., "Synthesis of Indoles via Palladium–catalyzed Heteroannulation of Internal Alkynes," *J. Org. Chem.*, 113:6689–6690 (1991).

Malm et al., "Palladium–catalyzed Coupling of Heteroaryl Alkylstannanes with Heteroaryl Halides in the Presence of Silver(I)oxide," *Tetrahedron Letters*, 33(16):2199–2202 (1992).

Milligan et al., "An Anti–parallel Triple Helix Motif with Oligondeoxynucleotides Containing 2'–deoxyguanosine and 7–deaza–2'–deoxyanthosine," *Nucleic Acids Res.*, 21(2):327–333 (1993).

Muchowski et al., "Ortho Functionalization of N–(tert–Butoxycarbonyl)aniline," *J. Am. Chem. soc.*, 45:4798–4801 (1980).

Rudisill et al., "Palladium–Catalyzed Synthesis of 2–Substituted Indoles," *J. Org. Chem.*, 54:5856–5866 (1989).

Salituro et al., "Facile Synthesis of L–Kynurenine," *J. Org. Chem.*, 53:6138–6139 (1988).

Scott et al., "Palladium–Catalyzed Coupling of vinyl Triflates with Organostannanes. Synthetic and Mechanistic Studies," *J. Am. Chem. Soc.*, 108:3033–3040 (1986).

Turner, J. A., "Regiospecific Electrophilic Substitution of Aminopyridines: Ortho Lithiation of 2–,3–and 4– Pivaloylamino)pyridines," *J. Org. Chem.*, 48:3401–3408 (1983).

X = O, S
$X^2$ = CO, CS or $SO_2$
$X^3$ = O, S, $CH_2$, $CF_2$, CFH, NH, $NCH_3$ (8)

(9)

(10)

(11)

(12)

(13)

(14)

(15)

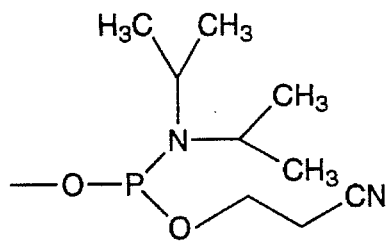
N,N-diisopropylamino-β-cyanoethoxyphosphine
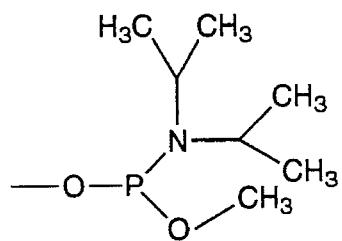
N,N-diisopropylamino-methoxyphosphine
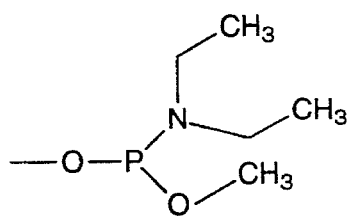
N,N-diethylamino-methoxyphosphine
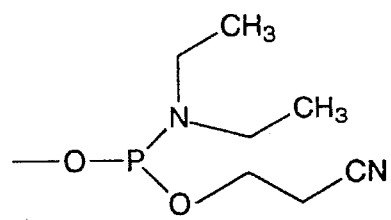
N,N-diethylamino-β-cyanoethoxy phosphine
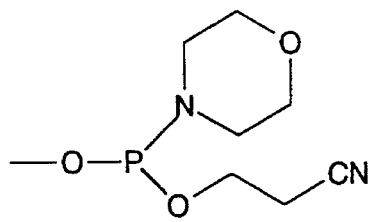
N-morpholino-β-cyanoethoxyphosphine
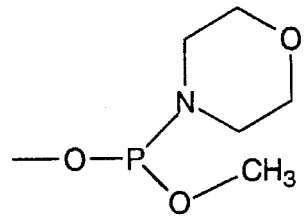
N-morpholino methoxyphosphine
Figure 10-1

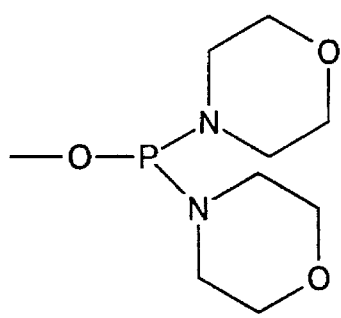
Bis morpholino-phosphine
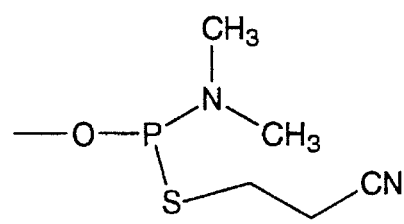
N,N-dimethylamino-
β-cyanoethylmercapto-phosphine
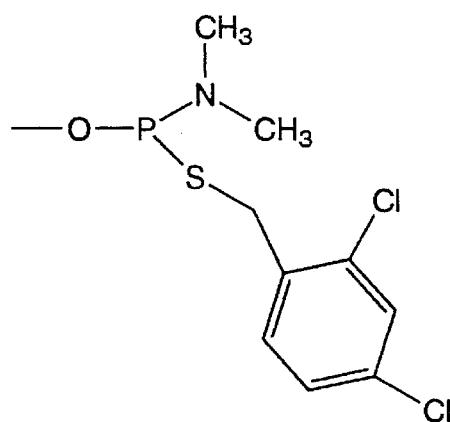
N,N-dimethylamino-
2,4-dichlorobenzylmercapto-
phosphine
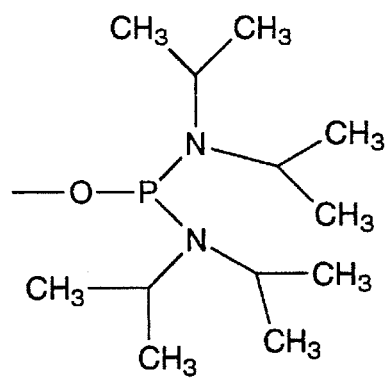
Bis(N,N-diisopropylamino)-
phosphine
Figure 10-2

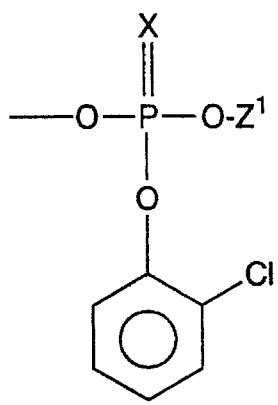
2-chlorophenyl phosphate
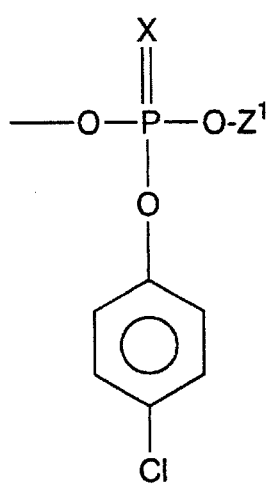
4-chlorophenyl phosphate
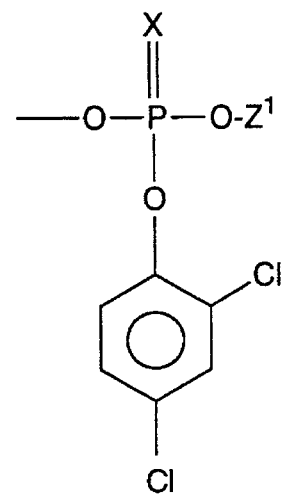
2,4-dichlorophenyl phosphate
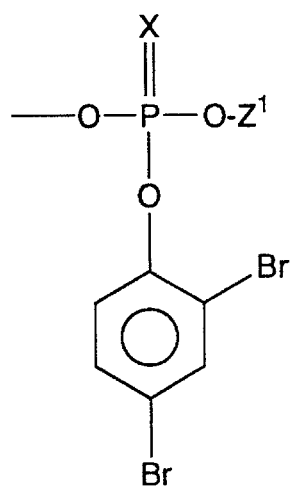
2,4-dibromophenyl phosphate
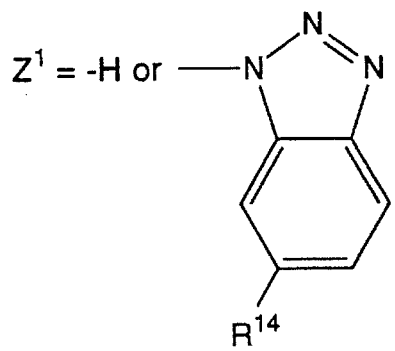
X = O or S
$R^{14}$ = H, $NO_2$ and $CF_3$
Figure 10-3

N,N-diisopropylamino-methyl-
phosphine

N,N-diethylamino-methyl-
phosphine

R[13] = aryl, alkyl or O-tBu $Q = CR^{11}$, or N

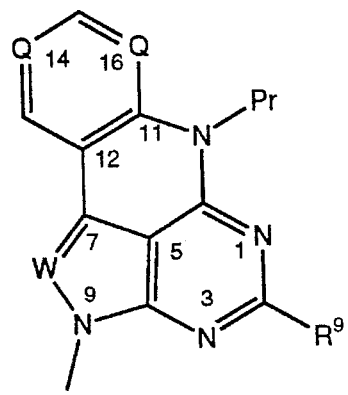
(23)
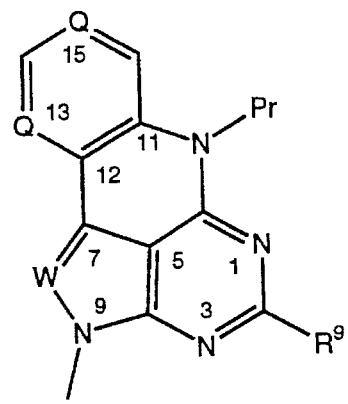
(25)
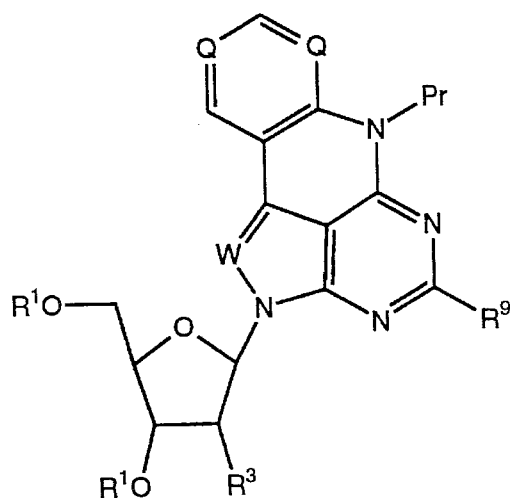
(24)
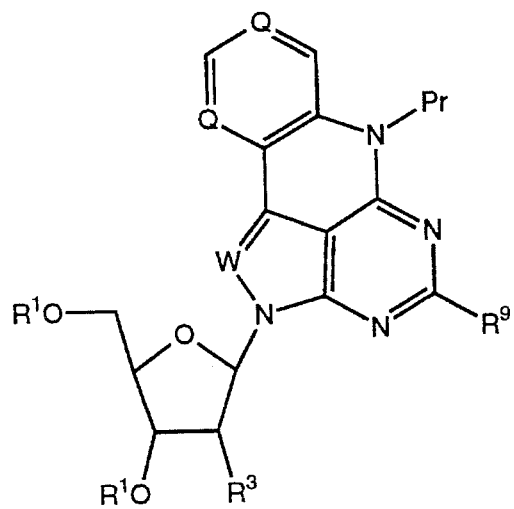
(26)
Q = $CR^{11}$, or N
Figure 16-2

$R^{16} = H, CH_3$

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:1:

AGGAGAAGGA GGAGG                                          15

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:2:

CCTCCTCCTT CTCCT                                          15

( 2 ) INFORMATION FOR SEQ ID NO:3:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(16, "")
        ( D ) OTHER INFORMATION: /note="This position is
            anthraquinone."

( x i ) SEQUENCE DESCRIPTION: SEQ ID NO:3:

GGTGGTGGTT GTGGTY                                       16

( 2 ) INFORMATION FOR SEQ ID NO:4:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(16, "")
        ( D ) OTHER INFORMATION: /note="This position is
            anthraquinone."

( x i ) SEQUENCE DESCRIPTION: SEQ ID NO:4:

GGNGGNGGNN GNGGNY                                       16

( 2 ) INFORMATION FOR SEQ ID NO:5:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
    ( A ) NAME/KEY: misc_feature
    ( B ) LOCATION: (1^2)
    ( D ) OTHER INFORMATION: /note="This position is
        2'-deoxy-7- deazaxanthosine residue."

( i x ) FEATURE:
    ( A ) NAME/KEY: misc_feature
    ( B ) LOCATION: (2^3)
    ( D ) OTHER INFORMATION: /note="This position is
        2'-deoxy-7- deazaxanthosine residue."

( i x ) FEATURE:
    ( A ) NAME/KEY: misc_feature
    ( B ) LOCATION: (4^5)
    ( D ) OTHER INFORMATION: /note="This position is
        2'-deoxy-7- deazaxanthosine residue."

( i x ) FEATURE:
    ( A ) NAME/KEY: misc_feature
    ( B ) LOCATION: (5^6)
    ( D ) OTHER INFORMATION: /note="This position is
        2'-deoxy-7- deazaxanthosine residue."

( i x ) FEATURE:
    ( A ) NAME/KEY: misc_feature
    ( B ) LOCATION: (7^8)
    ( D ) OTHER INFORMATION: /note="This position is
        2'-deoxy-7- deazaxanthosine residue."

( i x ) FEATURE:
    ( A ) NAME/KEY: misc_feature
    ( B ) LOCATION: (8^9)
    ( D ) OTHER INFORMATION: /note="This position is
        2'-deoxy-7- deazaxanthosine residue."

( i x ) FEATURE:
    ( A ) NAME/KEY: misc_feature
    ( B ) LOCATION: (11^12)
    ( D ) OTHER INFORMATION: /note="This position is
        2'-deoxy-7- deazaxanthosine residue."

( i x ) FEATURE:
    ( A ) NAME/KEY: misc_feature
    ( B ) LOCATION: (13^14)
    ( D ) OTHER INFORMATION: /note="This position is
        2'-deoxy-7- deazaxanthosine residue."

( i x ) FEATURE:
    ( A ) NAME/KEY: misc_feature
    ( B ) LOCATION: (14^15)
    ( D ) OTHER INFORMATION: /note="This position is
        2'-deoxy-7- deazaxanthosine residue."

( x i ) SEQUENCE DESCRIPTION: SEQ ID NO:5:

GGTGGTGGTT GTGGT                                                    15

( 2 ) INFORMATION FOR SEQ ID NO:6:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: one-of(1, 3, 5, 7, 10)
        ( D ) OTHER INFORMATION: /note="These positions are
            2'- deoxyadenosine."

( x i ) SEQUENCE DESCRIPTION: SEQ ID NO:6:

ATATATATTA TTTTT                                                    15

( 2 ) INFORMATION FOR SEQ ID NO:7:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i x ) FEATURE:
    ( A ) NAME/KEY: misc_difference
    ( B ) LOCATION: one-of(6, 9, 11, 13, 15)
    ( D ) OTHER INFORMATION: /note="These positions are T,
        5-(1- propynyl)-2'-deoxyruidine (pdU), or other suitable
        pyrimidines."

( i x ) FEATURE:
    ( A ) NAME/KEY: misc_difference
    ( B ) LOCATION: replace(1..4, "")
    ( D ) OTHER INFORMATION: /note="These positions are
        7- substituted deazapurine nucleomonomers."

( i x ) FEATURE:
    ( A ) NAME/KEY: misc_difference
    ( B ) LOCATION: one-of(5, 7, 8, 10, 12, 14)
    ( D ) OTHER INFORMATION: /note="These positions are
        2'- deoxyadenosine."

( x i ) SEQUENCE DESCRIPTION: SEQ ID NO:7:

NNNNAUAAUA UAUAU                                                               15

( 2 ) INFORMATION FOR SEQ ID NO:8:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i x ) FEATURE:
    ( A ) NAME/KEY: misc_difference
    ( B ) LOCATION: one-of(6, 9, 11, 13, 15)
    ( D ) OTHER INFORMATION: /note="These positions are T,
        5-(1- propynyl)-2'-deoxyruidine (pdU), or other suitable
        pyrimidines."

( i x ) FEATURE:
    ( A ) NAME/KEY: misc_difference
    ( B ) LOCATION: replace(7, "")
    ( D ) OTHER INFORMATION: /note="This position is
        7- substituted deazapurine nucleomonomer."

( i x ) FEATURE:
    ( A ) NAME/KEY: misc_difference
    ( B ) LOCATION: one-of(1, 2, 3, 4, 5, 8, 10, 12, 14)
    ( D ) OTHER INFORMATION: /note="These positions are
        2'- deoxyadenosine."

( x i ) SEQUENCE DESCRIPTION: SEQ ID NO:8:

AAAAAUNAUA UAUAU                                                              15

( 2 ) INFORMATION FOR SEQ ID NO:9:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i x ) FEATURE:
    ( A ) NAME/KEY: misc_difference
    ( B ) LOCATION: one-of(6, 9, 11, 13, 15)
    ( D ) OTHER INFORMATION: /note="These positions are T,
        5-(1- propynyl)-2'-deoxyruidine (pdU), or other suitable
        pyrimidines."

( i x ) FEATURE:
    ( A ) NAME/KEY: misc_difference
    ( B ) LOCATION: replace(8, "")

(D) OTHER INFORMATION: /note="This position is
7- substituted deazapurine nucleomonomer."

(ix) FEATURE:
 (A) NAME/KEY: misc_difference
 (B) LOCATION: one-of(1, 2, 3, 4, 5, 7, 10, 12, 14)
 (D) OTHER INFORMATION: /note="These positions are
  2'- deoxyadenosine."

(xi) SEQUENCE DESCRIPTION: SEQ ID NO:9:

AAAAAUANUA UAUAU    15

(2) INFORMATION FOR SEQ ID NO:10:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (ix) FEATURE:
  (A) NAME/KEY: misc_difference
  (B) LOCATION: one-of(6, 9, 11, 13, 15)
  (D) OTHER INFORMATION: /note="These positions are T,
   5-(1- propynyl)-2'-deoxyruidine (pdU), or other suitable
   pyrimidines."

(ix) FEATURE:
  (A) NAME/KEY: misc_difference
  (B) LOCATION: replace(10, "")
  (D) OTHER INFORMATION: /note="This position is
   7- substituted deazapurine nucleomonomer."

(ix) FEATURE:
  (A) NAME/KEY: misc_difference
  (B) LOCATION: one-of(1, 2, 3, 4, 5, 7, 8, 12, 14)
  (D) OTHER INFORMATION: /note="These positions are
   2'- deoxyadenosine."

(xi) SEQUENCE DESCRIPTION: SEQ ID NO:10:

AAAAAUAAUN UAUAU    15

(2) INFORMATION FOR SEQ ID NO:11:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (ix) FEATURE:
  (A) NAME/KEY: misc_difference
  (B) LOCATION: one-of(6, 9, 11, 13, 15)
  (D) OTHER INFORMATION: /note="This position is T,
   5-(1- propynyl)-2'-deoxyruidine (pdU), or other suitable
   pyrimidines."

(ix) FEATURE:
  (A) NAME/KEY: misc_difference
  (B) LOCATION: one-of(8, 10, 12, 14)
  (D) OTHER INFORMATION: /note="These positions are
   7- substituted deazapurine nucleomonomers."

(ix) FEATURE:
  (A) NAME/KEY: misc_difference
  (B) LOCATION: one-of(1, 2, 3, 4, 5, 7)
  (D) OTHER INFORMATION: /note="These positions are
   2'- deoxyadenosine."

(xi) SEQUENCE DESCRIPTION: SEQ ID NO:11:

AAAAAUANUN UNUNU    15

(2) INFORMATION FOR SEQ ID NO:12:

```
( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: one-of(6, 9, 11, 13, 15)
        ( D ) OTHER INFORMATION: /note="This position is T,
                5-(1- propynyl)-2'-deoxyruidine (pdU), or other suitable
                pyrimidines."

( i x ) FEATURE:
        ( A ) NAME/KEY: misc_difference
        ( B ) LOCATION: one-of(1, 2, 3, 4, 5, 7, 8, 10, 12, 14)
        ( D ) OTHER INFORMATION: /note="These positions are
                2'- deoxyadenosine."

( x i ) SEQUENCE DESCRIPTION: SEQ ID NO:12:

AAAAAUAAUA  UAUAU                                                          1 5
```

ENHANCED TRIPLE-HELIX AND DOUBLE-HELIX FORMATION WITH OLIGOMERS CONTAINING MODIFIED PURINES

This is a continuation of application Ser. No. 08/050,698 filed on Apr. 19, 1993, abandoned, which is a continuation-in-part of U.S. patent application Ser. No. 07/787,920, filed Nov. 7, 1991, now abandoned.

TECHNICAL FIELD

The invention relates generally to novel nucleomonomer and oligomer analogs, and to oligonucleotide-based diagnosis by binding of the oligonucleotide analogs to single or double-stranded nucleic acid target sequences. More specifically, the invention concerns oligomers containing certain 7-substituted deazapurine base residues and intermediates in their synthesis.

BACKGROUND ART

Sequence-specific binding of oligonucleotides both to single-stranded RNA and DNA and to duplex DNA has been demonstrated. The appropriate sequence recognition for binding to single-stranded targets is well known: the A-T and G-C pairing characteristic of duplex formation has been established as the basis for DNA replication and transcription.

More recently, oligonucleotides have been shown to bind in a sequence-specific manner to duplex DNA to form triplexes. Single-stranded nucleic acid, primarily RNA, is the target molecule for oligonucleotides that are used to inhibit gene expression by an "antisense" mechanism (Uhlmann, E., et al., *Chem Reviews* (1990) 90:543–584; van der Krol, A. R., et al., *Biotechniques* (1988) 6:958–976). Antisense oligonucleotides are postulated to exert an effect on target gene expression by hybridizing with a complementary RNA sequence. In this model, the hybrid RNA-oligonucleotide duplex interferes with one or more aspects of RNA metabolism including processing, translation and metabolic turnover. Chemically modified oligonucleotides have been used to enhance their nuclease stability.

Duplex DNA can be specifically recognized by oligomers based on a recognizable nucleomonomer sequence. The motif termed "GT" recognition has been described (Beal, P. A., et al., *Science* (1992) 251:1360–1363; Cooney, M., et al., *Science* (1988) 241:456–459; Hogan, M. E., et al., EP Publication 375408). In the G-T motif, the oligonucleotide is oriented antiparallel to the target purine-rich sequence and A-T pairs are recognized by adenine or thymine residues and G-C pairs by guanine residues.

Sequence-specific targeting of both single-stranded and duplex target sequences has applications in diagnosis, analysis, and therapy. Under some circumstances wherein such binding is to be effected, it is advantageous to stabilize the resulting duplex or triplex over long time periods.

Covalent crosslinking of the oligomer to the target provides one approach to prolong stabilization. Sequence-specific recognition of single-stranded DNA accompanied by covalent crosslinking has been reported by several groups. For example, Vlassov, V. V., et al., *Nucleic Acids Res* (1986) 14:4065–4076, describe covalent bonding of a single-stranded DNA fragment with alkylating derivatives of nucleomonomers complementary to target sequences. A report of similar work by the same group is that by Knorre, D. G., et al., *Biochimie* (1985) 67:785–789. Iverson and Dervan also showed sequence-specific cleavage of single-stranded DNA mediated by incorporation of a modified nucleomonomer which was capable of activating cleavage (*J Am Chem Soc* (1987) 109:1241–1243). Meyer, R. B., et al., *J Am Chem Soc* (1989) 111:8517–8519, effect covalent crosslinking to a target nucleomonomer using an alkylating agent complementary to the single-stranded target nucleomonomer sequence. Photoactivated crosslinking to single-stranded oligonucleotides mediated by psoralen was disclosed by Lee, B. L., et al., *Biochemistry* (1988) 27:3197–3203. Use of crosslinking in triple-helix forming probes was also disclosed by Horne, et al., *J Am Chem Soc* (1990) 112:2435–2437.

Use of $N^4,N^4$-ethanocytosine as an alkylating agent to crosslink to single-stranded and double-stranded oligomers has also been described (Webb and Matteucci, *J. Am Chem Soc* (1986) 108:2764–2765; *Nucleic Acids Res* (1986) 14:7661–7674; Shaw, J. P., et al., *J Am Chem Soc* (1991) 113:7765–7766). These papers also describe the synthesis of oligonucleotides containing the derivatized cytosine. Matteucci and Webb, in a later article in *Tetrahedron Letters* (1987) 28:2469–2472, describe the synthesis of oligomers containing $N^6,N^6$-ethanoadenine and the crosslinking properties of this residue in the context of an oligonucleotide binding to a single-stranded DNA. Praseuth, D., et al., *Proc Natl Acad Sci (USA)* (1988) 85:1349–1353, described sequence-specific binding of an octathymidylate conjugated to a photoactivatable crosslinking agent to both single-stranded and double-stranded DNA.

In addition, Vlassov, V. V. et al., *Gene* (1988) 313–322 and Fedorova, O. S. et al., *FEBS* (1988) 228:273–276, describe targeting duplex DNA with an alkylating agent linked through a 5'-phosphate of an oligonucleotide.

In effecting binding to obtain a triplex, to provide for instances wherein purine residues are concentrated on one chain of the target and then on the opposite chain, oligomers of inverted polarity can be provided. By "inverted polarity" is meant that the oligomer contains tandem sequences which have opposite polarity, i.e., one segment or region of sequences having polarity 5'→3' followed by another with polarity 3'→5', or vice versa. This implies that these sequences are joined by linkages which can be thought of as effectively a 3'-3' internucleoside junction (however the linkage is accomplished), or effectively a 5'-5' internucleoside junction. Such oligomers have been suggested as by-products of reactions to obtain cyclic oligonucleotides by Capobionco, M. L., et al., *Nucleic Acids Res* (1990) 18:2661–2669. Compositions of "parallel-stranded DNA" designed to form hairpins secured with AT linkages using either a 3'-3' inversion or a 5'-5' inversion have been synthesized by van de Sande, J. H., et al., *Science* (1988) 241:551–557. In addition, triple helix formation using oligomers which contain 3'-3' linkages have been described (Horne, D. A., and Dervan, P. B., *J Am Chem Soc* (1990) 112:2435–2437; Froehler, B. C., et al., *Biochemistry* (1992) 31:1603–1609).

The use of triple helix (or triplex) complexes as a means for inhibition of the expression of target gene expression has been previously adduced (International Application No. PCT/US89/05769). Triple helix structures have been shown to interfere with target gene expression (International Application No. PCT/US91/09321; Young, S. L. et al., *Proc Natl Acad Sci* (1991) 88:10023–10026), demonstrating the feasibility of this approach.

Oligomers containing 5-propynyl modified pyrimidines have been described (Froehler, B. C., et al., *Tetrahedron*

Letters (1992) 33:5307–5310; and Froehler, B. C., et al., Tetrahedron Letters (1993) 34:1003–1006).

2'-deoxy-7-deazaadenosine and 2'-deoxy-7-deazaguanosine have been incorporated into oligodeoxynucleotides and assessed for binding to the complementary DNA sequences. Thermal denaturation analysis (Tm) has shown that these substitutions modestly decrease the Tm of the duplex when these analogs are substituted for 2'-deoxyadenosine and 2'-deoxyguanosine (Seela, F. and Kehne, A., *Biochemistry* (1987) 26:2232–2238; and Seela, F. and Driller, H., *Nucleic Acids Res* (1986) 14:2319–2332). It has also been shown that oligonucleotides which alternate 2'-deoxy-7-deazaadenosine and thymidine can have a slightly enhanced duplex Tm over oligonucleotides containing 2'-deoxyadenosine and thymidine (Seela, F. and Kehne, A., *Biochemistry* (1985) 24:7556–7561).

2',3'-dideoxydeazapurine nucleosides have been used as chain terminators for DNA sequencing. 7-propargyl amino linkers are used for incorporation of fluorescent dyes into the nucleoside triphosphates (Prober, J. M. et al., *Science* (1987) 238:336–341).

DNA synthesis via amidite and hydrogen phosphonate chemistries has been described (U.S. Pat. Nos. 4,725,677; 4,415,732; 4,458,066; and 4,959,463).

Oligomers having enhanced affinity for complementary target nucleic acid sequences or enhanced nuclease stability would have improved properties for diagnostic applications, therapeutic applications and research reagents. Thus, a need exists for oligomers with one or both of these properties. Oligomers of the present invention have improved binding affinity for double stranded and/or single stranded target sequences or enhanced nuclease stability.

DISCLOSURE OF THE INVENTION

The principal objects of this invention are accomplished by an oligomer comprising at least two nucleomonomers wherein at least one nucleomonomer comprises a base of formula (1) or (2)

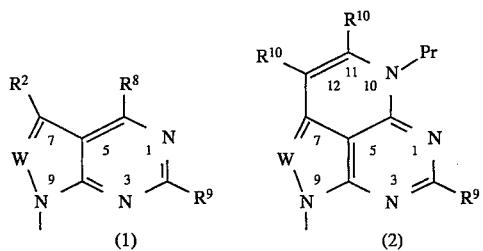

wherein

Pr is H (hydrogen) or a protecting group;

W is CH or N;

$R^2$ is H, methyl, or a group containing a C atom connected to the 7-position of the base, wherein the C atom is bonded directly to another atom via a pi bond;

$R^8$ is OH, SH or $NH_2$;

$R^9$ is H, OH, SH or $NH_2$;

$R^{10}$ is independently H, OH, CN, halogen (F, Cl, Br, I), alkyl (C1–12), alkenyl (C2–12), alkynyl (C2–12), aryl (C6–9), heteroaryl (C4–9), or both $R^{10}$, taken together with the carbon atoms to which they are linked at positions 11 and 12, form (a) a 5 or 6 membered carbocyclic ring or, (b) a 5 or 6 membered heterocyclic ring comprising 1–3 N, O or S ring atoms, provided that no 2 adjacent ring atoms are O—O, S—S, O—S or S—O, and wherein any unsaturated C atom of the carbocyclic or heterocyclic ring is substituted by $R^{11}$ and any saturated carbons contain 2 $R^{11}$ substituents, wherein;

$R^{11}$ is independently H, alkyl (C1–4), alkenyl (C2–4), alkynyl (C2–4), $OR^{12}$, $SR^{12}$, or $N(R^{12})_2$ or halogen provided that there are no more than four halogens per 5 or 6 member ring; and $R^{12}$ is independently H, or alkyl (C1–4);

with the proviso that when W is CH, $R^2$ is H, $R^8$ is $NH_2$ and $R^9$ is H, or when W is CH, $R^2$ is H $R^8$ is OH and $R^9$ is $NH_2$, then the remainder of the nucleomonomers comprising said oligomer are not solely comprised of phosphodiester linked 2'-deoxyadenosine, 2'-deoxyguanosine, 2'-deoxycytidine, thymidine or a combination thereof.

The structural formulas are intended to include all tautomers of the invention bases. For example, in structure (1) when W is CH, $R^2$ is H, $R^8$ is OH and $R^9$ is $NH_2$ the structure is 7-deazaguanine, i.e. 3,7-dihydro-2-amino-pyrrolo[2,3-d] pyrimidin-4-one and when W is CH, $R^2$ is H, $R^8$ is $NH_2$ and $R^9$ is H is the structure 7-deazaadenine, i.e. 4-amino-7H-pyrrolo[2,3-d]pyrimidine.

Invention embodiments include oligomers wherein both $R^{10}$ in the base of formula (2) when taken together are of the formula

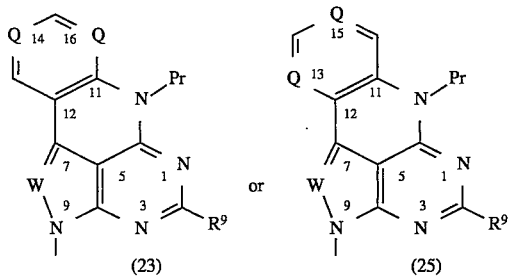

wherein Q is independently N or $CR^{11}$.

BRIEF DESCRIPTION OF FIGURES

FIGS. 4-1 to 4-2. Synthesis of 7-deazapurine nucleomonomers.

FIGS. 5-1 to 5-2. Conversion to 7-substituted deazapurine nucleomonomers.

FIGS. 8-1 to 8-2. Synthesis of trimer linked by a 3'-thioformacetal linkage (method #2).

FIGS. 10-1 to 10-4. Coupling groups for oligomer synthesis via amidite or triester chemistry.

FIGS. 12-1 to 12-3. Oligomer synthesis by (1) hydrogenphosphonate, (2) amidite chemistry and (3) methyl phosphonate derivatives (method #1).

FIGS. 16-1 to 16-2. Synthesis of tetracyclic deazapurine nucleomonomers.

FIGS. 17-1 to 17-3. Oligomers containing amide substitute linkages; repeating nucleomonomer units and exemplary amide-linked oligomer structures.

STRUCTURAL FORMULAS

Figure 1:
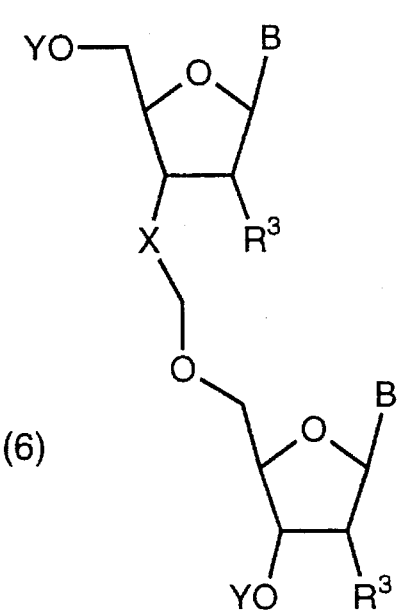
FIG. 1. Dimer synthons containing bases of the invention.
Figure 1:
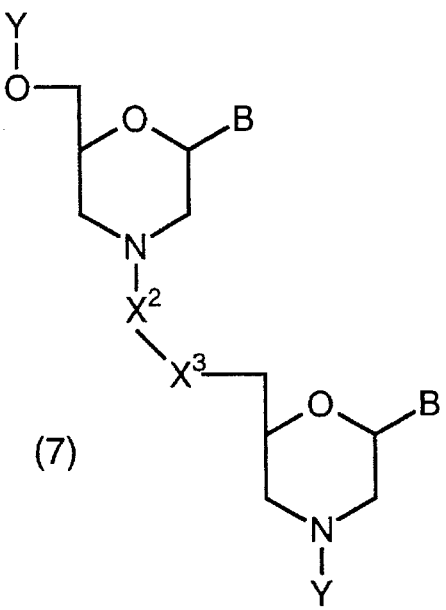

Structural formulas that are described herein are designated as a numeral in parentheses ((1), (2), etc.) and chemical compounds are designated as an underlined numeral (1, 2, etc.). The numbering of bases of structural formulas (1), (2), (23) and (25) herein is informal.

Definitions

The following definitions are brief synopses of terms that are more fully defined herein below.

Nucleomonomer

As used herein, the term "nucleomonomer" means a moiety comprising (1) a base covalently linked to (2) a second moiety. Nucleomonomers include nucleosides and nucleotides. Nucleomonomers can be linked to form oligomers that bind to target or complementary base sequences in nucleic acids in a sequence specific manner.

A "second moiety" as used herein includes those species which contain modifications of the sugar moiety, for example, wherein one or more of the hydroxyl groups are replaced with a halogen, a heteroatom, an aliphatic group, or are functionalized as ethers, amines, and the like. The pentose moiety can be replaced by a hexose or an alternate structure such as a cyclopentane ring, a 6-member morpholino ring and the like. Nucleosides as defined herein are also intended to include a base linked to an amino acid and/or an amino acid analog having a free carboxyl group and/or a free amino group and/or protected forms thereof.

Base

"Base" (referred to herein as "B") as used herein includes the known purine and pyrimidine heterocyclic bases and the invention deazapurines, as well as analogs (including heterocycle substituted analogues) and tautomers thereof. Purines include adenine, guanine, inosine, diaminopurine and xanthine and an exemplary purine analog is 8-oxo-$N^6$-methyladenine. Pyrimidines include thymine, uracil and cytosine and their analogs such as 5-methylcytosine, 5-methyluracil, 5-(1-propynyl)uracil, 5-(1-propynyl)cytosine and 4,4-ethanocytosine. Bases also include non-purinyl and non-pyrimidinyl heterocycles such as 2-aminopyridine and triazines.

Invention bases are deazapurines of structural formulas (1) and (2), which include pyrrolopyrimidines (W=CH) and pyrazolopyrimidines (W=N) substituted at the 7-position.

Nucleoside

As used herein, "nucleoside" means a base covalently attached to a sugar or sugar analog and which may contain a phosphite or phosphine. The term nucleoside includes ribonucleosides, deoxyribonucleosides, or any other nucleoside which is an N-glycoside or C-glycoside of a base. The stereochemistry of the sugar carbons can be other than that of D-ribose.

Nucleosides include those species which contain modifications of the sugar moiety, for example, wherein one or more of the hydroxyl groups are replaced with a halogen, a heteroatom, an aliphatic groups, or are functionalized as ethers, amines, thiols, and the like. The pentose moiety can be replaced by a hexose and incorporated into oligomers as described (Augustyns, K., et al., *Nucl Acids Res* (1992) 18:4711–4716). Also included are analogs where the ribose or deoxyribose moiety is replaced by an alternate structure such as a hexose or the 6-member morpholino ring described in U.S. Pat. No. 5,034,506. Nucleosides as defined herein are also intended to include a base linked to an amino acid and/or an amino acid analog having a free carboxyl group and/or a free amino group and/or protected forms thereof.

Nucleotide

As used herein, "nucleotide" means nucleoside having a phosphate group or phosphate analog.

Sugar Modification

As used herein, "sugar modification" means any pentose or hexose moiety other than 2'-deoxyribose. Modified sugars include D-ribose, 2'-O-alkyl, 2'-amino, 2'-S-alkyl, 2'-halo functionalized pentoses, hexoses and the like. Sugars having a stereochemistry other than that of a D-ribose are also included.

Linkage

As used herein, "linkage" means a phosphodiester moiety (—O—P(O)(O)—O—) that covalently couples adjacent nucleomonomers.

Substitute Linkages

As used herein, "substitute linkage" means any analog of the native phosphodiester group that covalently couples adjacent nucleomonomers. Substitute linkages include phosphodiester analogs, e.g. such as phosphorothioate and methylphosphonate, and nonphosphorus containing linkages, e.g. such as acetals and amides.

Switchback

As used herein, "switchback" means an oligomer having at least one region of inverted polarity. Switchback oligomers are able to bind to opposite strands of a duplex to form a triplex on both strands of the duplex. The linker joining the regions of inverted polarity is a substitute linkage.

Oligomer

Oligomers are defined herein as two or more nucleomonomers covalently coupled to each other by a linkage or substitute linkage moiety. Thus, an oligomer can have as few as two nucleomonomers (a dimer). As used herein oligomer includes oligonucleotides, oligonucleosides, polydeoxyribonucleotides (containing 2'-deoxy-D-ribose or modified forms thereof), i.e., DNA, polyribonucleotides (containing D-ribose or modified forms thereof), i.e., RNA, and any other type of polynucleotide which is an N-glycoside or C-glycoside of a purine or pyrimidine base, or modified purine or pyrimidine base. Oligomer as used herein is also intended to include compounds where adjacent nucleomonomers are linked via amide linkages as previously described (Nielsen, P. E., et al., *Science* (1991) 254:1497–1500). Oligomers can be binding competent and, thus, can base pair with cognate single-stranded or double-stranded nucleic acid sequences. Oligomers (e.g. dimers—hexamers) are also useful as synthons for longer oligomers as described herein. Oligomers can also contain abasic sites and pseudonucleosides.

The competence of binding by oligomers containing the bases of the present invention is believed to be primarily a function of the base alone. Because of this, elements ordinarily found in oligomers, such as the furanose ring and/or the phosphodiester linkage can be replaced with any suitable functionally equivalent element. "Oligomer" is thus intended to include any structure that serves as a scaffold or support for the bases wherein the scaffold permits binding to target nucleic acids in a sequence-dependent manner. Oligomers that are currently known can be defined into four groups that can be characterized as having (i) phosphodiester and phosphodiester analog (phosphorothioate, methylphosphonate, etc) linkages, (ii) substitute linkages that contain a non-phosphorous isostere (formacetal, riboacetal, carbamate, etc), (iii) morpholino residues, carbocyclic residues or other furanose sugars, such as arabinose, or a hexose in place of ribose or deoxyribose and (iv) nucleomonomers linked via amide bonds or acyclic nucleomonomers linked via any suitable substitute linkage.

Blocking Group

As used herein, "blocking group" refers to a substituent other than H that is conventionally attached to oligomers or nucleomonomers, either as a protecting group, a coupling group for synthesis, $PO_3^{-2}$, or other conventional conjugate such as a solid support, label, antibody, monoclonal antibody or fragment thereof and the like. As used herein, "blocking group" is not intended to be construed solely as a protecting group, according to slang terminology, but also includes, for example, coupling groups such as a hydrogen phosphonate or a phosphoramidite.

Protecting group

"Protecting group" (designated herein as "Pr") as used herein means any group capable of preventing the O-atom or N-atom to which it is attached from participating in a reaction or bonding. Such protecting groups for O- and N-atoms in nucleomonomers are described and methods for their introduction are conventionally known in the art. Protecting groups also prevent reactions and bonding at carboxylic acids, thiols and the like.

Coupling group.

"Coupling group" as used herein means any group suitable for generating a linkage or substitute linkage between nucleomonomers such as a hydrogen phosphonate or a phosphoramidite.

Conjugate

"Conjugate" as used herein means any group attached to the oligomer at a terminal end or within the oligomer itself. Conjugates include solid supports, such as silica gel, controlled pore glass and polystyrene; labels, such as fluorescent, chemiluminescent, radioactive, enzymatic moieties and reporter groups; oligomer transport agents, such as polycations, serum proteins and glycoproteins and polymers and the like.

Pi bond

"Pi bond" as used herein means an unsaturated covalent bond such as a double or triple bond. Both atoms can be carbon or one can be carbon and the other nitrogen, for example, phenyl, propynyl, cyano and the like.

Synthon

"Synthon" as used herein means a structural unit within a molecule that can be formed and/or assembled by known or conceivable synthetic operations.

Transfection

"Transfection" as used herein refers to any method that is suitable for enhanced delivery of oligomers into cells.

Subject

"Subject" as used herein means an animal, including a mammal, particularly a human.

Alkyl

By "alkyl" is meant a saturated acyclic or cyclic group having from one to 20 carbon atoms, usually one to 12 carbon atoms. Exemplary alkyl groups include methyl, ethyl, propyl, isopropyl, cyclopropyl, butyl, isobutyl, pentyl and hexyl.

Alkenyl

By "alkenyl" is meant an olefinically-unsaturated group having from two to 20 carbon atoms, usually two to 12 carbon atoms. Exemplary 1-alkenyl groups include vinyl ($-CH=CH_2$), 1-propenyl ($-CH=CH-CH_3$), 2-methyl-1-propenyl ($-CH=C(CH_3)-CH_3$), 1-butenyl ($-CH=CH-CH_2-CH_3$), 1-pentenyl, 1-hexenyl, 1-heptenyl and 1-octenyl, which group is optionally substituted by halogen (one to four halogen atoms) or by an alkyl group having one to four carbon atoms.

Alkynyl

By "alkynyl" is meant an acetylenically-unsaturated group having from two to 20 carbon atoms, usually two to 12 carbon atoms. Exemplary 1-alkynyl groups include ethynyl ($-C\equiv CH$), 1-propynyl ($-C\equiv C-CH_3$), 1-butynyl ($-C\equiv C-CH_2-CH_3$), 3-methyl-butynyl ($-C\equiv C-CH(CH_3)-CH_3$), 3,3-dimethyl-butynyl ($-C\equiv C-C(CH_3)_3$), 1-pentynyl ($-C\equiv C-CH_2-CH_2-CH_3$) and 1,3-pentadiynyl ($-C\equiv C-C\equiv C-CH_3$), which group is optionally substituted by an aryl or heteroaryl group. Exemplary aryl and heteroaryl substitutions include phenylethynyl, 2-, 3- and 4-pyridine-ethynyl, 2-, 4- and 5-pyrimidine-ethynyl, 2- and 3-furan-ethynyl, 2-, 4- and 5-oxazole-ethynyl, 2- and 3-pyrrol-ethynyl, 2-s-triazine-ethynyl, 2- and 3-thiophene-ethynyl, 2-, 4- and 5-thiazole-ethynyl and 2-, 4- and 5-imidazole-ethynyl.

Carbocyclic

By "carbocyclic" ring is meant a saturated or unsaturated ring comprising 5, 6 or 7 ring atoms, which atoms are all carbon atoms. Carbocyclic rings or groups include cyclopentyl, cyclohexyl and phenyl groups. Saturated C atoms have $sp^3$ hybridization and unsaturated C atoms have $sp^2$ hybridization.

Heterocyclic

By "heterocyclic" ring is meant a saturated or unsaturated ring comprising 5, 6 or 7 ring atoms, which atoms are C (carbon) and 1, 2 or 3 N (nitrogen), O (oxygen) or S (sulfur). In general no two adjacent ring atoms are O—O, S—S, O—S or S—O. Heterocyclic rings or groups include pyrimidinyl, pyridinyl, pyrrolinyl and morpholinyl.

Aryl and heteroaryl

By "aryl" and "heteroaryl" (or "heteroaromatic") is meant a carbocyclic or heterocyclic group comprising at least one ring having physical and chemical properties resembling compounds such as an aromatic group of from 5 to 6 ring atoms and comprising 4 to 20 carbon atoms, usually 4 to 9 or 4 to 12 carbon atoms, in which one to three ring atoms is N, S or O, provided that no adjacent ring atoms are O—O, S—S, O—S or S—O. Aryl and heteroaryl groups include, phenyl, 2-, 4- and 5-pyrimidinyl, 2-, 4- and 5-thiazoyl, 2-s-triazinyl, 2-, 4-imidazolyl, 2-, 4- and 5-oxazolyl, 2-, 3- and 4-pyridyl, 2- and 3-thienyl, 2- and 3-furanyl, 2- and 3-pyrrolyl optionally substituted preferably on a ring C by oxygen, alkyl of 1–4 carbon atoms or halogen. Heteroaryl groups also include optional substitution on a ring N by alkyl of 1–4 carbon atoms or haloalkyl of 1–4 carbon atoms and 1–4 halogen atoms. Exemplary substituents on the aryl or heteroaryl group include methyl, ethyl, trifluoromethyl and bromo. Such substituted aryl and heteroaryl groups include benzyl and the like. "Heteroaryl" also means systems having two or more rings, including bicyclic moieties such as benzimidazole, benzotriazole, benzoxazole, and indole.

Halogen

By "halogen" is meant an atom selected from the group consisting of fluorine, chlorine, bromine and iodine. Substitutions including bromovinyl can be included in the oligomers.

DETAILED DESCRIPTION OF THE INVENTION

Oligomers including either or both of the modified bases of formulas (1) or (2) bind to complementary sequences in a sequence-specific manner and can show enhanced binding capacities in the formation of duplexes or triplexes with single-stranded RNA or DNA or duplex target sequences, respectively.

When the 7-substituted 7-deazapurines of formula (1) and (2) noted above are present, additional nucleomonomer modifications can vary widely as discussed herein. In general, an additional modification comprises oligomers having at least one substitute linkage or a sugar modification such as a 2'-substituted deoxyribose.

The substitution of a base of formula (1) of the invention, such as in 7-alkenyl, 7-alkynyl, 7-heteroaromatic- or 7-alkynyl-heteroaromatic-substituted bases or a base of formula (2), for adenosine or guanosine in oligomers which target DNA duplexes provides binding competent oligomers with enhanced binding affinity. In addition, some of the 7-substituted deazapurine base residues significantly enhance triple helix formation with double stranded DNA as compared with the oligomers containing natural purine nucleomonomers. The oligomers of the invention are thus capable of forming triplexes with various target sequences such as those found in oncogenes or viruses by binding in the major groove of a target DNA duplex under physiological pH conditions (Milligan, J. F., et al., *Nucleic Acids Res* (1993) 21:327–333).

Accordingly, in one aspect, the invention is directed to an oligomer comprising at least two nucleomonomers wherein at least one said nucleomonomers comprises a base of formula (1) or (2) above.

In one embodiment of the invention $R^2$ (structural formulas (1), (3), etc) is 1-alkenyl (C2–12) or 1-alkynyl (C2–12) or is a heteroaromatic group (C5–12) containing 5–6 ring atoms in which one to three of the ring atoms is N, S or O provided that no two adjacent ring atoms are O—O, S—S, O—S or S—O. Preferably, $R^2$ is a methyl, 1-alkenyl (C2–8), 1-alkynyl (C2–8), aryl (C6–10) or heteroaryl (C4–10) containing 5–6 ring atoms in which one ring atom is N and optionally a second ring atom is N, S or O.

In another embodiment of the invention $R^{10}$ (structural formulas (2), (4), etc) is independently H, alkyl (C1–12, C1–9, C1–6 or C1–5), 1-alkenyl (C2–12, C2–8 or C2–4) or 1-alkynyl (C2–12, C2–8 or C2–4) or, when both $R^{10}$ taken together form a carbocyclic (C5–12 or C5–10) or heterocyclic ring (C4–12 or C4–10) containing 5–7 ring atoms in which zero to three of the ring atoms is N, S or O provided that no two adjacent ring atoms are O—O, S—S, O—S or S—O. Preferably, $R^{10}$ is independently H, methyl, 1-alkenyl (C2–4), 1-alkynyl (C2–4), aryl (C6–7) or, both $R^{10}$ are taken together to form an aromatic ring (C4–7) containing 5–6 ring atoms in which zero or one ring atom is N and optionally a second ring atom is N.

Figure 2:
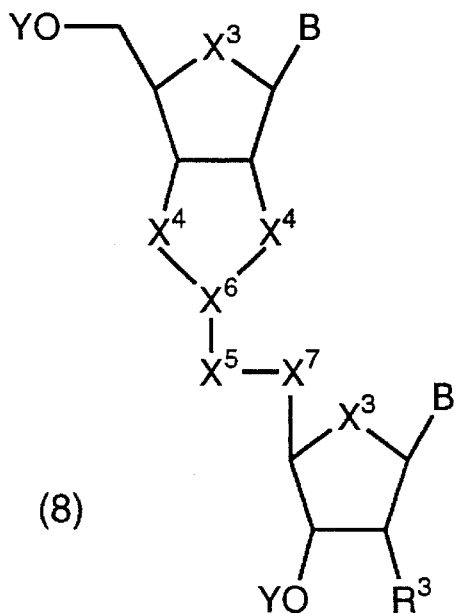
FIG. 2. Dimer synthons containing bases of the invention and containing 5 and 6 membered riboacetal type linkages.
Figure 2:
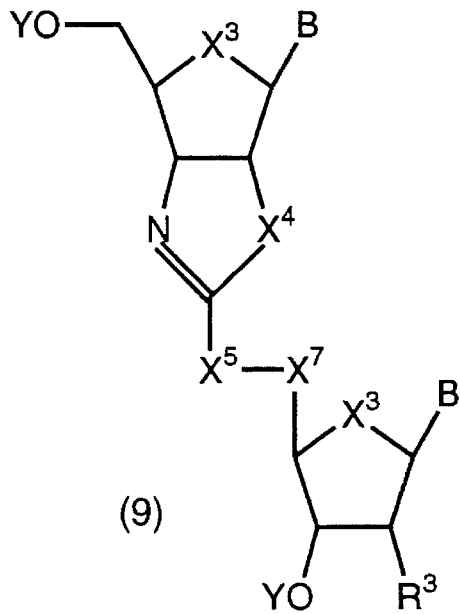
Figure 2:
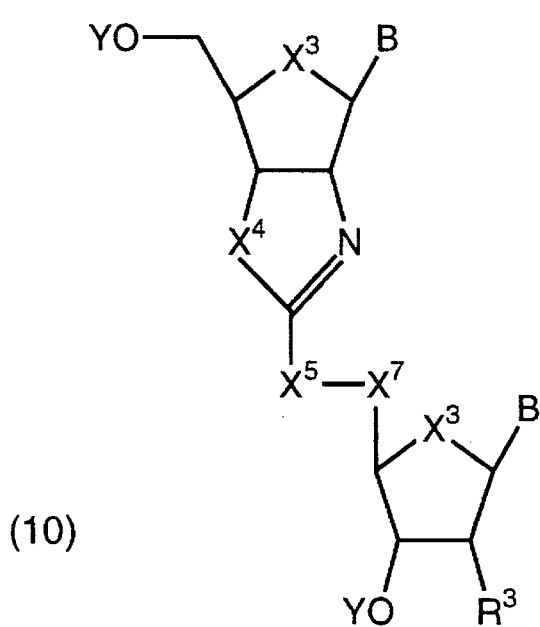
Figure 2:
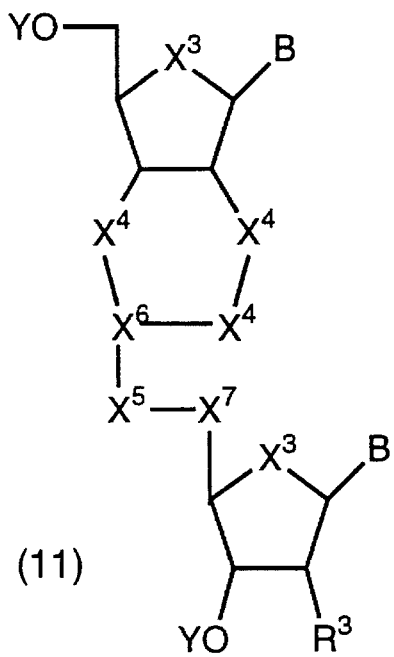
Figures 1, 16:
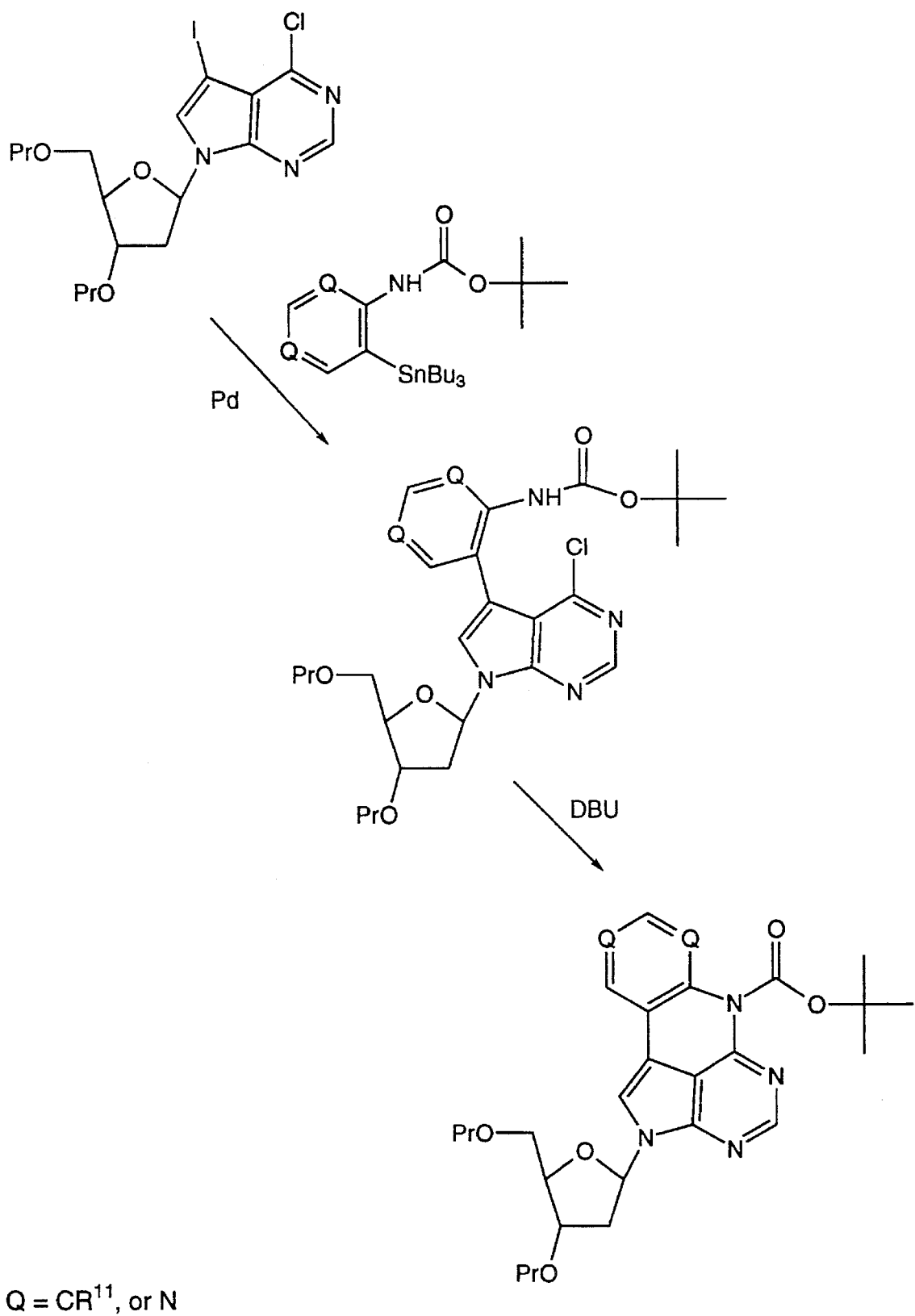

In additional embodiments, both $R^{10}$ together form a 6 member aromatic ring as shown in FIG. 16-2 (structures (23)–(26)) wherein each Q is independently chosen and is $CR^{11}$ or N.

Aspects of the invention include the use of nucleomonomers, two linked nucleomonomers (dimers), three linked nucleomonomers (trimers), four linked nucleomonomers (tetramers), five linked nucleomonomers (pentamers) or six linked nucleomonomers (hexamers) as intermediates in the synthesis of the longer oligomers of the invention. These oligomers are valuable synthons of the invention that are useful in the synthesis of longer oligomers.

In other aspects, the invention is directed to duplexes or triplexes obtained by binding the foregoing oligomers to single-stranded or duplex nucleic acid targets.

Also included are intermediates of the formula (6) shown in FIG. 1, wherein X is selected from the group consisting of O and S; and each Y, B, and $R^3$ is independently selected and has the meaning defined herein.

The oligomers of the invention are also suitable for binding to DNA duplex target sequences via GT triple helix binding motif.

An aspect of the invention is the inclusion of the invention bases in oligomers that are resistant to nuclease degradation relative to an oligodeoxynucleotide having no modifications. Nuclease resistant oligomers of the invention are advantageously used under conditions where nucleases are present. For certain applications nuclease stability by oligomers of the invention is an important functional aspect of the oligomer.

Other aspects of the invention are directed to compositions, reagents and kits comprising the oligomers of the invention.

An additional aspect of the invention includes methods of detecting the presence, absence or amount of a particular single-stranded DNA or RNA or a particular target duplex in a biological (or other) sample using the oligomers of the invention, to detect selected nucleic acid sequences. Such sequences can be associated with the presence of neoplastic growth, viruses or disease conditions. Reagents and kits containing oligomers of the invention represent an aspect of the invention that permit facile use of the oligomers as reagents useful for (1) modulating gene expression in cells in vitro including cells grown in tissue culture, and (2) detecting and/or quantitating target sequences.

It has been found that some of the oligomers of the invention have enhanced binding properties with respect to complementary single-stranded and double-stranded nucleic acid sequences as compared to unmodified oligomers not having the 7-substituted deazapurines of the invention. Triple helix structures can be formed at physiological pH levels of 7.0 and higher.

A feature of the invention is that the oligomers of the invention can be comprised of a variety of different sequences and thereby used to target a variety of different single-stranded or double-stranded target sequences.

An advantage of the present invention is that the oligomers of the invention are capable of forming triplexes under physiological pH conditions.

Another feature of oligomers containing the substituted deazapurine bases (1) or (2) of the invention compared to oligomers containing adenine, guanine, inosine, xanthosine and 2,6-diaminopurine is that the lipophilic group ($R^2$ of the structural formula (1) or $R^{10}$ of the structural formula (2)) can enhance cell permeation or uptake. The nucleomonomers containing these bases are more lipophilic than adenine, guanine, inosine, xanthosine and 2,6-diaminopurine.

Additional Nucleomonomer Modifications.

Oligomers that are comprised of nucleomonomers can also contain modifications in addition to the 7-modified deazapurines of the invention. A non-limiting exemplary list of such additional modifications includes oligomers where (i) one or more nucleomonomer residues are modified at the 2' position, (ii) one or more covalent crosslinking moieties are incorporated, (iii) inverted polarity linkers are incorporated, (iv) substitute linkages are included, (v) other bases, such as 8-oxo-$N^6$-methyladenine, 5-(1-propynyl)cytosine or 5-(1-propynyl)uracil are included and (vi) conjugates such as intercalating agents or polylysine that respectively enhance binding affinity to target nucleic acid sequences or that enhance association of the oligomer with cells are included.

The ability of the 7-substituted bases (1) and (2) of the invention to bind target sequences in a sequence-specific manner or to enhance affinity of the oligomer for single-stranded and duplex targets permits further modifications to the oligomer in which they are contained. These further modifications may or may not diminish binding affinity, but also confer other useful properties such as stability to nuclease cleavage, ability to permeate cell membranes, and the like. Thus, particularly preferred oligomers of the invention can contain substitute linkages and/or modified sugars, as well as the 7-substituted deazapurine bases (1) and (2) of the invention.

The oligomers can also contain additional modifications in the nucleomonomers that contain these 7-modified deazapurines or in other nucleomonomers that comprise the oligomer.

Oligomers

The oligomers of the invention can be formed using invention and conventional nucleomonomers and synthesized using standard solid phase (or solution phase) oligomer synthesis techniques, which are now commercially available. In general, the invention oligomers can be synthesized by a method comprising the steps of: synthesizing a nucleomonomer or oligomer synthon having a protecting group and a base and a coupling group capable of coupling to a nucleomonomer or oligomer; coupling the nucleomonomer or oligomer synthon to an acceptor nucleomonomer or an acceptor oligomer; removing the protecting group; and repeating the cycle as needed until the desired oligomer is synthesized.

The oligomers of the present invention can be of any length including those of greater than 40, 50 or 100 nucleomonomers. In general, preferred oligomers contain 2–30 nucleomonomers. Lengths of greater than or equal to about 8 to 20 nucleomonomers are useful for therapeutic or diagnostic applications. Short oligomers containing 2, 3, 4 or 5 nucleomonomers are specifically included in the present invention and are useful as synthons.

Oligomers having a randomized sequence and containing about 6 or 7 nucleomonomers are useful for primers that are used in cloning or amplification protocols that use random sequence primers, provided that the oligomer contains at least one residue at the 3' end that can serve as a primer for polymerases or reverse transcriptases.

Figures 1, 12:
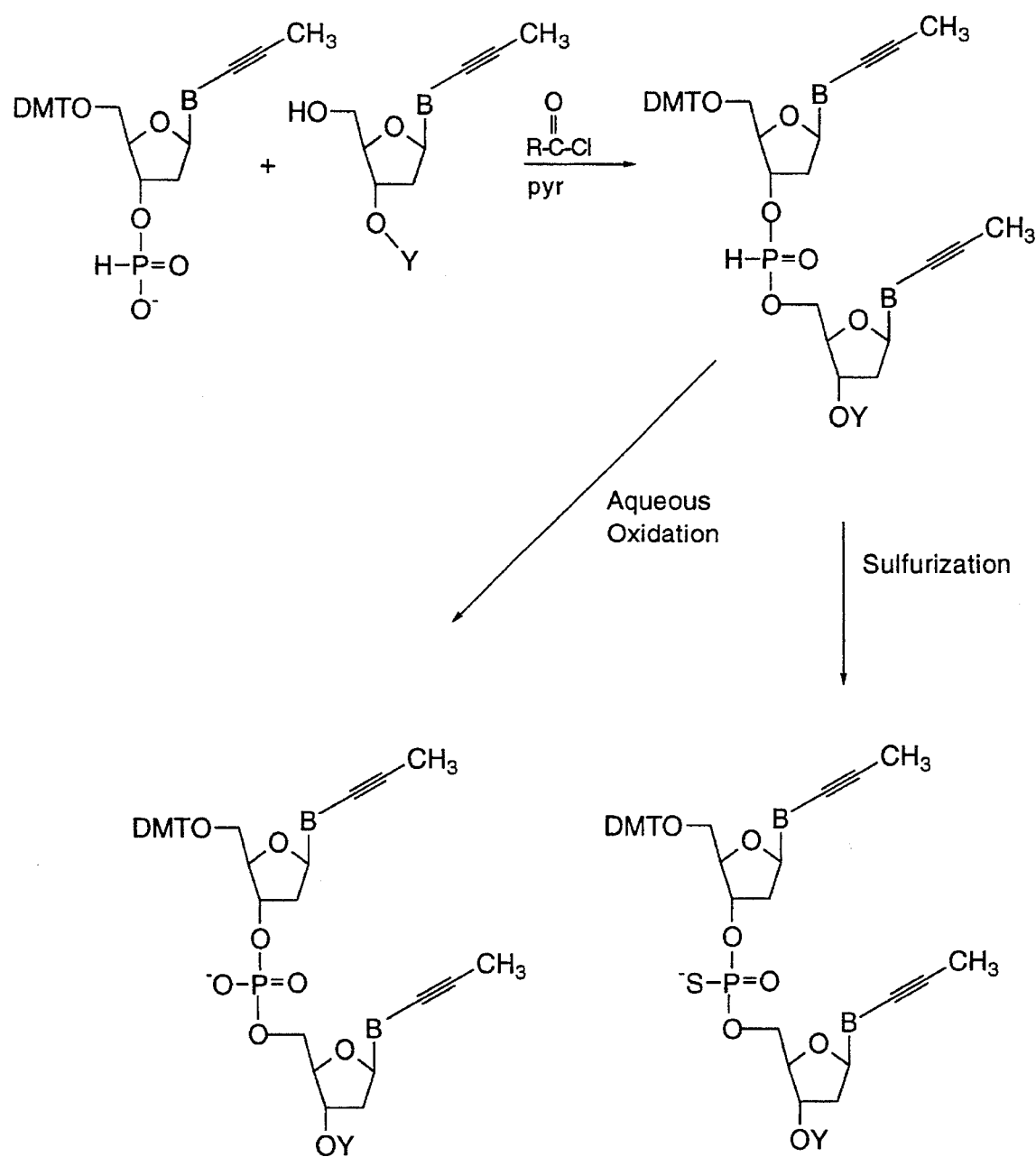
Figures 2, 12:
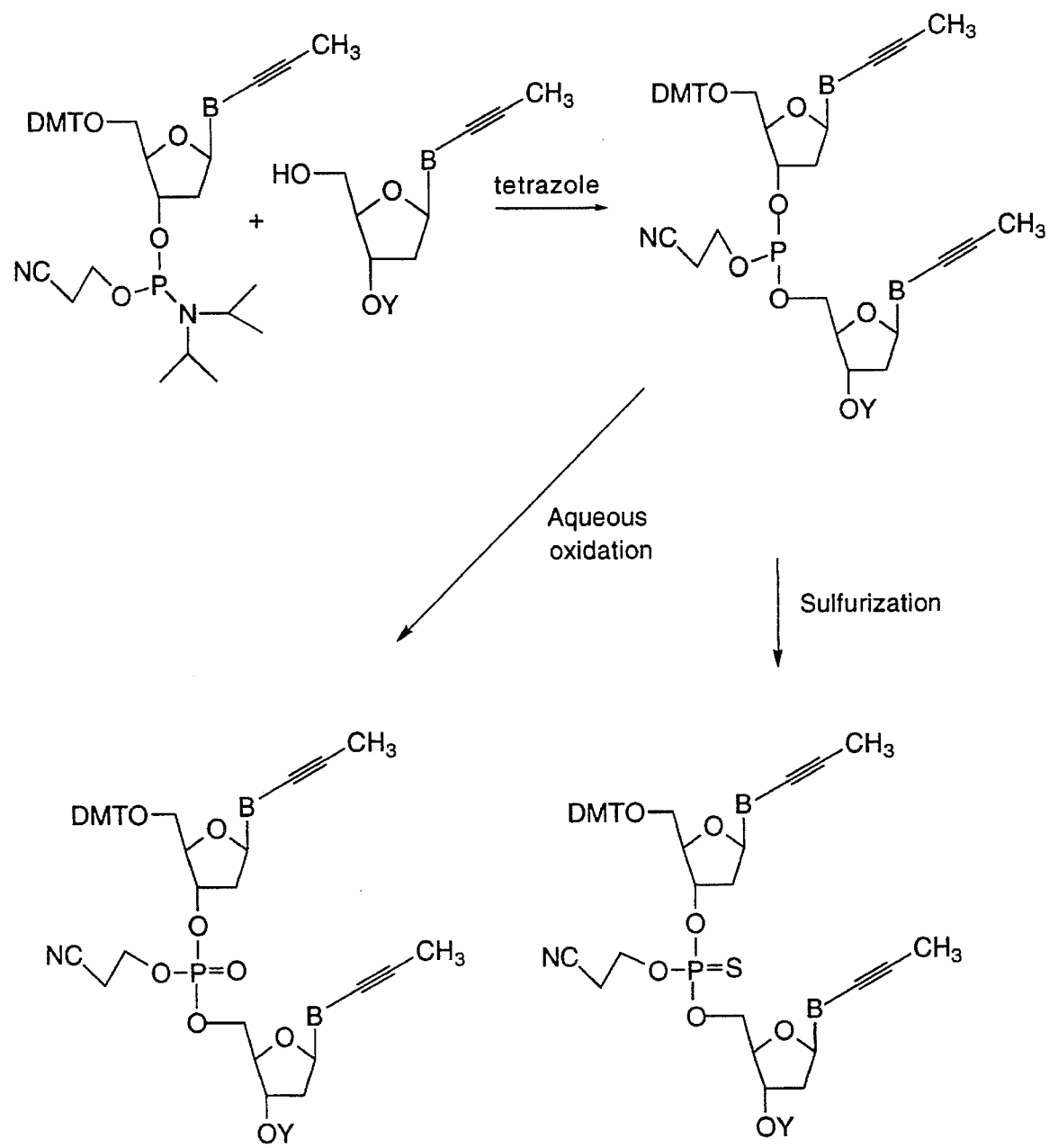
Figures 3, 12:
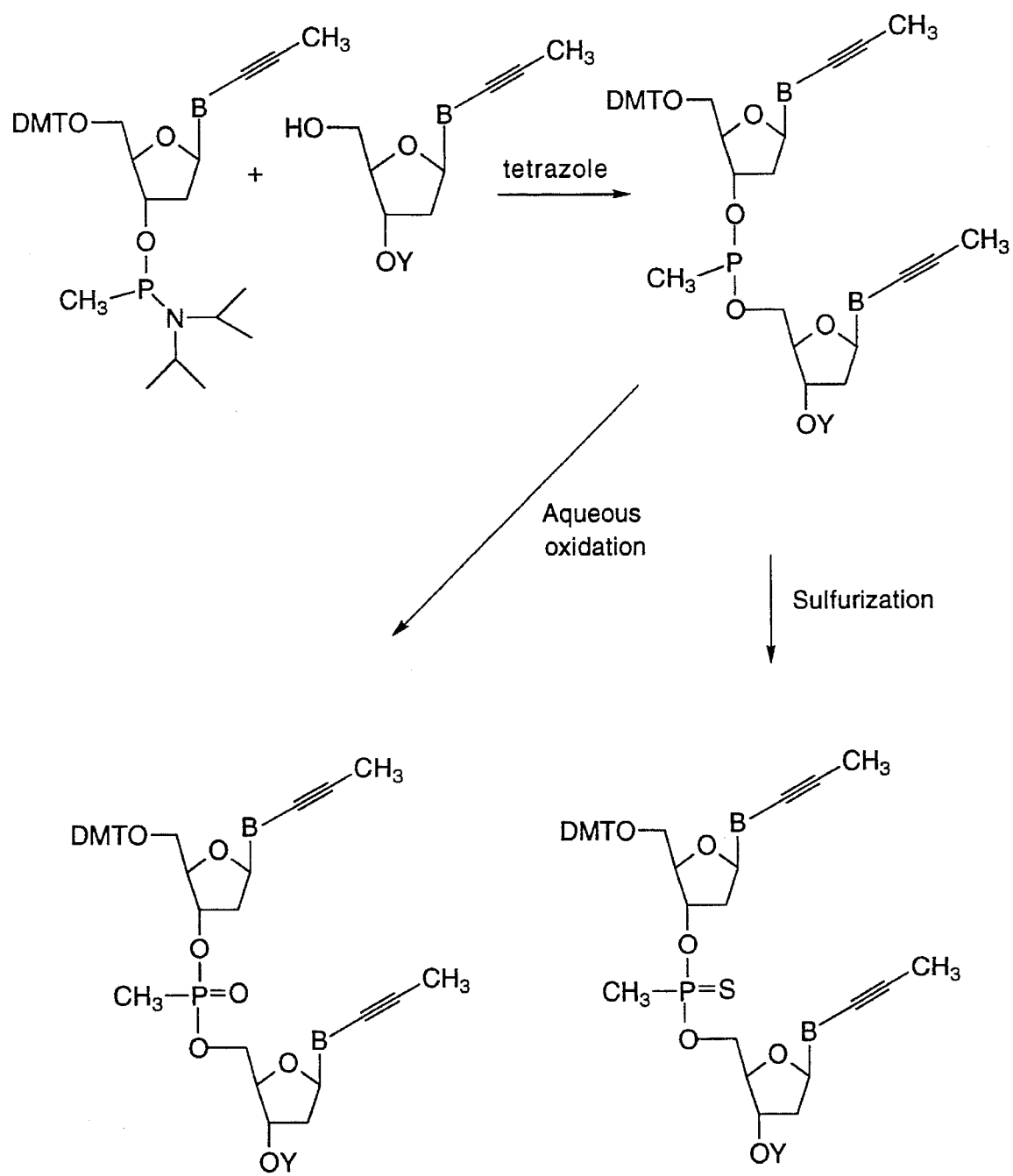

Oligomers can contain conventional phosphodiester linkages or can contain substitute linkages such as phosphoramidate linkages. These substitute linkages include, but are not limited to, embodiments wherein a moiety of the formula
—O—P(O)(S)—O— ("phosphorothioate"),
—O—P(S)(S)—O— ("phosphorodithioate"),
—O—P(O)(NR'$_2$)—X—, —O—P(O)(R')—O—,
—O—P(S)(R')—O— ("thionoalkylphosphonate"),
—P(O)(OR$^6$)—X—, —O—C(O)—X—, or
—O—C(O)(NR'$_2$)—X—, wherein R' is H (or a salt) or alkyl (1–12C) and R$^6$ is alkyl (1–9C) and the linkage is joined to adjacent nucleomonomers through an —O— or —S— bonded to a carbon of the nucleomonomer. Phosphorothioate, methylphosphonate and phosphodiester linkages are shown in FIG. 12. Particularly, preferred substitute linkages for use in the oligomers of the present invention include phosphodiester, phosphorothioate, methylphosphonate and thionomethylphosphonate linkages. Phosphorothioate and methylphosphonate linkages confer added stability to the oligomer in physiological environments. While not all such linkages in the same oligomer need be identical, particularly preferred oligomers of the invention contain uniformly phosphorothioate linkages or uniformly methylphosphonate linkages.

Salts

Any salt can be used and such salt forming materials are well known in the art.

Salts are preferably metal or ammonium salts of said oligomers of the invention and include alkali or alkaline earth metal salts, e.g., the sodium, potassium, magnesium or calcium salt; or advantageously easily crystallizing ammonium salts derived from ammonia or organic amines, such as mono-, di- or tri-lower (alkyl, cycloalkyl or hydroxyalkyl)-amides, lower alkylenediamines or lower (hydroxyalkyl or arylalkyl)-alkylammonium bases, e.g. methylamine, diethylamine, triethylamine, dicyclohexylamine, triethanolamine, ethylenediamine, tris-(hydroxymethyl)-aminomethane or benzyltrimethylammonium hydroxide. The oligomers of the invention form acid addition salts, which are preferably such of inorganic or organic acids, such as strong mineral acids, for example hydrohalic, e.g., hydrochloric or hydrobromic acid; sulfuric, phosphoric; aliphatic or aromatic carboxylic or sulfonic acids, e.g., formic, acetic, propionic, succinic, glycollic, lactic, malic, tartaric, gluconic, citric, ascorbic, maleic, fumaric, hydroxymaleic, pyruvic, phenylacetic, benzoic, 4-aminobenzoic, anthranilic, 4-hydroxybenzoic, salicylic, 4-aminosalicylic, methanesulfonic, ethanesulfonic, hydroxyethanesulfonic, benzenesulfonic, sulfanilic or cyclohexylsulfamic acid and the like.

Blocking Groups

Non-limiting examples of suitable "protecting groups" for N-atoms include diisobutylformamidine, dimethylformamidine, benzoyl, tBOC, FMOC and the like. Suitable "protecting groups" for O-atoms are, for example, DMT, MMT, or FMOC.

Figure 10:
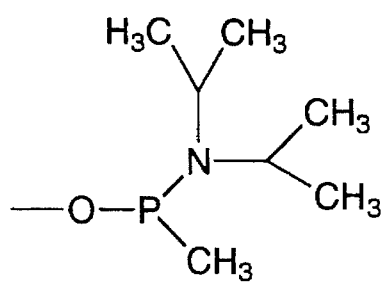
Figure 4:
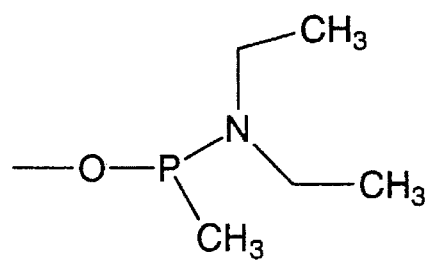

Suitable coupling groups are, for example, H-phosphonate, a methylphosphonamidite, or a phosphoramidite. Phosphoramidites that can be used include β-cyanoethylphosphoramidites (preferred). Methylphosphonamidites, alkylphosphonamidites (including ethylphosphonamidites and propylphosphonamidites) can also be used. Exemplary phosphoramidites are shown in FIGS. 10-1 and 10-2.

Suitable protecting groups are DMT (dimethoxy trityl), MMT (monomethoxytrityl) or FMOC at the 5' terminus and/or hydrogen phosphonate, methyl phosphoramidite, methyl phosphonamidite, β-cyanoethylphosphoramidite at the 3'-terminus.

Protecting Groups

Protecting groups such as dimethylformamidine, di-n-butylformamidine, diisobutylformamidine, dimethylacetamidine, benzoyl, isobutyryl, FMOC, dialkylformamidine, dialkylacetamidine or other groups known in the art can be used to protect the exocyclic nitrogen of the nucleomonomers of the invention. Alternatively, nucleomonomers precursors can be directly incorporated into oligomers without a protecting group at the exocyclic nitrogen using described methods (Gryaznov, S. M. et al., *J Amer Chem Soc* (1991) 113:5876–5877; Gryaznov, S. M., et al., *Nucl Acids Res* (1992) 20:1879–1882; Kung, P.-P., et al., *Tetrahedron Letters* (1992) 40:5869–5872). Synthesis of oligomers having bases (1) containing an $R^2$ as ethynyl heteroaryl substituents is preferably accomplished using 9-fluorenylmethoxycarbonyl (FMOC) for protection of the 5'-hydroxyl position as described (Lehman, C., et al., *Nucl Acids Res* (1989) 17:2379–2390).

Preferred protecting groups are DMT (dimethoxy trityl), MMT (monomethoxytrityl) or FMOC at the 5' terminus and/or hydrogen phosphonate, methyl phosphoramidite, methyl phosphonamidite, β-cyanoethylphosphoramidite at the 3'-terminus. However, it is intended that the position of the blocking groups can be reversed as needed (e.g., a phosphoramidite at the 5'-position and DMT at the 3'-position). In general, the nucleomonomers and oligomers of the invention can be derivatized to such "blocking groups" as indicated in the relevant formulas by methods known in the art.

Coupling Groups

Figure 3:
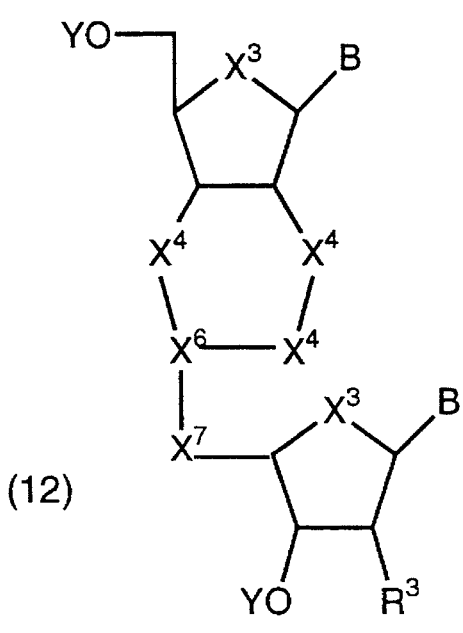
FIG. 3. Dimer synthons containing bases of the invention and containing 6 and 7 membered riboacetal type linkages.
Figure 3:
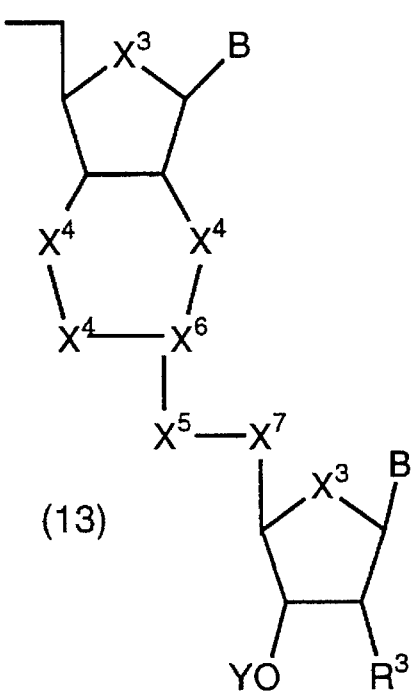
Figure 3:
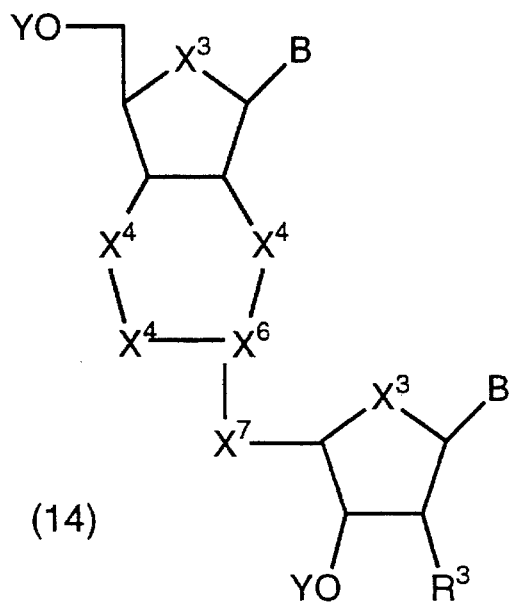
Figure 3:
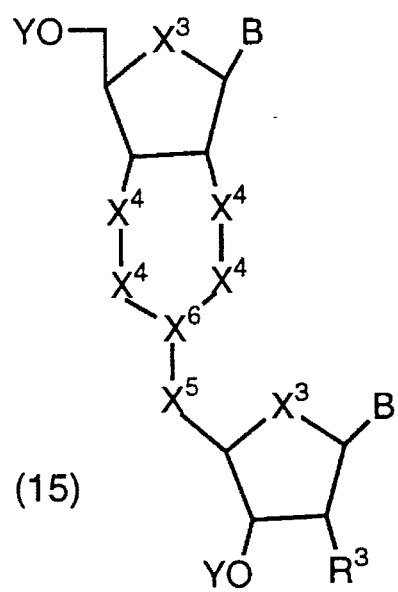
Figures 1, 4:
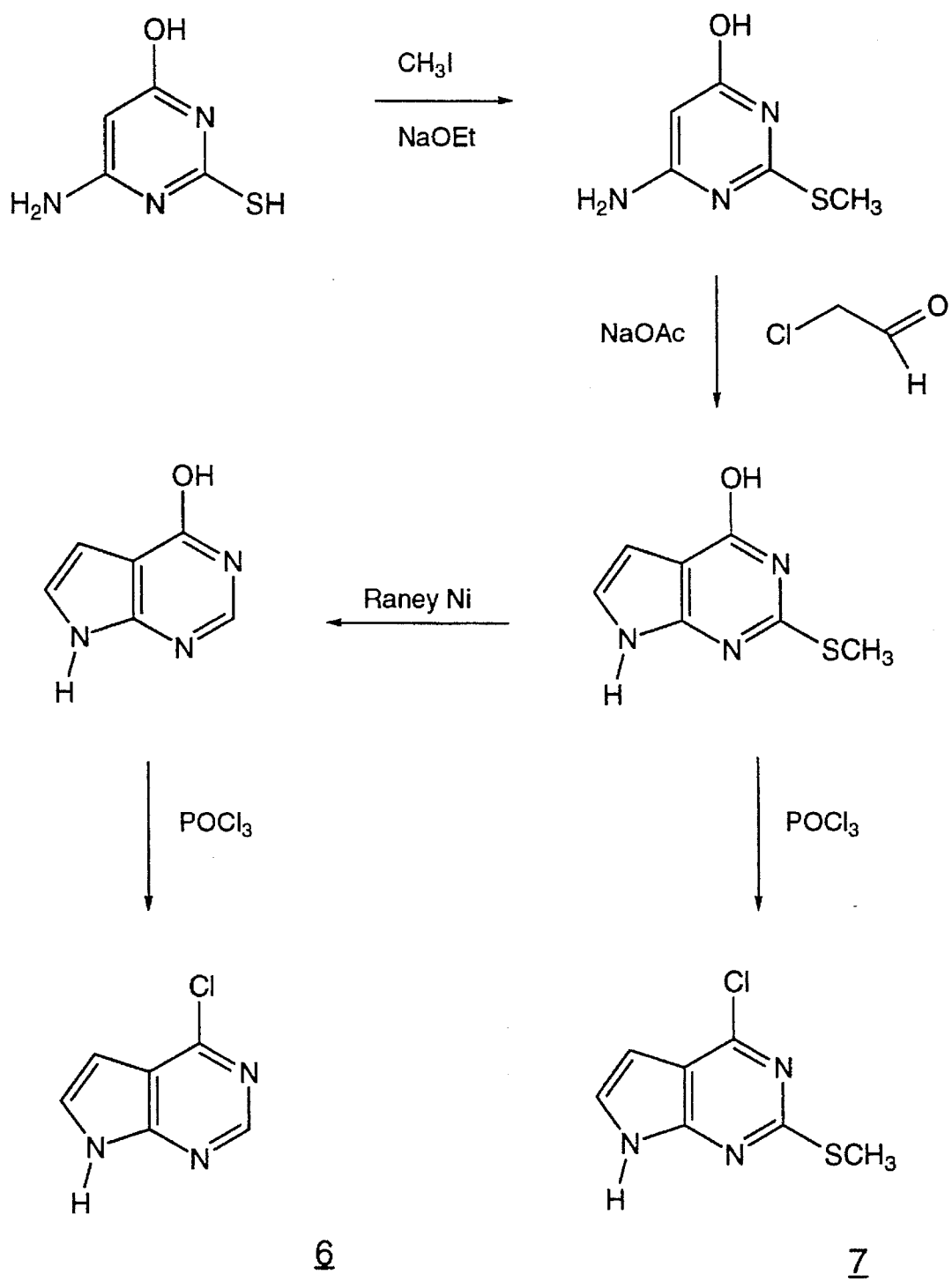
Figures 2, 4:
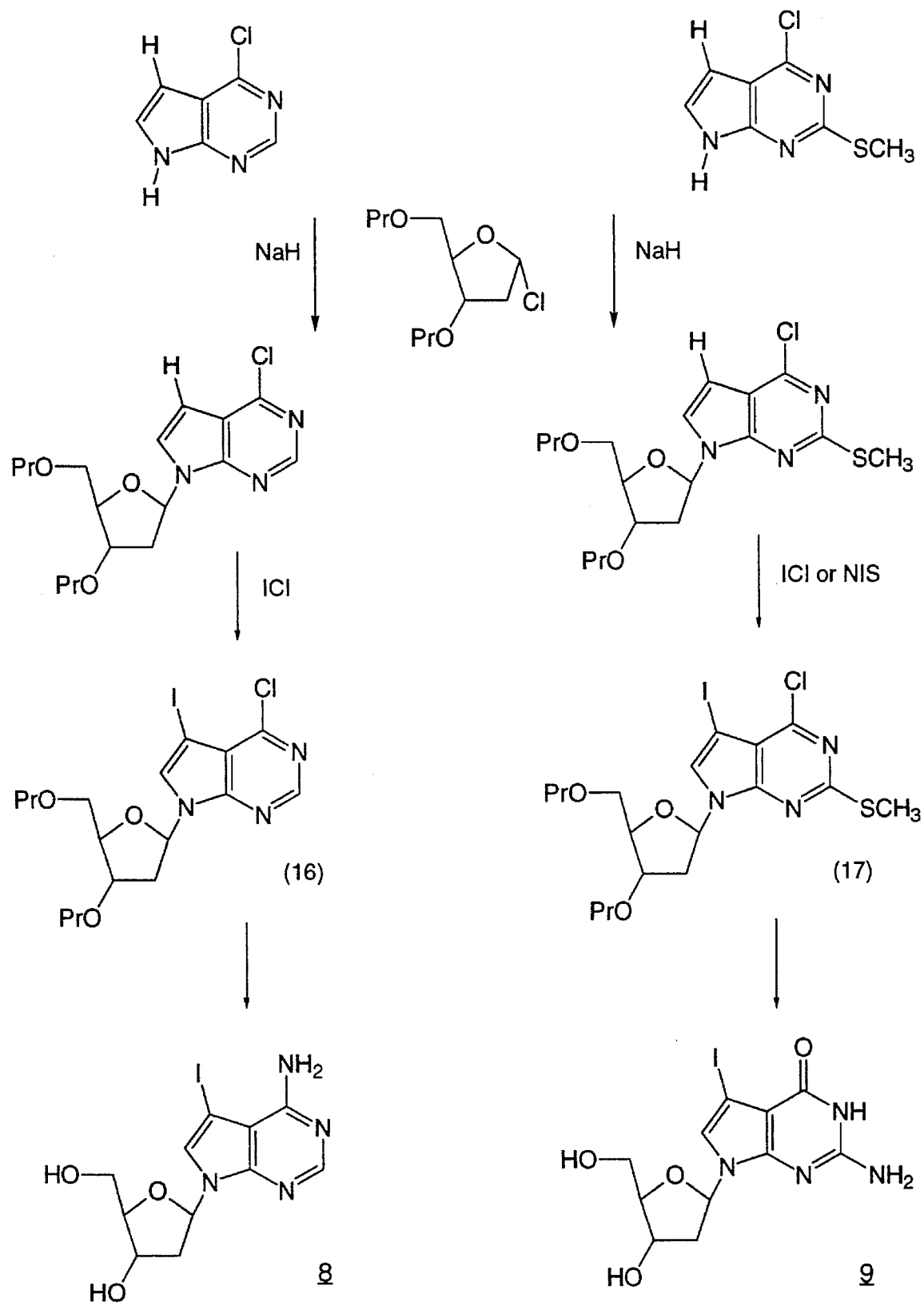

Suitable coupling groups are, for example, H-phosphonate, a methylphosphonamidite, or a phosphoramidite. Phosphoramidites that can be used include β-cyanoethylphosphoramidites (preferred). Methylphosphonamidites, alkylphosphonamidites (including ethylphosphonamidites and propylphosphonamidites) can also be used. Exemplary phosphoramidites are shown in FIGS. 10-1 and 10-2. Suitable "coupling groups" at the 3', 2' or 5' position for oligomer synthesis via phosphoramidite triester chemistry, referred to herein as "amidite" chemistry, include N,N-diisopropylamino-β-cyanoethoxyphosphine, N,N-diisopropylaminomethoxyphosphine, N,N-diethylamino-β-cyanoethoxyphosphine, (N-morpholino)-β-cyanoethoxyphosphine, and (N-morpholino)-methoxyphosphine (Moore, M. F. et al., *J Org Chem* (1985) 50:2019–2025; Uznanski, A. W., et al., *Tet Lett* (1987) 28:3401–3404; Bjergarde, K., et al., *Nucl Acids Res* (1991)21:5843–5850; Dahl, O. *Sulfur Reports* (1991) 11:167–192). Related coupling groups such as N,N-diisopropylamino-methyl-phosphine or N,N-diethylamino-methyl-phosphine can also be used to prepare methylphosphonates (FIG. 10-4). Methylphosphonate oligomers can be conveniently synthesized using coupling groups such as N,N-diisopropylamino-methylphosphonamidite, and N,N-diethylamino-methylphosponamidite. Synthesis of nucleomonomer amidites of the invention can be accomplished by conventional methods (for example, Gryaznov, S. M., et al., *Nucl Acids Res* (1992) 20:1879–1882; Vinayak, R., et al., *Nucl Acids Res* (1992) 20:1265–1269; Sinha, N. D., et al., *Nucl Acids Res* (1984) 12:4539–4557; and other references cited herein). Suitable coupling groups at the 3', 2' (or 5') position for oligomer synthesis via phosphate triester chemistry, referred to herein as "triester" chemistry, include 2-chlorophenyl phosphate, 4-chlorophenyl phosphate, 2,4-dichlorophenyl phosphate and 2,4,-dibromophenyl phosphate nucleotide diester derivatives or, for synthesis of phosphorothioate linkages, the thiono derivatives thereof (Marugg, J. E., et al., *Nucl Acids Res* (1984) 12:9095–9110; Kemal, O., et al., *J Chem Soc Chem Commun* (1983) 591–593; Kamer, P. C. J., et al., *Tet Lett* (1989) 30:6757–6760). Structures of these coupling groups are shown in FIG. 10-3 where X is O or S and $Z^1$ is H or a suitable benzotriazole.

Oligomers or the segments thereof are conventionally synthesized. The synthetic methods known in the art and described herein can be used to synthesize oligomers containing bases of the invention, as well as other bases known in the art, using appropriately protected nucleomonomers (see FIG. 12). Methods for the synthesis of oligomers are found, for example, in Froehler, B., et al., *Nucleic Acids Res* (1986) 14:5399–5467; *Nucleic Acids Res* (1988) 16:4831–4839; *Nucleosides and Nucleotides* (1987) 27:287–291; Froehler, B., *Tetrahedron Letters* (1986) 27:5575–5578; Caruthers, M. H. in *Oligodeoxynucleotides-Antisense Inhibitions of Gene Expression* (1989), J. S. Cohen, editor, CRC Press, Boca Raton, p7–24; Reese, C. B. et al., *Tetrahedron Letters* (1985) 26:2245–2248. Synthesis of the methylphosphonate linked oligomers via methyl phosphonamidite chemistry has also been described (Agrawal, S. et al., *Tetrahedron Letters* (1987) 28:3539–3542; Klem, R. E., et al., International Publication Number WO 92/07864).

Conjugates

Also included are "conjugates" of oligomers. "Conjugates" of the oligomers include those conventionally recognized in the art. For instance, the oligomers can be covalently linked to various moieties such as, intercalators, and substances which interact specifically with the minor groove of the DNA double helix. Other chosen conjugate moieties, can be labels such as radioactive, fluorescent, enzyme, or moieties which facilitate cell association using cleavage linkers and the like Suitable radiolabels include $^{32}P$, $^{35}S$, $^{3}H$, $^{125}I$, $^{131}I$ and $^{14}C$; and suitable fluorescent labels include fluorescein, resorufin, rhodamine, BODIPY (Molecular Probes) and texas red; suitable enzymes include alkaline phosphatase and horseradish peroxidase. Other compounds which can be used as covalently linked moieties include biotin, antibodies or antibody fragments, transferrin and the HIV Tat protein can also conveniently be linked to the oligomers of the invention.

These additional moieties can be derivatized through any convenient linkage. For example, intercalators, such as acridine or psoralen can be linked to the oligomers of the invention through any available —OH or —SH, e.g., at the terminal 5'-position of the oligomer, the 2'-positions of RNA, or an OH, $NH_2$, COOH or SH incorporated into the 5-position of pyrimidines or 7-position of deazapurines. A derivatized form which contains, for example, —$CH_2CH_2NH_2$, —$CH_2CH_2CH_2OH$ or —$CH_2CH_2CH_2SH$ in the 5-position of pyrimidines or 7-position of deazapurines is preferred. Conjugates including polylysine or lysine can be synthesized as described and can further enhance the binding affinity of an oligomer to its target nucleic acid sequence (Lemaitre, M. et al., *Proc Natl Acad Sci* (1987) 84:648–652; Lemaitre, M. et al., *Nucleosides and Nucleotides* (1987) 6:311–315).

A wide variety of substituents can be attached, including those bound through linkages or substitute linkages. The —OH moieties in the oligomers can be replaced by phosphate groups, protected by standard protecting groups, or coupling groups to prepare additional linkages to other nucleomonomers, or can be bound to the conjugated substituent. The 5'-terminal OH can be phosphorylated; the 2'-OH or OH substituents at the 3'-terminus can also be phosphorylated. The hydroxyls can also be derivatized to standard protecting groups.

Oligomers of the invention can be covalently derivatized to moieties that facilitate cell association using cleavable linkers. Linkers used for such conjugates can include disulfide linkages that are reduced after the oligomer-transport agent conjugate has entered a cell. Appropriate molecular linkers include for example, —$Y^1$—$X^8CH_2CHR^7$—SS—$CHR^7CH_2X^8$—$Y^1$— wherein each $Y^1$ is independently alkylene ($C_{1-6}$; including methylene, ethylene and propylene), or CO, each $X^8$ is independently O, S(O)(O), S(O), $NR^7$, $CH_2$, $C(R^7)_2$ or CO; $R^7$ wherein each $R^7$ is independently H, alkyl ($C_{1-6}$; including methyl, ethyl and propyl), or aryl and which linkers have been previously described (WO 91/14696). Disulfide-containing linkers of this type have a controllable $t_{1/2}$ in vivo, facilitating its use as a prodrug/transport component. Such linkers are stable under extracellular conditions relative to intracellular conditions due to the redox potential of the disulfide linkage.

Suitable conjugates also include solid supports for oligomer synthesis and to facilitate detection of nucleic acid sequences. Solid supports included, but are not limited to, silica gel, controlled pore glass, polystyrene, and magnetic glass beads.

Sugar Modifications

Figure 6:
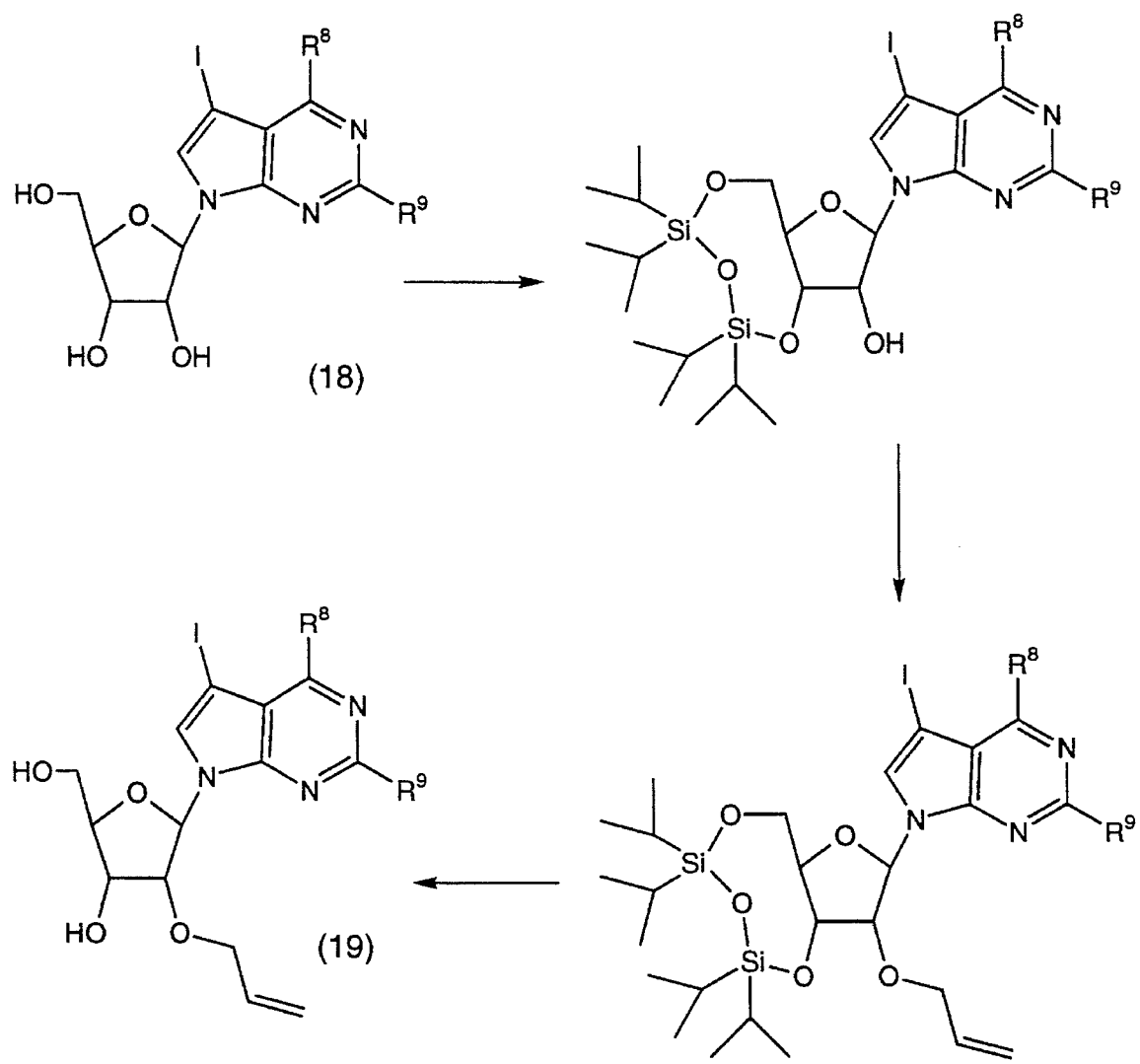
FIG. 6. Synthesis of 2'-O allyl 7-substituted deazapurine nucleomonomers.

Derivatives can be made by substitution on the sugars. Among the most preferred derivatives of the oligomers of the invention are the 2'-O-allyl derivatives (FIG. 6). The presence of the 2'-O-allyl group appears to enhance permeation ability and stability to nuclease degradation, but does not appear to diminish the affinity of the oligomer for single chain or duplex targets.

Furthermore, as the α anomer binds to duplex DNA or single-stranded RNA in a manner similar to that for the β anomers but with a reversed polarity, oligomers can contain nucleomonomers having this epimer or a domain thereof (Praseuth, D., et al., *Proc Natl Acad Sci* (U.S.A.) (1988) 85:1349–1353; Sun, J. S. et al., *Proc Natl Acad Sci* (1991) 88:6023–6027; Debart, F., et al., *Nucl Acids Res* (1992) 20:1193–1200). α-Anomeric oligomers containing the substituted deazapurines of formulas (1), (2), (23) and (25) described herein represent a class of modified oligomers included in the present invention.

Substitute Linkages

The oligomers of the invention can also contain one or more "substitute linkages" as is generally understood in the art. These "substitute linkages" include phosphorothioate, methylphosphonate, thionomethylphosphonate, phosphorodithioate, riboacetal, 2',5' linkages, alkylphosphonates, morpholino carbamate, morpholino sulfamate, morpholino sulfamide, boranophosphate (—O—P(OCH$_3$)(BH$_3$)—O—), siloxane (—O—Si(X$^4$)(X$^4$)—O—; X$^4$ is alkyl or phenyl) and phosphoramidate (methoxyethylamine and the like), and are synthesized as described in the generally available literature and in references cited herein (Sood, A., et al., *J Am Chem Soc* (1990) 112:9000–9001; WO 91/08213; WO 90/15065; WO 91/15500; Stirchak, E. P. et al., *Nucleic Acid Res* (1989) 17:6129–6141; U.S. Pat. Nos. 5,034,506; 5,142, 047; Hewitt, J. M. et al., *Nucleosides and Nucleotides* (1992) 11:1661–1666). Substitute linkages that can be used in the invention oligomers also include three atom linkages such as sulfone, sulfonamide (—O—SO$_2$—NH—), sulfide (—CH$_2$—S—CH$_2$—), sulfonate (—O—SO$_2$—CH$_2$—), carbamate (—O—C(O)—NH—, —NH—C(O)—O—), 3'-dimethylhydrazino (—CH$_2$—NCH$_3$—NCH$_3$—), 3'-sulfamate (—O—S(O)(O)—N—; —N—S(O)(O)—N—), 3'-thioformacetal (—S—CH$_2$—O—), formacetal (—O—CH$_2$—O—), 3'-amine (—NH—CH$_2$—CH$_2$—), 3'-N-methylhydroxylamine (—CH$_2$—NCH$_3$—O—), disclosed in WO 89/12060, WP 91/15500, PCT/US90/06110 and PCT/US91/06855, which references are incorporated herein by reference.

Suitable four atom linkages include methylene hydrazine (—CH$_2$—NH—NH—CH$_2$—), methylene hydrazone (—CH=N—NH—CH$_2$—), methylene dimethylhydrazine (—CH$_2$—N(CH$_3$)—N(CH$_3$)—CH$_2$—), oxime (—CH=N—O—CH$_2$—), and linkages such as —CH$_2$—N(CH$_3$)—O—CH$_2$— and —CH$_2$—CH$_2$—NH—CH$_2$—, disclosed in WO 92/20822, incorporated herein by reference.

Suitable 2'5' linkages include (such as 2',5' carbamate (2' —N(H)—C(O)—O— 5'), 5',2' carbamate (2' —O—C(O)—N(H)— 5'), 5',2' methylcarbamate (2' —O—C(O)—N(CH$_3$)— 5') and 5',2' thioformacetal (2' —O—CH$_2$—S— 5'), disclosed in U.S. application Ser. No. 07/892,902, described in WO 93/24508. In general, 2',5' linkages will not contain phosphorus.

Linkages are disclosed in U.S. Pat. No. 5,264,562, U.S. application Ser. No. 07/763,130 which disclosure is described in WO 92/05186 and U.S. application Ser. No. 07/806,710, which disclosure is described in WO 93/12135.

Except where specifically indicated, the substitute linkages, such as a formacetal linkage, —O—CH$_2$—O—, are linked to either the 3' or 2' carbon of a nucleomonomer on the left side and to the 5' carbon of a nucleomonomer on the right side. A formacetal linked (3',5') dimer is shown in FIG. 1, formula (6). Thus, a formacetal linkage can be indicated as 3' —O—CH$_2$—O— 5' or 2' —O—CH$_2$—O— 5'. A 2',5' —S—CH$_2$—O— linkage is designated 2'-thioformacetal and a 3',5' —S—CH$_2$—O— linkage is designated 3'-thioformacetal. The designations of a 2', 3' or 5' carbon can be modified accordingly when a structure other than ribose, deoxyribose or arabinose is linked to an adjacent nucleomonomer. Such structures include a hexose, morpholino ring, carbocyclic ring (e.g. cyclopentane) and the like.

Also included are oligomers containing sulfide or sulfone linkages (Benner, S. A., International Publication No. WO 89/12060), sulfamate linkages (International Publication No. WO 91/15500), carbamate linkages in morpholino-linked oligomers (Stirchak, E. P. et al., *Nucleic Acids Res* (1989) 17:6129–6141) and related linkages in morpholino oligomers of the formula (7) shown in FIG. 1 wherein $X^2$ is CO, CS or SO$_2$; $X^3$ is O, S, NH, NCH$_3$, CH$_2$, CF$^2$ or CHF; each Y is independently an oligomer or $R^1$ wherein each $R^1$ is independently H or a blocking group and each B is independently chosen and has the meaning defined herein, provided that at least one B is a base of formula (1) or (2).

Additional linkages are disclosed in U.S. application Ser. Nos. 07/899,736 and 07/894,397, which disclosures are described in WO 93/24507.

Exemplary dimers containing riboacetal and related linkages of formulae (8–15) are shown in FIGS. 2 and 3 wherein for each structure, $R^1$ and B are independently chosen and have the meanings defined herein;

$R^3$ has the meaning as defined herein;

$X^3$ is independently selected from the group consisting of O, S, NH, NCH$_3$, CH$_2$, CF$_2$ and CFH;

$X^4$ is independently selected from the group consisting of O, S, SO, SO$_2$, CH$_2$, CO, CF$_2$, CS, NH and NR$^4$ wherein R$^4$ is lower alkyl (C$_{1-4}$; methyl, ethyl, propyl, isopropyl, butyl or isobutyl);

$X^5$ is selected from the group consisting of O, CO, S, CH$_2$, CS, NH and NR$^4$;

$X^6$ is selected from the group consisting of CH, N, CF, CCl, and CR$^5$ wherein R$^5$ is methyl or lower alkyl (C$_{2-4}$) fluoromethyl, difluoromethyl, trifluoromethyl or lower fluoroalkyl (C$_{2-4}$, F$_{1-5}$);

$X^7$ is selected from the group consisting of O, S, CH$_2$, CO, CF$_2$ and CS, provided that at least one B is of the formula (1) or (2) as defined above; and further provided that no adjacent $X^4$, $X^5$ or $X^7$ are O (i.e., —O—O—, a peroxide).

Compounds of the 5-member ring series are preferred embodiments for oligomers containing one or more riboacetal linkages (formula (8)), where $X^4$ is O and $X^5$, $X^7$ are $CH_2$ and $X^6$ is CH.

Also included are oligomers containing nucleomonomer residues linked via amide bonds. Exemplary linkages have been described (Nielsen, P. E., et al., *Science* (1991) 254:1497–1500. Other suitable substitute linkages are described below.

The use of carbamate, carbonate, sulfide, sulfoxide, sulfone, N-methylhydroxylamine and dimethylhydrazino linkages in synthons or oligomers has been described (Vaseur, J.-J. et al., *J Amer Chem Soc* (1992) 114:4006–4007; WO 89/12060; Musicki, B. et al., *J Org Chem* (1990) 55:4231–4233; Reynolds, R. C., et al., *J Org chem* (1992) 57:2983–2985; Mertes, M. P., et al., *J Med Chem* (1969) 12:154–157; Mungall, W. S., et al., *J Org Chem* (1977) 42:703–706; Stirchak, E. P., et al., *J Org Chem* (1987) 52:4202–4206; Wang, H., et al., *Tet Lett* (1991) 50:7385–7388; International Application No. PCT US91/ 03680). Substitute linkage(s) can be utilized in the oligomers for a number of purposes such as to further facilitate binding with complementary target nucleic acid sequences and/or to increase the stability of the oligomers toward nucleases.

Base

Suitable bases (designated "B" herein) for use within the present invention include the known purine and pyrimidine heterocycles and the invention 7-substituted deazapurines, heterocycle bases which have been modified and tautomers thereof. Such modifications include alkylated purines or pyrimidines, acylated purines or pyrimidines, or other heterocycles. Such "analogous purines" and "analogous pyrimidines" or purine or pyrimidine analogs are those generally known in the art, some of which are used as chemotherapeutic agents. An exemplary, but not exhaustive, list includes $N^4,N^4$-ethanocytosine, 5-(1-propynyl)uracil, 5-(1-propynyl)cytosine, 7-deazaguanosine, 8-oxo-$N^6$-methyladenine, 4-acetylcytosine, 5-(carboxyhydroxylmethyl)uracil, 5-fluorouracil, 5-bromouracil, 5-carboxymethylaminomethyl-2-thiouracil, 5-carboxymethylaminomethyl uracil, dihydrouracil, inosine, $N^6$-isopentenyl-adenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, $N^6$-methyladenine, 7-methylguanine, 5-methylaminomethyl uracil, 5-methoxy aminomethyl-2-thiouracil, 5-methoxyuracil, 2-methylthio-$N^6$-isopentenyladenine, pseudouracil, 5-methyl-2-thiouracil, 2-thiouracil, 4-thiouracil, 5-methyluracil, 2-thiocytosine, and 2,6-diaminopurine. In addition to these base analogs, pyrimidine analogs including 6-azacytosine, 6-azathymidine and 5-trifluoromethyluracil described in Cook, D. P., et al., International Publication No. WO 92/02258 (incorporated herein by reference) can be conveniently incorporated into the invention oligomers.

Preferred bases (B) include those of the formula (1) and (2), adenine, guanine, thymine, uracil, cytosine, 5-methylcytosine, 8-oxo-$N^6$-methyladenine, pseudoisocytosine, 5-(1-propynyl)uracil and 5-(1-propynyl)cytosine.

Synthesis of 7-Deazapurine Nucleomonomers

Synthesis of the 7-deazapurine heterocycles (pyrrolo[2,3-d]pyrimidines) is accomplished by known procedures (Davoll, J., *J. Chem. Soc.* (1960) 131–138; Noell, C. W. and Robins, R. K., *J. Heterocyclic Chem.* (1964) 1:34–41; Seela, F., and Richter, R., *Chem. Ber.* (1978) 111:2925–2930; Seela, F. et al., *Nucleosides Nucleotides* (1987) 6:11–23; and European Patent Publication No. 0 251 786 A2). The nucleomonomers of the present invention are conveniently prepared from intermediates containing a bromo, iodo or triflouromethane sulfonyl moiety at the 7-position. Substituents at the 7-position can be introduced at the free heterocycle level (Pudlo, J. S. et al., *J. Med. Chem.* (1990) 33:1984–1992) or after glycosylation (or alkylation) of the heterocycle. The appropriate 7-deazapurine heterocycle (6 or 7, FIG. 4-1) or the like is most conveniently glycosylated (or alkylated) by the sodium salt procedure (Kazimierczuk, Z. et al., *J. Am. Chem. Soc.* (1984) 106:6379–6382; Cottam, H. B. et al., *J. Med. Chem.* (1985) 28:1461–1467; Ramasamy, K. et al., *Tetrahedron Letters* (1987) 28:5107–5110); and Hoffer, M. *Chem. Ber.* (1960) 93:2777–2781) (FIG. 4-2). These intermediates are conveniently converted to the 7-iodo, 7-bromo or 7-triflouromethane sulfonyl derivative by known procedures. Depending on the additional nucleomonomer modifications to be utilized the 7-substituent is incorporated at various steps of the synthetic scheme as described herein. Upon conversion of the nucleomonomer to the desired $R^8$ and $R^9$ substituent (Seela, F., et al., *Liebigs Ann. Chem.* (1987) 15–19; Townsend, L. B., et al., *J. Heterocyclic Chem.* (1976) 13:1363–1364; and Davoll, J., *J. Chem. Soc.* (1960) 131–138) the nucleomonomers are converted to blocked nucleomonomers suitable for incorporation into oligomers by conventional methods.

Figure 9:
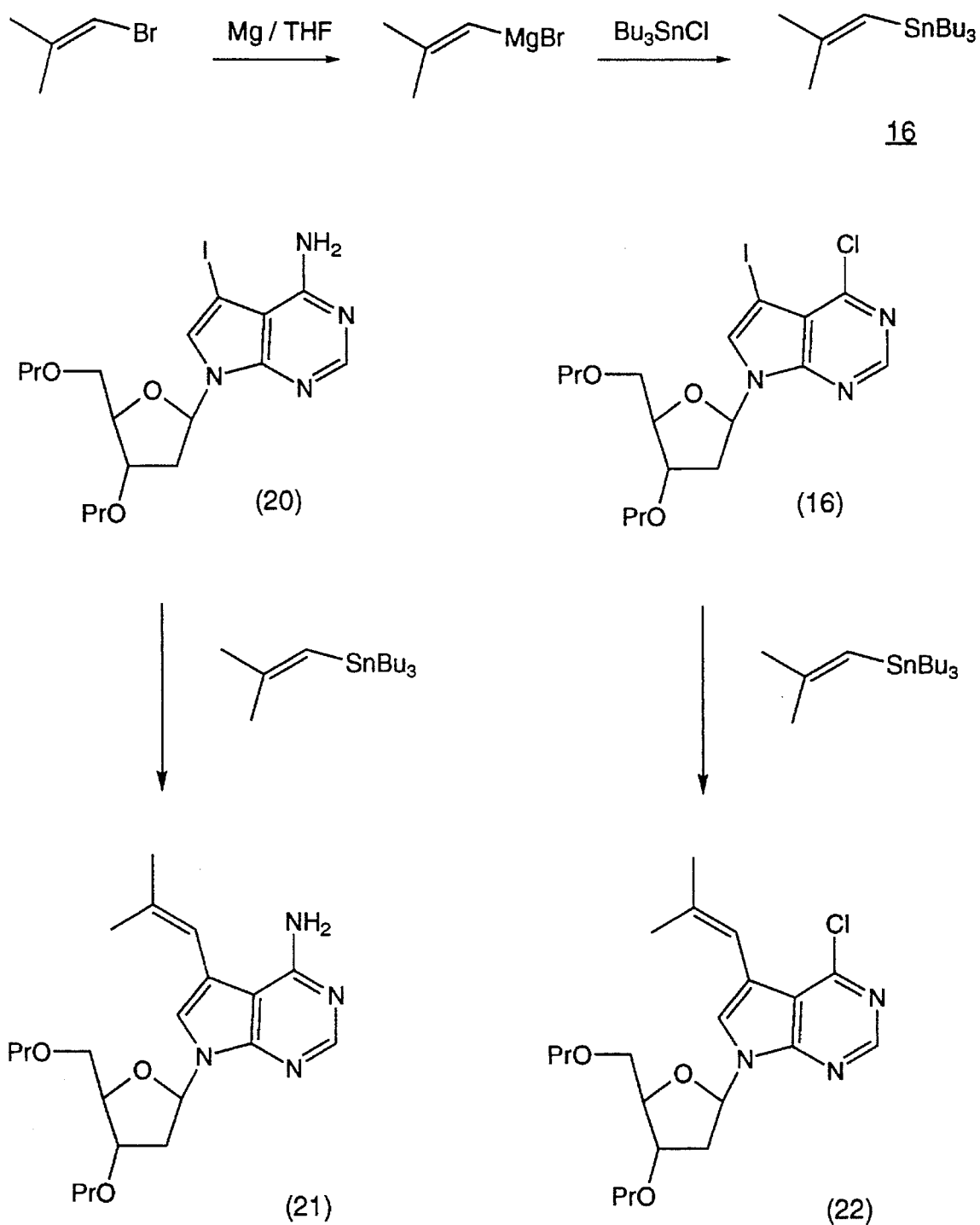
FIG. 9. Synthesis of 7-(2-methyl-1-propenyl) substituted deazapurine nucleomonomers.

The substituents at the 7-position are incorporated by known chemistry. Most conveniently the substituents of the present invention are introduced via a palladium catalyzed reaction (Hobbs, F. W., *J. Org. Chem.* (1989) 54:3420–3422; Robins, M. J. et al., *Tetrahedron Letters* (1990) 31:3731–3734; and Cocuzza, A. J., *Tetrahedron Letters* (1988) 29:4061–4064). Alkyl stannanes, alkenyl stannanes and heteroaryl stannanes are most conveniently employed to introduce many of the substituents of the present invention (Edstrom, E. D. et al., *J. Org. Chem.* (1993) 58:403–407; Badone, D. et al., *J. Org. Chem.* (1992) 57:6321–6323; Scott, W. J. et al., *J. Am. Chem. Soc.* (1986) 108:3033–3040; Malm, J. et al., *Tetrahedron Letters* (1992) 33:2199–2202; Farina, V. et al., *Synlett* (1991) 157–159; Crisp, G. T., *Synthetic Communications* (1989) 19:2117–2123; Crisp, G. T. et al., *Synthetic Communications* (1990) 20:413–422; Mamos, P. et al., *Tetrahedron Letters* (1992) 33:2413–2416) (FIG. 9). Methyl and ethyl substituents are readily introduced via lithium anion chemistry (Pudlo, J. S. et al., *J. Med. Chem.* (1990) 33:1984–1992) or via palladium chemistry (Mamos, P. et al., *Tetrahedron Letters* (1992) 33:2413–2416). Substituents such as cyano are prepared by known procedures (Tolman, R. L., et al., *J. Am. Chem. Soc.* (1969) 93:2102–2108). The substituted ethynes are readily introduced via the desired ethyne (Hobbs, F. W., *J. Org. Chem.* (1989) 54:3420–3422; Robins, M. J. et al., *Tetrahedron Letters* (1990) 31:3731–3734).

Synthesis of Alkenyl Stannanes, Heteroaryl Stannanes and Ethynyl Heteroaryl Moieties Alkenyl stannanes are conveniently prepared by known procedures (Leusink, A. J., et al., *J. Organometal. Chem.* (1967) 9:285–294; Saihi, M. L. and Pereyre, M. *Bull. Soc. Chim.* (1977) 1251–1255; and Eaborn, C. and Waters, J. A. *J. Chem. Soc.* (1962) 1131–1132) (Example 8, FIG. 9).

Figure 14:
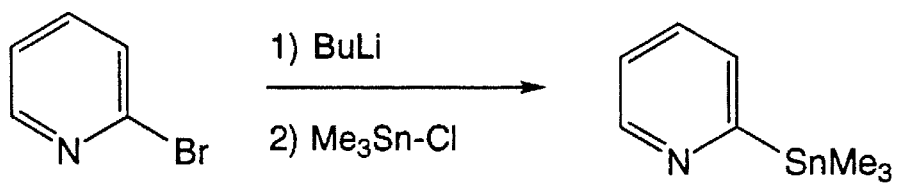
FIG. 14. Synthesis of heteroaryl precursors.
Figure 14:
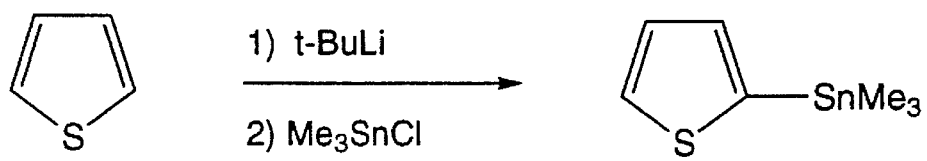
Figure 14:
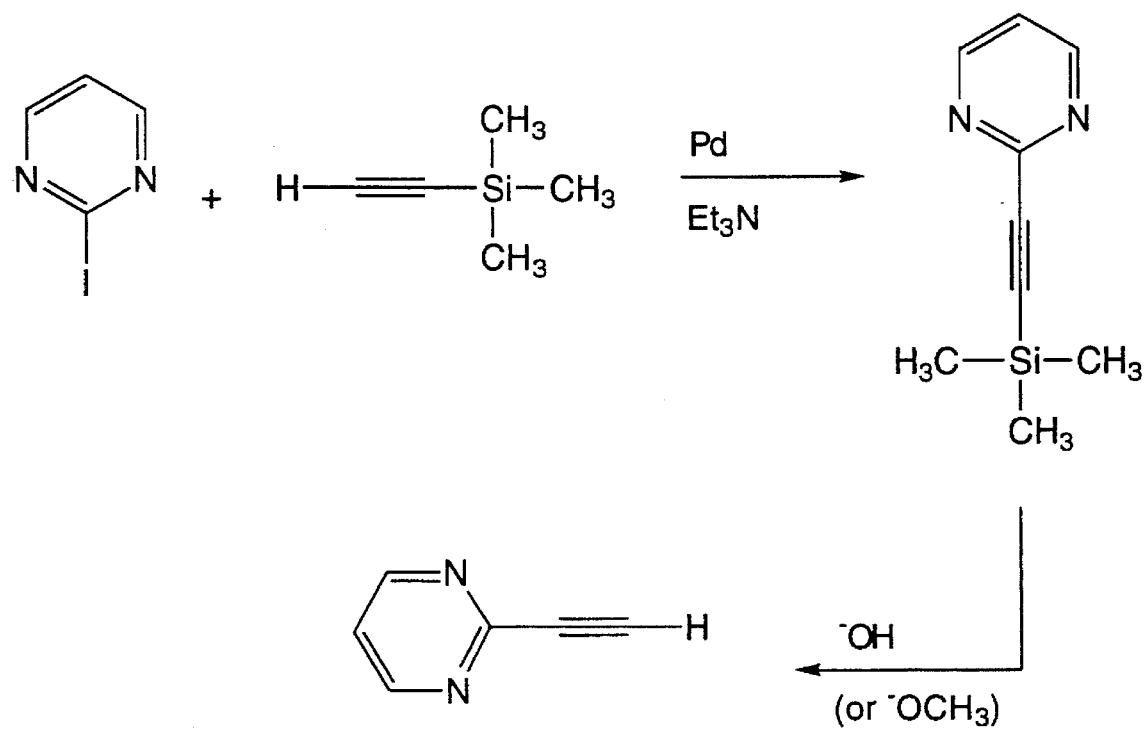

Synthesis of heteroaryl stannanes is conveniently accomplished as described (Bailey, T. R. *Tet Lett* (1986) 27:4407–4410; Jutzi, P. et al., *J. Organometal Chem.* (1983) 246:163–168; Molloy, K. C. et al., *J. Organometal Chem.* (1989) 365:61–73) (FIG. 14).

Ethynyl heteroaryl derivatives are prepared from ethynyltrimethylsilane and an appropriate heteroaryl as described (Austin, W. B., et al., *J. Org. Chem.* (1981) 46:2280–2286) (FIG. 14).

Synthesis of Tricyclic and Tetracyclic Nucleosides of the Structural Formula (4), (24) and (26)

Figure 15:
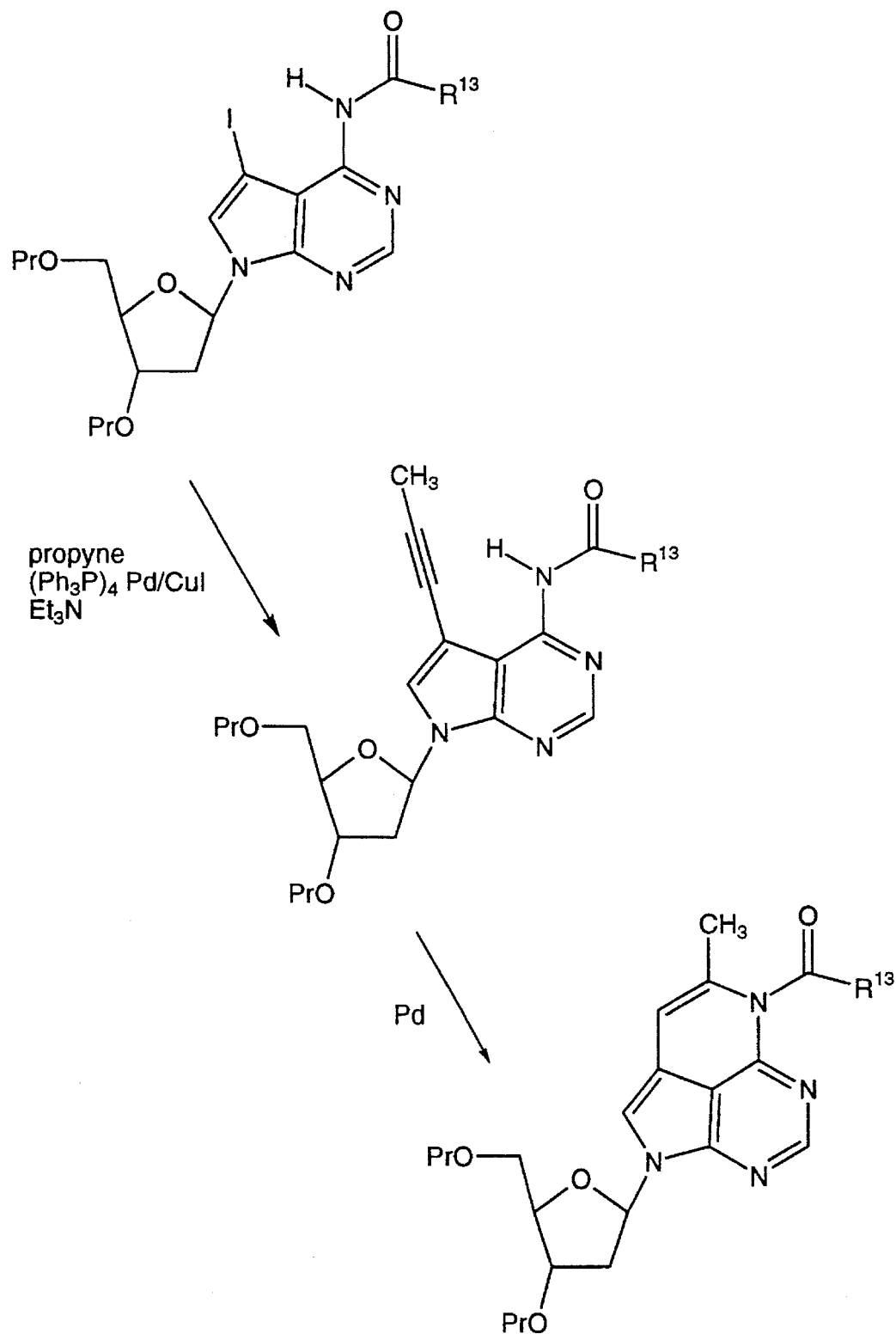
FIG. 15. Synthesis of tricyclic deazapurine nucleomonomers.

Tricyclic nucleomonomers are conveniently prepared from the corresponding 7-ethynyl-6-N-acyl (or carbamoyl) protected 7-deazaadenosine derivative. Cyclization of this intermediate leads to the desired tricycle (FIG. 15). This cyclization reaction can be performed with or without a nitrogen acyl protecting group and is palladium mediated (Rudisill, D. E. et al., *J. Org. Chem.* (1989) 54:5856–5866; Iritani, K. et al., *Tetrahedron Letters* (1988) 29:1799–1802; Arcadi, A. et al., *Tetrahedron Letters* (1989) 30:2581–2584 and Larock, R. C. et al., *J. Am. Chem. Soc.* (1991) 113:6689–6690).

Tetracyclic nucleomonomers, (24) and (26), are conveniently prepared from the corresponding 7-iodo-6-chloro-7-deazaadenosine and the corresponding t-BOC protected aminoarylstannane (Muchowski, J. M. et al., *J. Org. Chem.* (1980) 45:4798–4801; Salituro, F. G. et al., *J. Org. Chem.* (1988) 53:6138–6139; and Turner, J. A., *J. Org. Chem.* (1983) 48:3401–3408). Palladium mediated coupling at the 7-position followed by cyclization, with removal of HCl, leads to the tetracycle (FIG. 16).

Synthesis of Oligomers

Oligomers or the segments thereof are conventionally synthesized. The synthetic methods known in the art and described herein can be used to synthesize oligomers containing bases of the invention, as well as other bases known in the art, using appropriately protected nucleomonomers (see FIG. 12). Methods for the synthesis of oligomers are found, for example, in Froehler, B., et al., *Nucleic Acids Res* (1986) 14:5399–5467; *Nucleic Acids Res* (1988) 16:4831–4839; *Nucleosides and Nucleotides* (1987) 6:287–291; Froehler, B., *Tetrahedron Letters* (1986) 27:5575–5578; Caruthers, M. H. in *Oligodeoxynucleotides-Antisense Inhibitions of Gene Expression* (1989), J. S. Cohen, editor, CRC Press, Boca Raton, p7–24; Reese, C. B. et al., *Tetrahedron Letters* (1985) 26:2245–2248. Synthesis of the methylphosphonate linked oligomers via methyl phosphonamidite chemistry has also been described (Agrawal, S. et al., *Tetrahedron Letters* (1987) 28:3539–3542; Klem, R. E., et al., International Publication Number WO 92/07864).

Oligomers of the invention containing bases of formula (1) or (2) and one or more substitute linkages can be synthesized by one of four general methods according to the reaction conditions required for synthesis of a given substitute linkage. In the first method (#1), nucleomonomers containing bases of formula (1) or (2) are directly incorporated into oligomers or a convenient fragment thereof using standard synthesis conditions and reagents. Exemplary linkages that can be made by method #1 include phosphodiester, phosphorothioate, phosphoroamidate, methylphosphonate, phosphorodithioate, carbonate, morpholino carbamate and sulfonate.

Method #2 involves synthesis of short synthons (dimers, trimers, etc) starting with an appropriate precursor such as a 7-bromo or 7-iodo precursor (as described below) which is subsequently converted to the C-7 substituent of formula (1) or (2) and a synthon suitable for incorporation into oligomers. This approach is exemplified in FIGS. 7, 8 and 11 and is suitable for synthesis of linkages including N-methylhydroxylamine, dimethylhydrazo, sulfamate, carbamate, sulfonate, sulfonamide, formacetal thioformacetal and carbonate.

Synthesis method #3 starts with the deazapurine (unprotected or N-protected) nucleomonomers which is subsequently iodinated. Introduction of the $R^2$ group at the 7-position is accomplished within the synthetic route to the desired dimer or trimer synthon. Method #3 is suitable for synthesis of linkages including N-methylhydroxylamine, dimethylhydrazino, sulfamate, formacetal, thioformacetal, riboacetal, sulfonate, sulfonamide, carbamate, carbonate and boranophosphate linkages.

Figure 13:
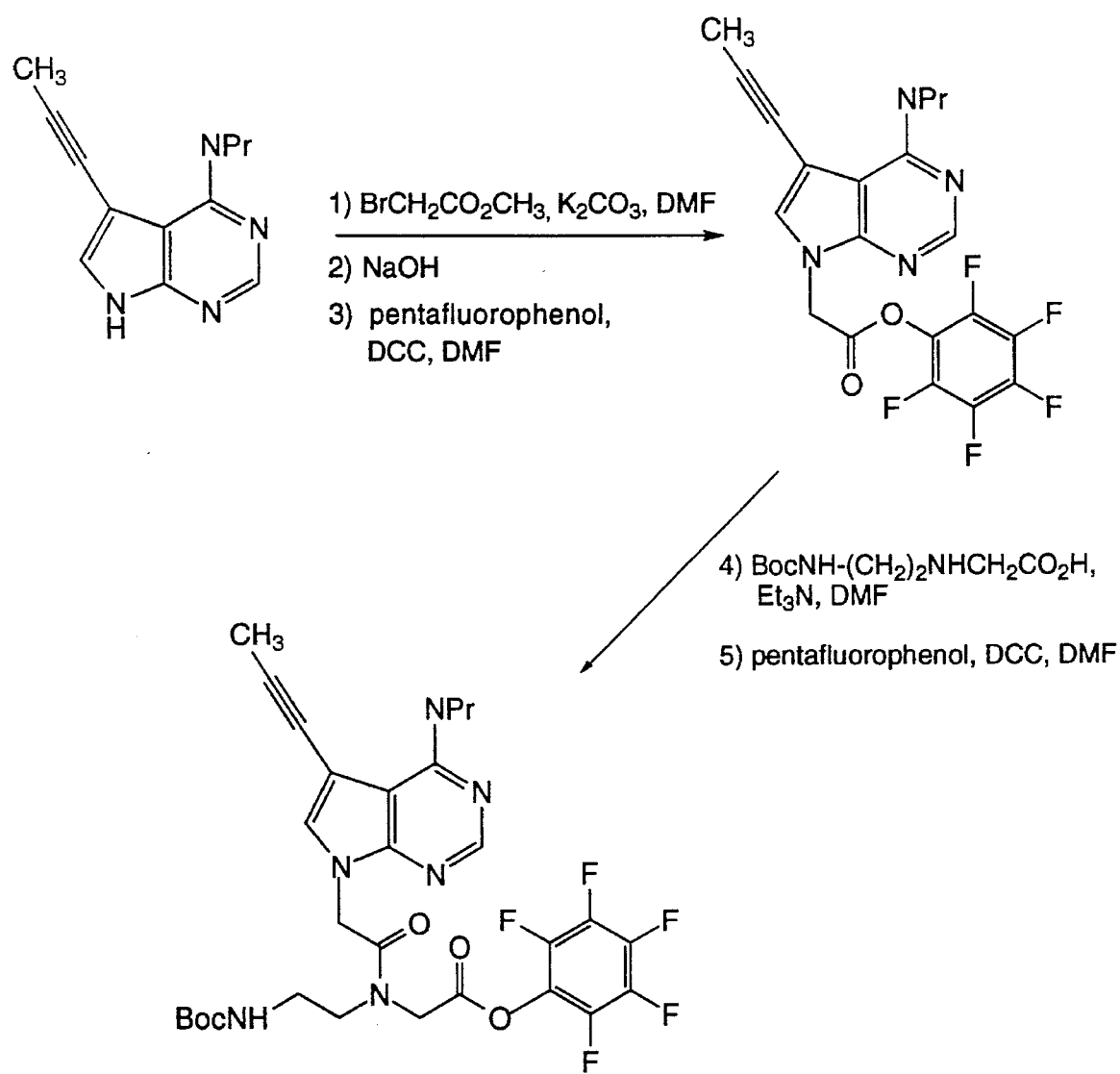
FIG. 13. Synthesis of a monomer for an oligomer containing amide linkages (method #4).

Method #4 starts with either (i) the deazapurine base containing $R^2$, followed by conversion to a nucleomonomer suitable for incorporation into oligomers (e.g. amide linkages) as exemplified in FIG. 13 or (ii) a suitable precursor such as 7-iodo deazapurine or the deazapurine which is glycosylated or alkylated followed by conversion of the nucleomonomer to a derivative containing $R^2$ and converted to the desired synthon (e.g. linkages such as sulfide, sulfoxide or sulfonate).

In general, reaction conditions that are needed to synthesize a particular dimer, trimer or larger synthon and may not be compatible with an $R^2$ alkynyl or alkenyl substituent at the 7-position are (1) electrophilic addition reactions, or conditions that could promote electrophilic addition to C—C multiple bonds (e.g. HCl, HF, $BF_3$, $Cl_2$ or $Br_2$); (2) conditions that could promote reduction of C—C multiple bonds (e.g., hydrogenation via $H_2$/Pd/C or hydrides such as $B_2H_6$, $BH_3$·complex or as a class, tin hydrides or aluminum hydrides); (3) conditions that promote free radical reactions (e.g., $Cl_2$\hv, peroxides or AIBN); and (4) reaction conditions that promote oxidation of C—C multiple bonds (e.g. $KMnO_4$, $OsO_4$, alkyl carboxylic peracids). Synthetic schemes involving these reaction conditions may prevent the use of Method #1.

In general, reaction conditions that are required to synthesize certain oligomers that may not be compatible with 7-iodo deazapurines, or the like, are (1) conditions that promote reduction of aryl iodides (e.g., $H_2$ or hydrides), (2) alkylation and arylation reactions mediated by organometallic reagents or (3) reactions that promote free radical reactions (e.g., $Cl_2$\hv, peroxides or AIBN). Synthetic schemes involving these reactions may prevent use of Method #2.

Method #3 starts with the 7-deazapurine nucleomonomer and the nucleomonomer is subsequently converted to the 7-iodo (or 7-bromo or 7-triflate) derivative at the desired step, followed by conversion to a $R^2$ substituent at desired step.

Additional exemplary linkages that can be synthesized by these general methods are summarized in Table A below.

TABLE A

| Linkage Structure* | Method | Reference** |
|---|---|---|
| 2' —S—$CH_2$— 5' | 1–4 | 1 |
| 3' —S—$CH_2$— 5' | 1–4 | 2 |
| 2' —S(O)—$CH_2$— 5' | 1–4 | 1 |

TABLE A-continued

| Linkage Structure* | Method | Reference** |
|---|---|---|
| 3' —S(O)—CH$_2$— 5' | 1–4 | 1 |
| 2' —S(O)(O)—CH$_2$— 5' | 1–4 | 1 |
| 3' —S(O)(O)—CH$_2$— 5' | 1–4 | 1 |
| 2' —CH$_2$—S— 5' | 3, 4 | 1 |
| 3' —CH$_2$—S— 5' | 3, 4 | 2 |
| 2' —CH$_2$—S(O)— 5' | 3, 4 | 1 |
| 3' —CH$_2$—S(O)— 5' | 3, 4 | 2 |
| 2' —CH$_2$—S(O)(O)— 5' | 3, 4 | 1 |
| 3' —CH$_2$—S(O)(O)— 5' | 3, 4 | 2 |
| 2' —CH$_2$—CH$_2$—O— 5' | 3, 4 | 1 |
| 3' —CH$_2$—CH$_2$—O— 5' | 3, 4 | 2 |
| 2' —N(C(O)(OR$^A$))—CH$_2$—CH$_2$— 5' | 3, 4 | 1 |
| 3' —N(C(O)(OR$^A$))—CH$_2$—CH$_2$— 5' | 3, 4 | 2 |
| 2' —S—CH$_2$—CH$_2$— 5' | 3, 4 | 1 |
| 3' —S—CH$_2$—CH$_2$— 5' | 3, 4 | 2 |
| 2' —NH—C(O)—O— 5' | 3, 4 | 1 |
| 2' —O—CH$_2$—S— 5' | 2–4 | 1 |
| 2' —O—C(O)—N(R$^B$)— 5' | 2–4 | 1 |
| 5' morpholino N—CH$_2$— 5' | 1–4 | 2 |
| 3' —X—C((CH$_2$)$_2$NR$^C$(CH$_2$)$_2$)—X— 5' | 2–4 | 3 |
| 3' —X—C((CH$_2$)$_2$O(CH$_2$)$_2$)—X— 5' | 2–4 | 3 |
| 3' —X—C((CH$_2$)$_2$S(O)(O)(CH$_2$)$_2$))—X— 5' | 2–4 | 3 |
| 3' —X—C((CH$_2$)$_2$S(O)(CH$_2$)$_2$))—X— 5' | 2–4 | 3 |
| 3' —X—C((CH$_2$N(R$^C$)(CH$_2$)$_2$)—X— 5' | 2–4 | 3 |
| 3' —X—C((CH$_2$N(R$^C$)(CH$_2$N(R$^C$))—X— 5' | 2–4 | 3 |

$R^A = C_{1-6}$ alkyl, e.g. CH$_2$CH$_3$ or (CH$_2$)$_5$CH$_3$;
$R^B$ = H or $C_{1-6}$ alkyl, e.g. CH$_3$;
X = O or S;
$R^C = C_{1-6}$ alkyl, CN or $C_{1-6}$ haloalkyl, e.g. CF$_3$; the linkages indicate covalent attachment of the indicated atom with either a 2', 3' or 5' carbon of ribose or deoxyribose.
**1 — Synthesis is accomplished essentially as described in PCT/US91/06855 for equivalent 3', 5' linkages.
2 — International Application Number PCT/US91/06855.
3 — International Application Number PCT/US90/06110;
linkages having a structure such as C((CH$_2$)$_2$(CH$_2$)$_2$O) are cyclic ketals.

Figures 1, 17:
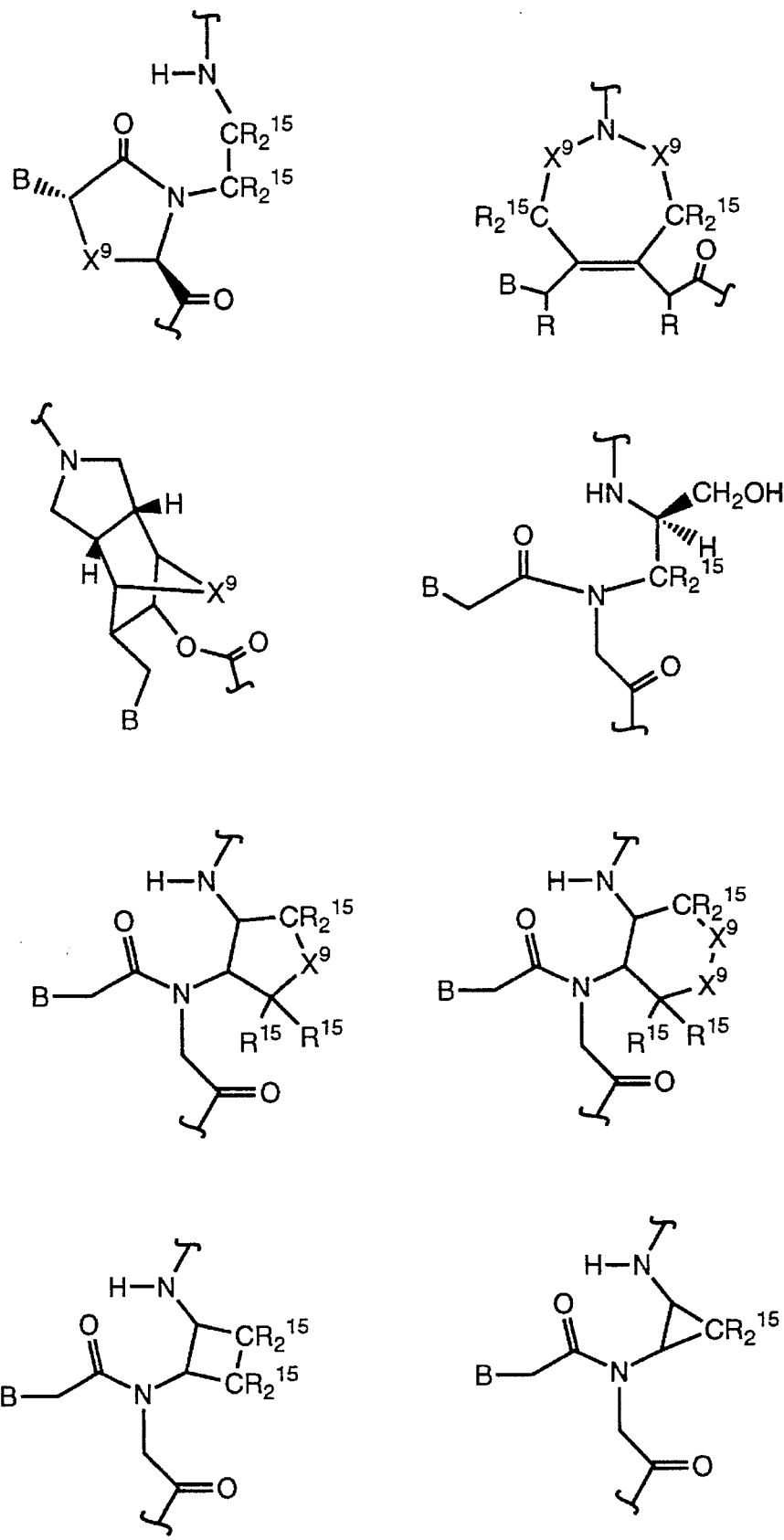
Figures 2, 17:
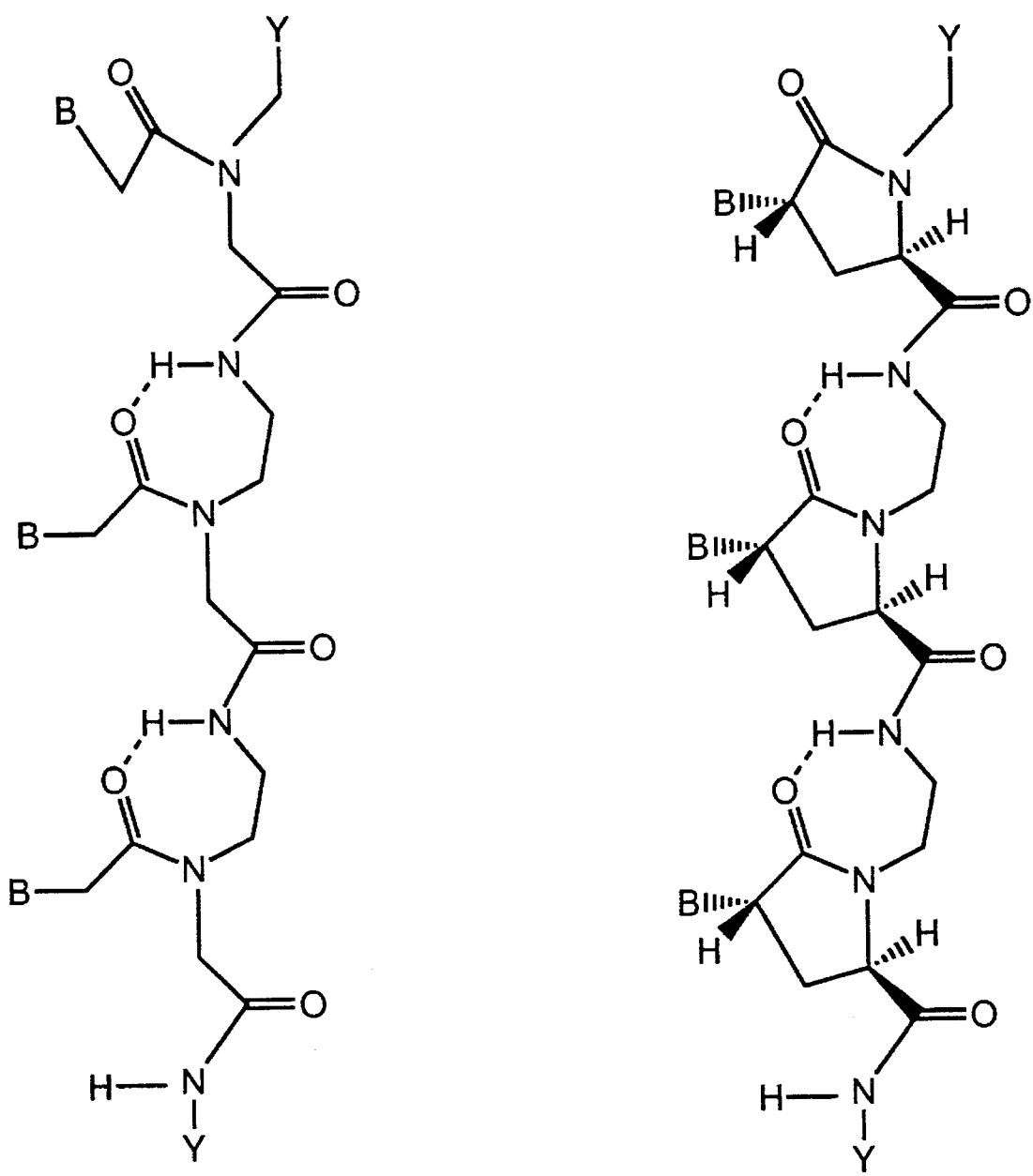
Figures 3, 17:
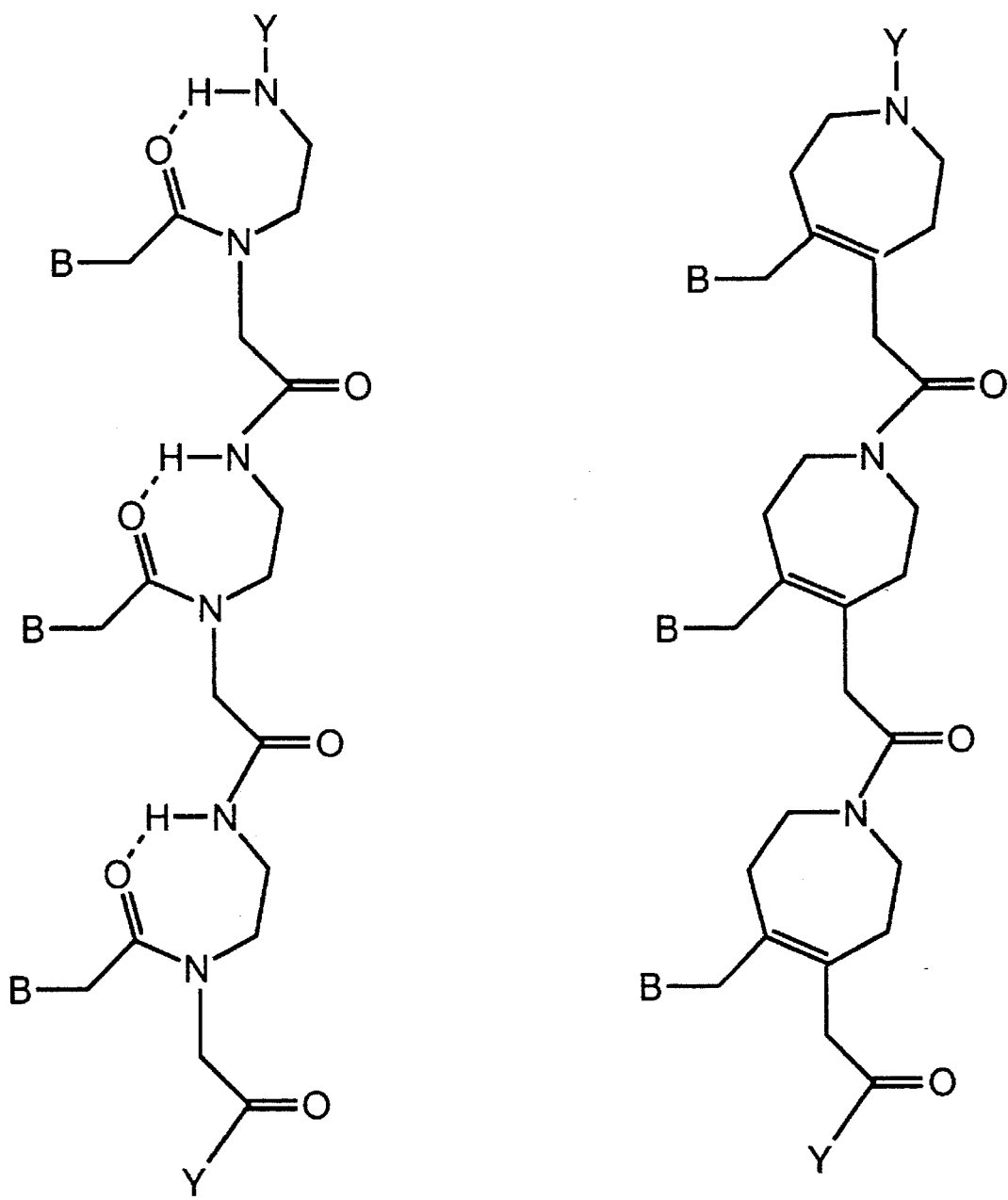
Figure 18:
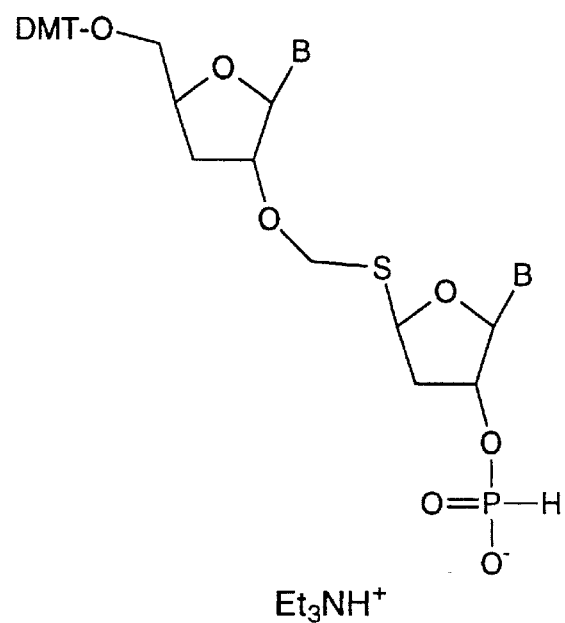
FIG. 18. Dimers synthons containing bases of the invention and having exemplary 2',5' linkages; thioformacetal and carbamate linkages.
Figure 18:
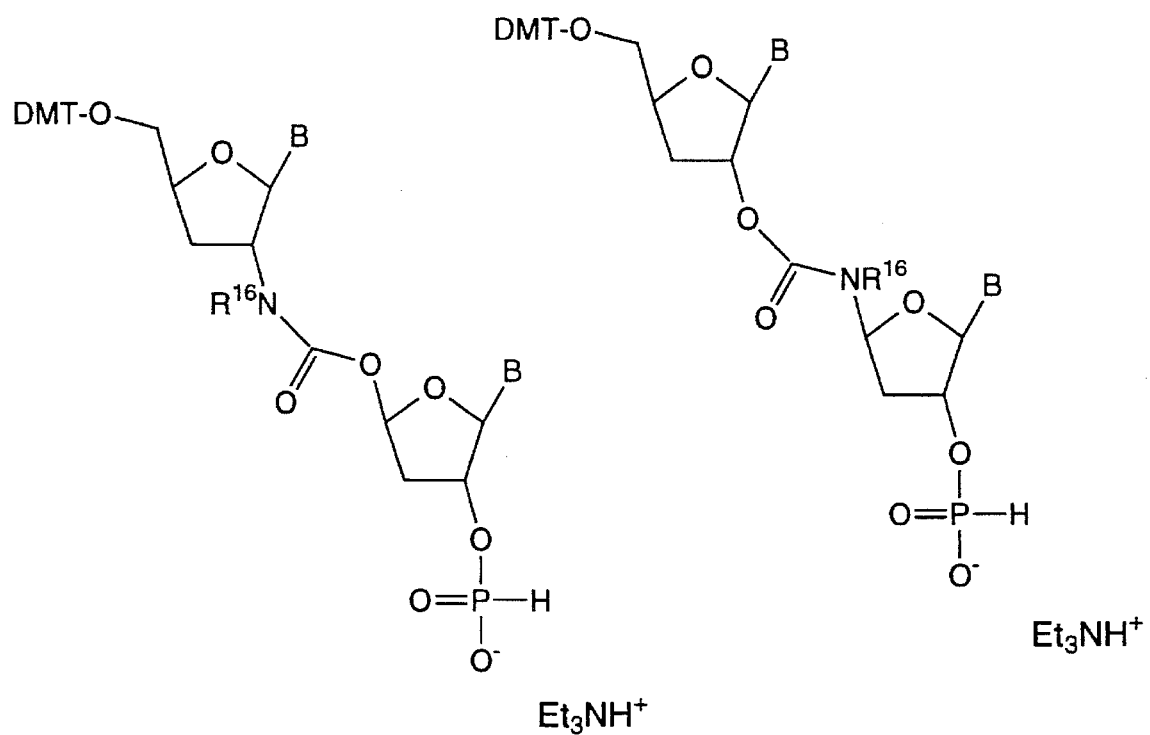

In addition to the substitute linkages given in Table A, FIG. 17 shows a series of repeating nucleomonomer units (17-1) and exemplary amide linked oligomers (17-2, 17-3) containing selected repeating units that can contain the base analogs of the invention. In FIG. 17-1, $X^9$ is S, O, SO, SO$_2$, CH$_2$, CHF, CF$_2$ or NR$^{12}$ and R$^{15}$ is (independently) H, F, OH, OCH$_3$, CH$_3$, or CH-lower alkyl provided that adjacent $X^9$ are not both O. In FIGS. 17-2 and 17-3, each Y is independently selected and has the meaning described above (e.g. Y is H, an oligomer, a blocking group such as FMOC, tBOC, OH, DMT, MMT or an coupling group suitable for oligomer synthesis). Nucleomonomers required to synthesize oligomers containing such linkages are synthesized by method #4.

Oligomers of the invention can be synthesized by any suitable chemistry including amidite, triester or hydrogen phosphonate coupling methods and conditions. The oligomers are preferably synthesized from appropriate starting synthons such as nucleomonomers of formula (3) or (4) wherein R$^1$ at the 5'-position is DMT, MMT, FMOC (9-fluorenylmethoxycarbonyl), PACO (phenoxyacetyl), a silyl ether such as TBDMS (t-butyldiphenylsilyl) or TMS (trimethylsilyl) and R$^1$ at the 3'-position is an ester, H-phosphonate, an amidite such as β-cyanoethylphosphoramidite, a silyl ether such as TBDMS or TMS or t-butyldiphenyl. Alternatively, appropriately protected deazapurine precursors can be conveniently incorporated into short oligomers such as dimer, trimer, tetramer, pentamer or longer synthons that are subsequently derivatized to yield R$^2$ at the 7-position and then incorporated into suitable synthons and longer oligomers.

Synthesis of oligomers containing about 4 or more nucleomonomer residues is preferably accomplished using synthons such as monomers, dimers or trimers that carry a coupling group suitable for use with amidite, H-phosphonate or triester chemistries. The synthon can be used to link the oligomer via a phosphodiester or phosphorous-containing substitute linkage (phosphorothioate, methylphosphonate, thionomethylphosphonate, phosphoramidate and the like).

Synthesis of other nonphosphorous-containing substituted linkages can be accomplished using appropriate precursors as described herein (FIGS. 7 and 8) and are known in the art.

In addition to employing these very convenient and now most commonly used, solid phase synthesis techniques, oligomers can also be synthesized using solution phase methods such as triester synthesis. These methods are workable, but in general, less efficient for oligomers of any substantial length.

Intermediates or starting materials

In other aspects, the invention is directed to intermediates in the synthesis of the oligomers of the invention, including nucleomonomer analogs of formula (3) or (4):

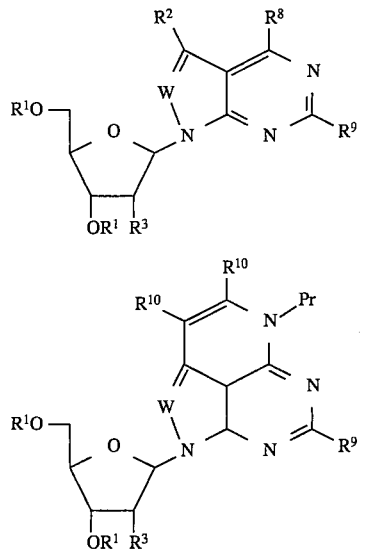

wherein each $R^1$ is independently H or a blocking group;

W, $R^2$, $R^8$, $R^9$ and $R^{10}$ are as defined above;

$R^3$ is independently in the ribo or arabino configuration and is selected from the group consisting of H, OH, F, $NH_2$, OR or SR, wherein OR is O-allyl (—O—$CH_2$—CH=$CH_2$) or SR is S-allyl or O or S alkyl ($C_{1-3}$), wherein alkyl including methyl, ethyl and propyl); and Pr is H or a protecting group;

with the proviso that when W is CH and $R^9$ is H and $R^8$ is $NH_2$ then $R^2$ is not H, or when W is CH and $R^9$ is $NH_2$ and $R^8$ is OH then $R^2$ is not H.

Suitable protecting groups (Pr) include benzoyl, FMOC and tBOC, and suitable $R^1$ groups including DMT, MMT, FMOC, a phosphoramidite such as β-cyanoethylphosphoramidite, hydrogen-phosphonate and methylphosphonamidite.

Preferred protected nucleomonomers are nucleomonomers of formulas (3) and (4) where W is CH, $R^1$ at the 5'-position is DMT, MMT or FMOC; $R^1$ at the 3'-position is N,N-diisopropylamino-β-cyanoethoxyphosphine, N,N-diisopropylaminomethoxyphosphine or hydrogen phosphonate; and $R^2$ is methyl, 1-propynyl or 2-methyl-1-propenyl. For nucleomonomers of formula (4), preferred $R^{10}$ is H, methyl or 1-propynyl. Other preferred nucleomonomers of formula (4) are those where the base is of formulas (23) or (25) and Q is independently CH or N.

Oligomer Embodiments:

One embodiment of oligomers of the present invention can be represented by the formula (5):

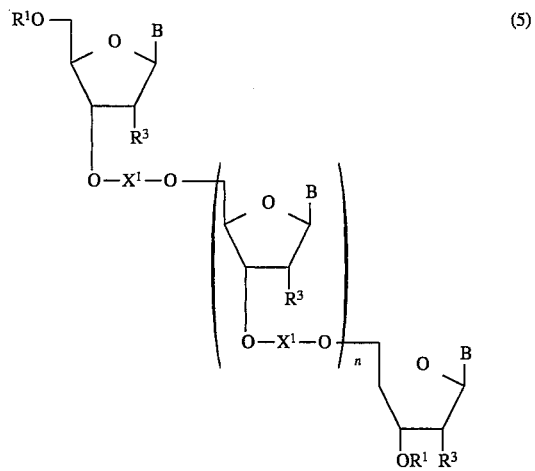

wherein each B is independently a base provided that at least one B is a base of formula (1) or (2) wherein $R^1$, $R^2$, $R^3$ and $R^{10}$ are independently selected and have the meanings defined above;

n is an integer from 0 to 98 (values of 0 to 28 are preferred); and each $X^1$ is independently —P(S)(O)—, —P(O)(O)— or —P(CH$_3$)(O)—, —P(CH$_3$)(S)—, provided that at least one B is of the formula (1) or (2) as defined above; and further provided that when W is CH, $R^2$ is H, $R^8$ is $NH_2$ and $R^9$ is H, or when W is CH, $R^2$ is H, $R^8$ is OH and $R^9$ is $NH_2$, then the remainder of the nucleomonomers comprising said oligomer are not solely comprised of phosphodiester linked 2'-deoxyadenosine, 2'-deoxyguanosine, 2'-deoxycytidine, thymidine or a combination thereof.

Methylphosphonate, thionomethylphosphonate or phosphorothioate substitute linkages enhance the nuclease stability of the oligomers while their negative impact on oligomer affinity for target nucleic acids is compensated by the inclusion of the 7-substituted deazapurines of the invention or other affinity enhancing bases such as 5-(1-propynyl)-uracil or 5-(1-propynyl)-cytosine.

The most preferred $R^2$ group is methyl, 1-propynyl or 2-methyl-1-propenyl. Preferred $R^3$ groups are H, OH, F and O-allyl. Preferred $R^{10}$ groups are H, methyl, 1-propynyl and a carbocyclic ring.

Other preferred oligomers of the invention contain substitute linkages other than phosphodiester, phosphorothioate, thionomethylphosphonate or methylphosphonate. Particularly useful forms of these substitute linkages include riboacetal, formacetal and 3'-thioformacetal linkages, with 3'-thioformacetal being most preferred.

For synthesis of oligomers containing formacetal-type substitute linkages, in lieu of at least one phosphodiester linkage, dimeric synthons of the formula (6) shown in FIG. 1, wherein the substituents B, X, $R^1$ and $R^3$ are as defined above are particularly useful.

Figure 7:
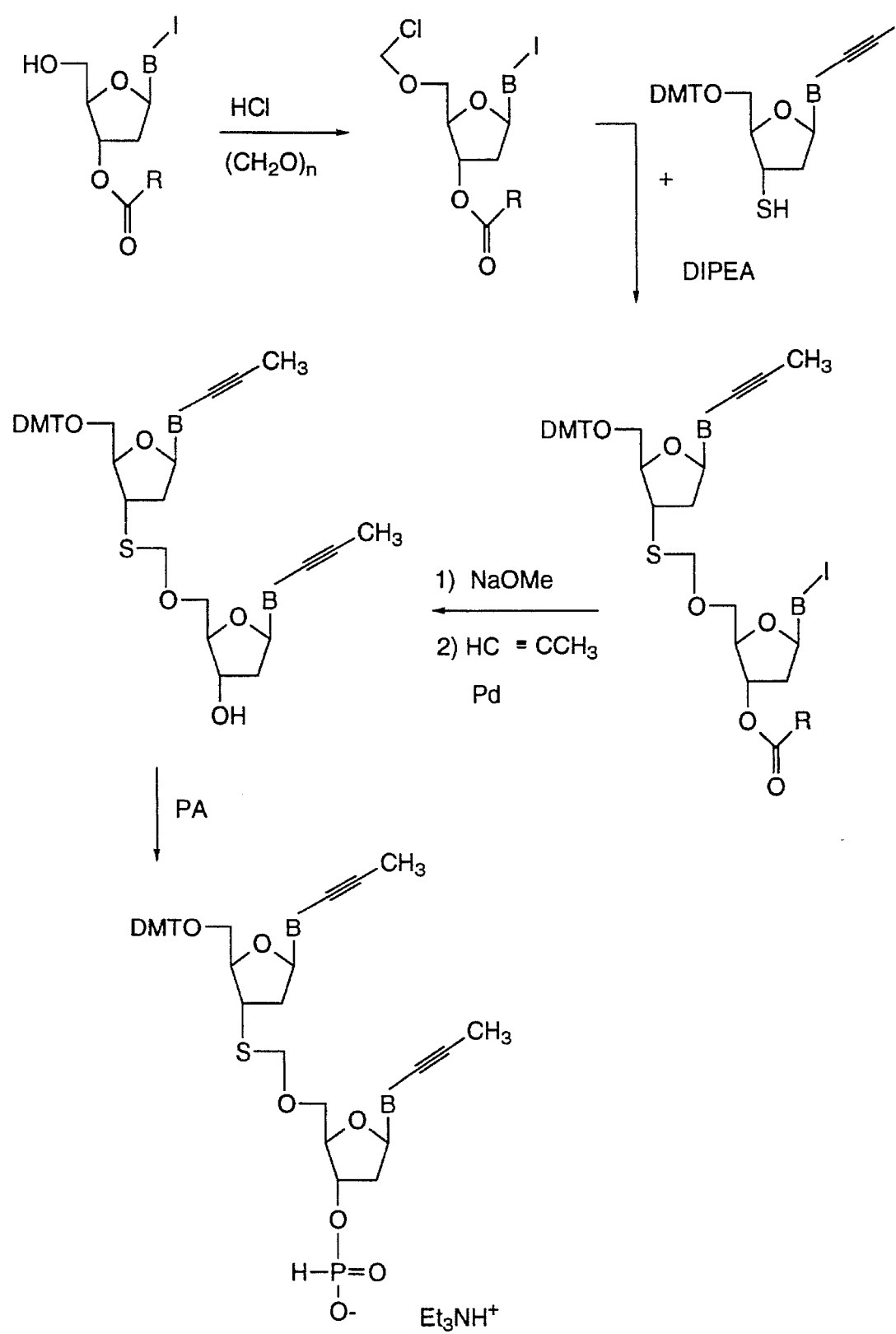
FIG. 7. Synthesis of dimer linked by a 3'-thioformacetal linkage (method #2).
Figures 1, 8:
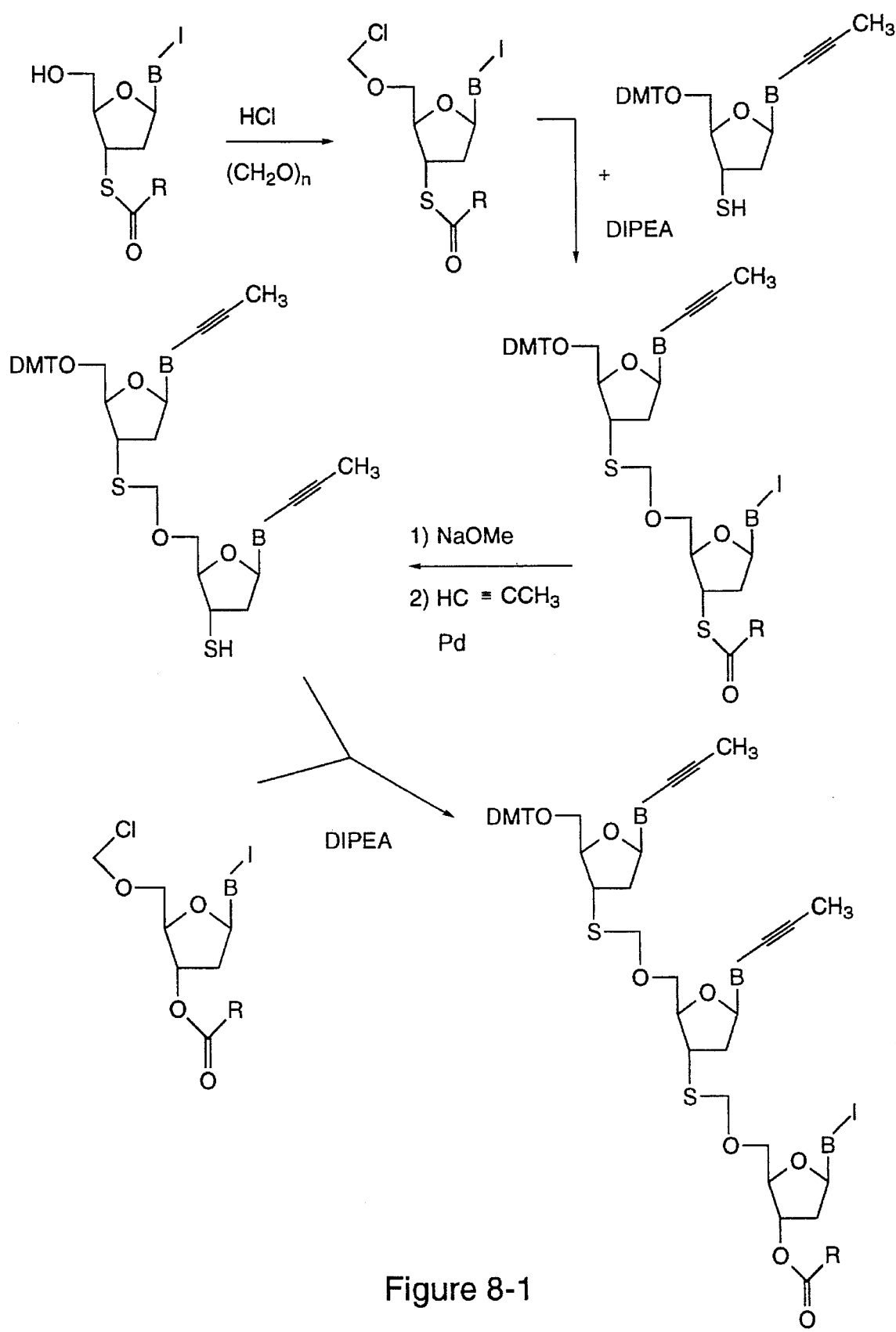
Figures 2, 8:
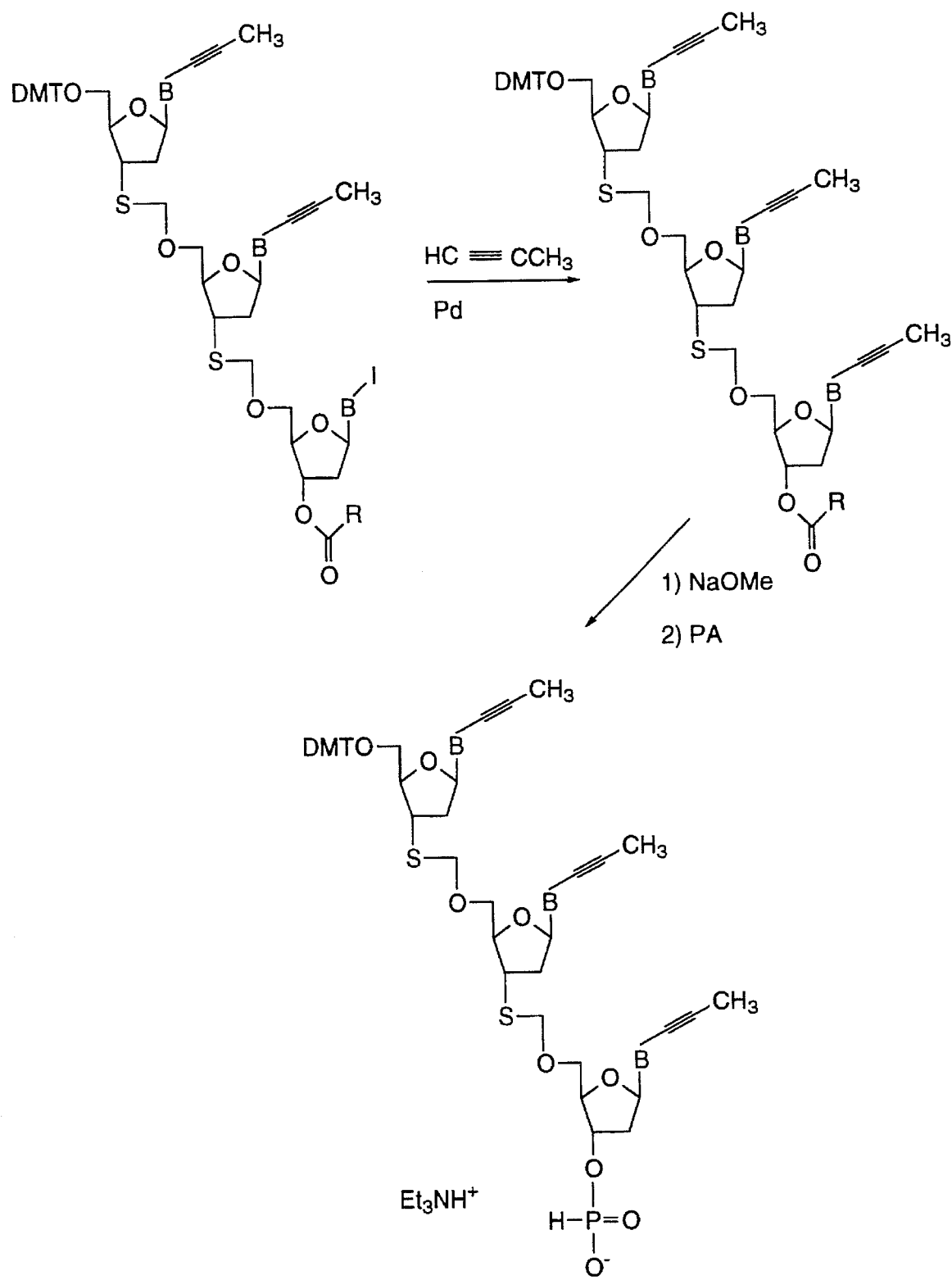
Figure 11:
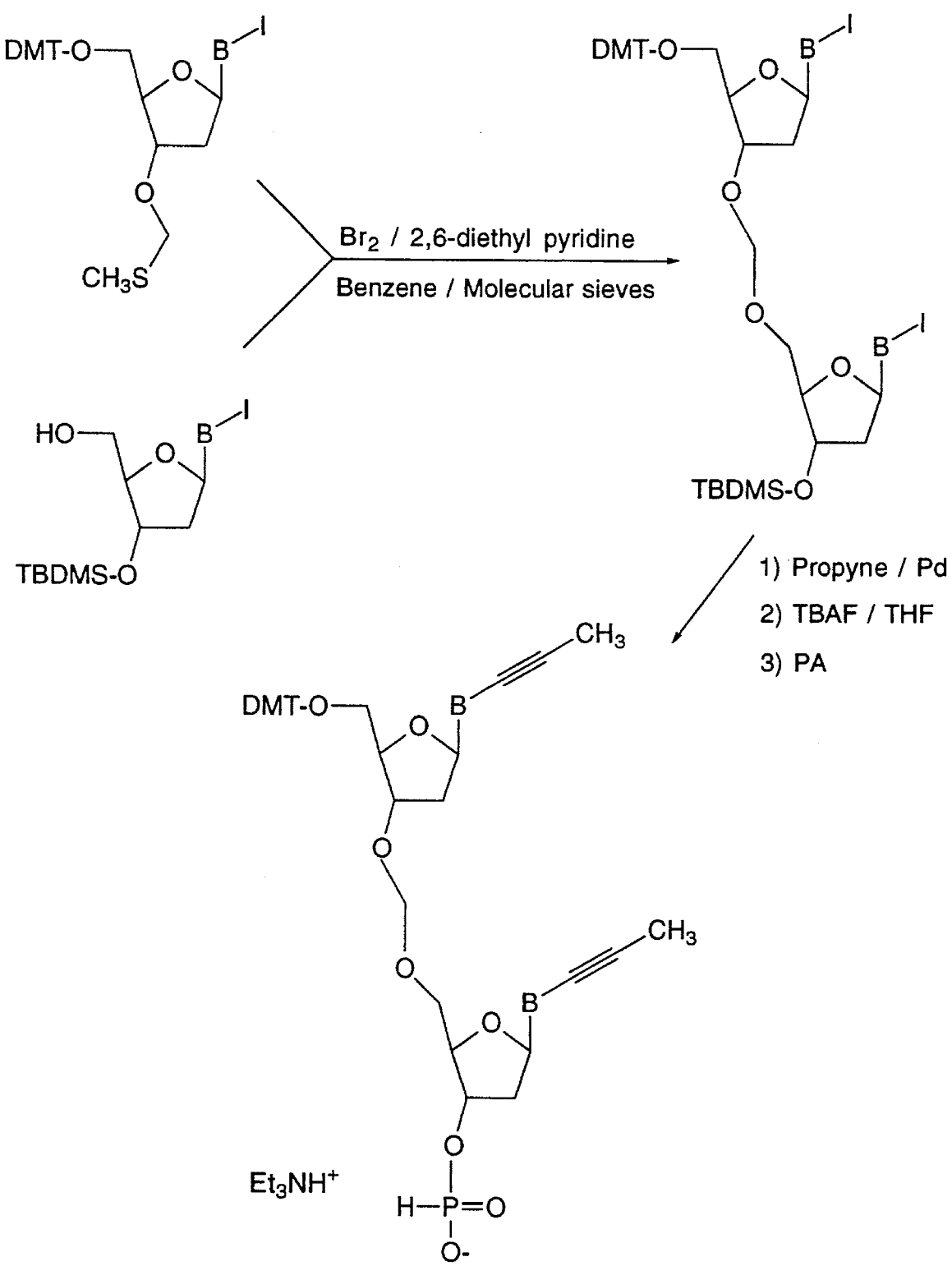
FIG. 11. Synthesis of dimer linked by a formacetal linkage (method #2).

The foregoing synthon is obtained by first preparing the 7-iodo deazapurine forms of B and then converting these to 7-propyne derivatives, for example, by treating the dimer synthon with propyne in the presence of palladium, CuI, triethylamine, and DMF. These synthons can be incorporated into an oligomer using standard synthesis techniques as shown in FIGS. 7, 8 and 11. Synthesis of formacetal and 3'-thioformacetal substitute linkages is described in disclosed in U.S. application Ser. No. 07/874,334, which disclosure is described in PCT/US92/03385. Trimer synthons containing formacetal, 3'-thioformacetal, riboacetal or other substitute linkages are also preferred compounds. Trimers and tetramers are preferred for synthesis of oligomers having enhanced permeation across cell membranes.

The synthesis of oligomers containing methylphosphonate and phosphodiester linkages is effected using art-known solid-phase oligomer synthesis techniques. A description of modifications useful in the synthesis of phosphorothioate linked oligomers are found, for example, in EP publication 288,163; wherein the oxidation step in solid phase automated synthesis using amidite chemistry can be independently adjusted at any step to obtain the phosphorothioate. An alternate method for synthesis of oligomers with phosphorothioate linkages, via hydrogen phosphonate chemistry, has also been described (Froehler, B., et al., *Nucleic Acid Res* (1986) 14:5399–5467; Froehler, B., *Tetrahedron Letters* (1986) 27:5575–5578). Sulfurization can be accomplished using reagents such as tetraethylthiuram disulfide, dibenzoyl tetrasulfide, thiophosphoric acid disulfide and the like, 3H-1, 2-benzodithiol-3-one 1,1-dioxide and the like as described (Vu, H. et al., *Tet Lett* (1991) 26:3005–3008; Rao, M. V., et al., *Tet Lett* (1992) 33:4839–4842; U.S. Pat. No. 5,151,510 issued Sep. 29, 1992; Iyer, R., et al., *J Org Chem* (1990) 55:4693–4699; Dahl, O. *Sulfur Reports* (1991) 11:167–192). These sulfurization reagents can be used with either phosphoramidite or hydrogen-phosphonate chemistries. Synthesis of phosphorothioate oligomers having controlled stereochemistry can be used to generate stereoregular invention oligomers as described (International Publication No. EP 0 506 242). The thionomethyl phosphonate is prepared with methylphosphonamidite followed by sulfurization as described (Roelen, H. P. C. F., et al., *Tet Lett* (1992) 33:2357–2360) or with the sulfurization reagents described above.

Covalent Bonding Moiety

Included in some of the oligomers of the invention is a moiety which is capable of effecting at least one covalent bond between the oligomer and the target sequence. Multiple covalent bonds can also be formed by providing a multiplicity of such moieties. The covalent bond is preferably to a base residue in the target strand, but can also be made with other portions of the target, including the sugar or phosphodiester. The reaction nature of the moiety which effects crosslinking determines the nature of the target in the duplex. Preferred crosslinking moieties include acylating and alkylating agents, and, in particular, those positioned relative to the sequence specificity-conferring portion so as to permit reaction with the target location in the strand.

The crosslinking moiety can conveniently be placed as an analogous pyrimidine or purine residue in the sequence of the oligomer. The placement can be at the 5'- and/or 3'-ends, the internal portions of the sequence, or combinations of the above. Placement at the termini to permit enhanced flexibility is preferred. Analogous moieties can also be attached to peptide backbones.

In one preferred embodiment of the invention, a switchback oligomer containing crosslinking moieties at either end can be used to bridge the strands of the duplex with at least two covalent bonds. In addition, oligomer sequences of inverted polarity can be arranged in tandem with a multiplicity of crosslinking moieties to strengthen the complex.

Exemplary of alkylating moieties that are useful in the invention include $N^4,N^4$-ethanocytosine and $N^6,N^6$-ethanoadenine.

It is clear that the base need not be a purine or pyrimidine; indeed the moiety to which the reactive function is attached need not be a base at all. Any means of attaching the reactive group is satisfactory so long as the positioning is correct.

Inverted Polarity

In their most general form, inverted polarity oligomers, that can incorporate one or more nucleomonomers described above, contain at least one segment along their length of the formula:

  (1)

or

  (2)

where —C— symbolizes any method of coupling the nucleomonomer sequences of opposite polarity (Froehler, B. C., et al., *Biochemistry* (1992) 31:1603–1609; Horne, D. A., et al., *J Am Chem Soc* (1990) 112:2435–2437; Beal, P. A., et al., *J Am Chem Soc* (1992) 114:4976–4978).

In these formulas, the symbol 3'————5' indicates a stretch of oligomer in which the linkages are consistently formed between the 5'-hydroxyl of the ribosyl residue of the nucleomonomer to the left with the 3'-(or 2'- for oligomers having 2', 5' linkages) hydroxyl of the ribosyl residue of the nucleomonomer to the right (i.e., a region of uniform polarity), thus leaving the 5'-hydroxyl of the rightmost nucleomonomer ribosyl residue free for additional conjugation. Analogously, 5'————3' indicates a stretch of oligomer in the opposite orientation wherein the linkages are formed between the 3'-hydroxyl of the ribosyl residue of the left nucleomonomer and the 5'-hydroxyl of the ribosyl residue of the nucleomonomer on the right, thus leaving the 3'-hydroxyl of the rightmost nucleomonomer ribosyl residue free for additional conjugation.

The linkage, symbolized by —C—, can be formed so as to link the 5'-hydroxyls of the adjacent ribosyl residues in formula (1) or the 3' hydroxyls of the adjacent ribosyl residues in formula (2), or the "—C—" linkage can conjugate other portions of the adjacent nucleomonomers so as to link the inverted polarity strands. "—C—" can represent a linker moiety, or simply a covalent bond.

It should be noted that if the linkage between strands of inverted polarity involves a sugar residue, either the 3'- or 2'-position can be involved in the linkage, and either of these positions can be in either R or S configuration. The choice of configuration will in part determine the geometry of the oligomer in the vicinity of the linkage. Thus, for example, if adjacent 3'-positions are used to effect a covalent linkage, less severe deformation of the oligomer chain will generally occur if both 3'-hydroxyls involved in the linkage are in the conventional R configuration. If they are both in the S configuration, this will result in a favorable "kink" in the chain.

The synthesis of oligomers having modified residues and/or inverted polarity can be accomplished utilizing standard solid phase synthesis methods.

In general, there are two commonly used solid phase-based approaches to the synthesis of oligomers containing conventional 3'→5' or 5'→3' linkages, one involving intermediate phosphoramidites and the other involving intermediate phosphonate linkages. In the phosphoramidite based synthesis, a suitably protected nucleomonomer having a cyanoethylphosphoramidite at the position to be coupled is reacted with the free hydroxyl of a growing nucleomonomer chain derivatized to a solid support. The reaction yields a cyanoethylphosphite, which linkage must be oxidized to the cyanoethylphosphate at each intermediate step, since the reduced form is unstable to acid. The H-phosphonate-based synthesis is conducted by the reaction of a suitably protected nucleomonomer containing an H-phosphonate moiety at a position to be coupled with a solid phase-derivatized nucleomonomer chain having a free hydroxyl group, in the presence of a suitable activator to obtain an H-phosphonate diester linkage, which is stable to acid. Thus, the oxidation to the phosphate or thiophosphate can be conducted at any point during the synthesis of the oligomer or after synthesis of the oligomer is complete. The H-phosphonates can also be converted to phosphoramidate derivatives by reaction with a primary or secondary amine in the presence of carbon tetrachloride. To indicate the two approaches generically, the incoming nucleomonomer is regarded as having a "coupling phosphite/phosphate" group.

Variations in the type of substitute linkage are achieved by, for example, using the methyl phosphonate precursors rather than the H-phosphonates per se, using thiol derivatives of the nucleomonomer moieties and generally by methods known in the art. Nonphosphorous based linkages can also be used, such as the formacetal 3'-thioformacetal, 3'-amino and 5'-ether type linkages described above.

A particularly preferred dimer synthon used to mediate the switchback in an oligomer is the O-xyloso linker. The O-xyloso linker consists of two xylose-nucleomonomers linked to each other by o-xylene at the 3'-position of each xylose sugar. The switchback linker synthon was synthesized using α,α'-orthodibromoxylene and 5'-DMT nucleomonomer to give a dimer. The dimer was converted to the H-phosphonate and was used in solid phase synthesis to generate oligomers. Linkers containing the bases thymine, 5-methylcytosine, 8-hydroxy-$N^6$-methyladenine, pseudoisocytosine, 5-propynyluracil or cytosine are synthesized as homodimers. However, the switchback linker dimers can also be synthesized as mixed heterodimers that are separated chromatographically.

2' Modified Oligomers

Included in some of the oligomers containing 7-substituted deazapurines of the invention are modifications of the ribose or deoxyribose sugar. 2'-O-methyl-, 2'-O-ethyl- and 2'-O-allyl oligomers have been synthesized and shown to bind to single-stranded complementary nucleic acid sequences (Cotten, M., et al., *Nucleic Acids Res* (1990) 19:2629–2635; Blencowe, B. J., et al., *Cell* (1989) 59:531–539; Sproat, B. S., et al., *Nucleic Acids Res* (1989) 17:3373–3386; Inoue, H., et al., *Nucleic Acids Res* (1987) 15:6131–6148; Morisawa, H., et al., European Patent Serial No. 0339842; Chavis, C., et al., *J Organic Chem* (1982) 47:202–206; Sproat, B. S., et al., *Nucleic Acids Res* (1991) 19:733–738; Sproat, B. S., et al., *Nucleic Acids Res* (1990) 18:41–49). The 2'-modified oligomers were reported to be relatively nuclease stable compared to unmodified controls. Synthesis of 2' fluoro nucleomonomers and their incorporation into oligomers has also been described (Codington, J. F., et al., *J Org Chem* (1964) 29:558–564; Fazakerley, G. V., et al., *FEBS Lett* (1985) 182:365–369; and Kawasaki, A. M., et al., *J. Med. Chem.* (1993) 36:831–841). Synthesis of oligomer analogs containing the modified bases described herein would be based on methods described. Synthesis of oligomers containing 2'-amino nucleomonomers has been described (Pieken, W. A., et al., *Science* (1991) 253:314–317).

Figures 1, 5:
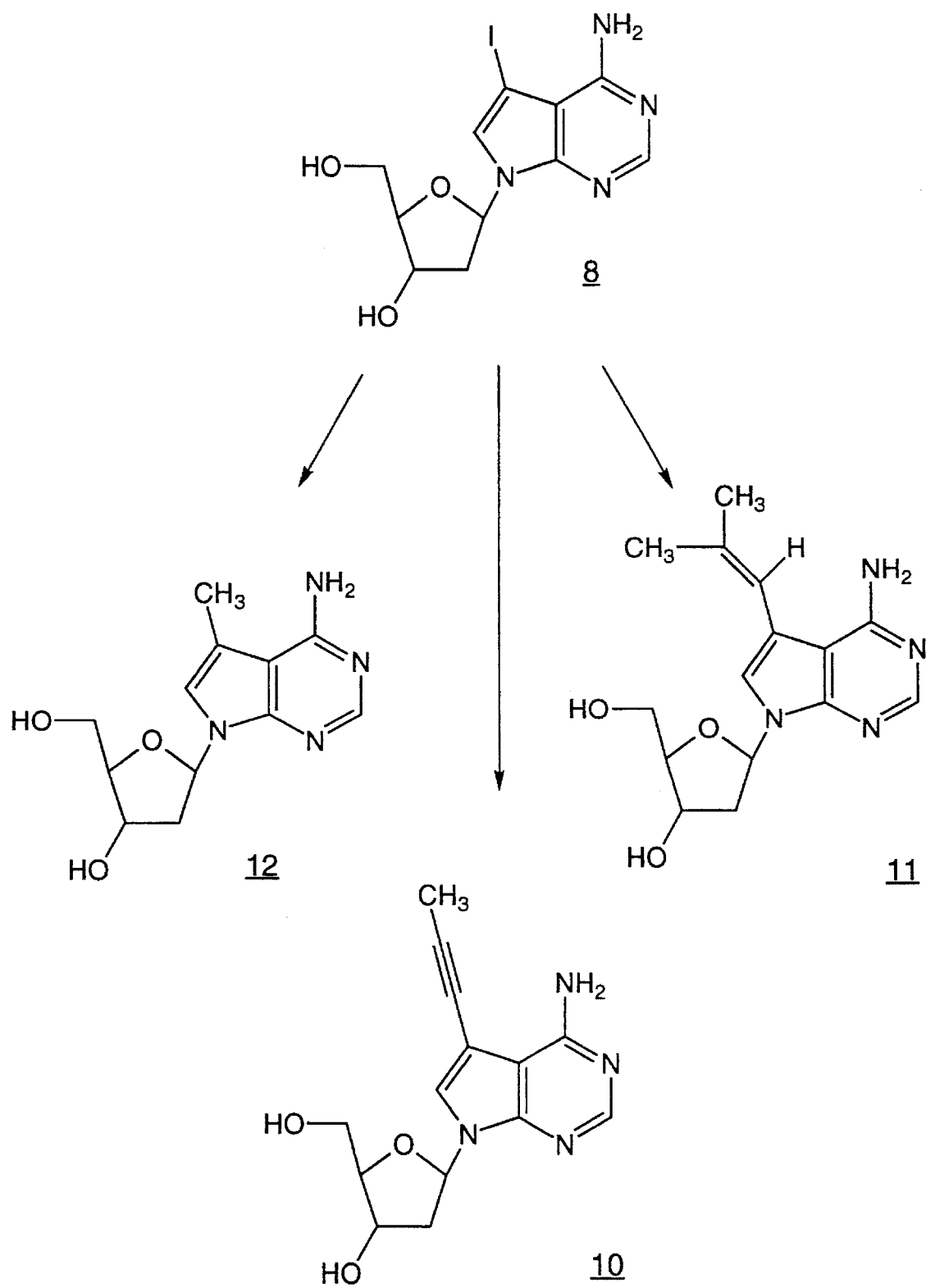
Figures 2, 5:
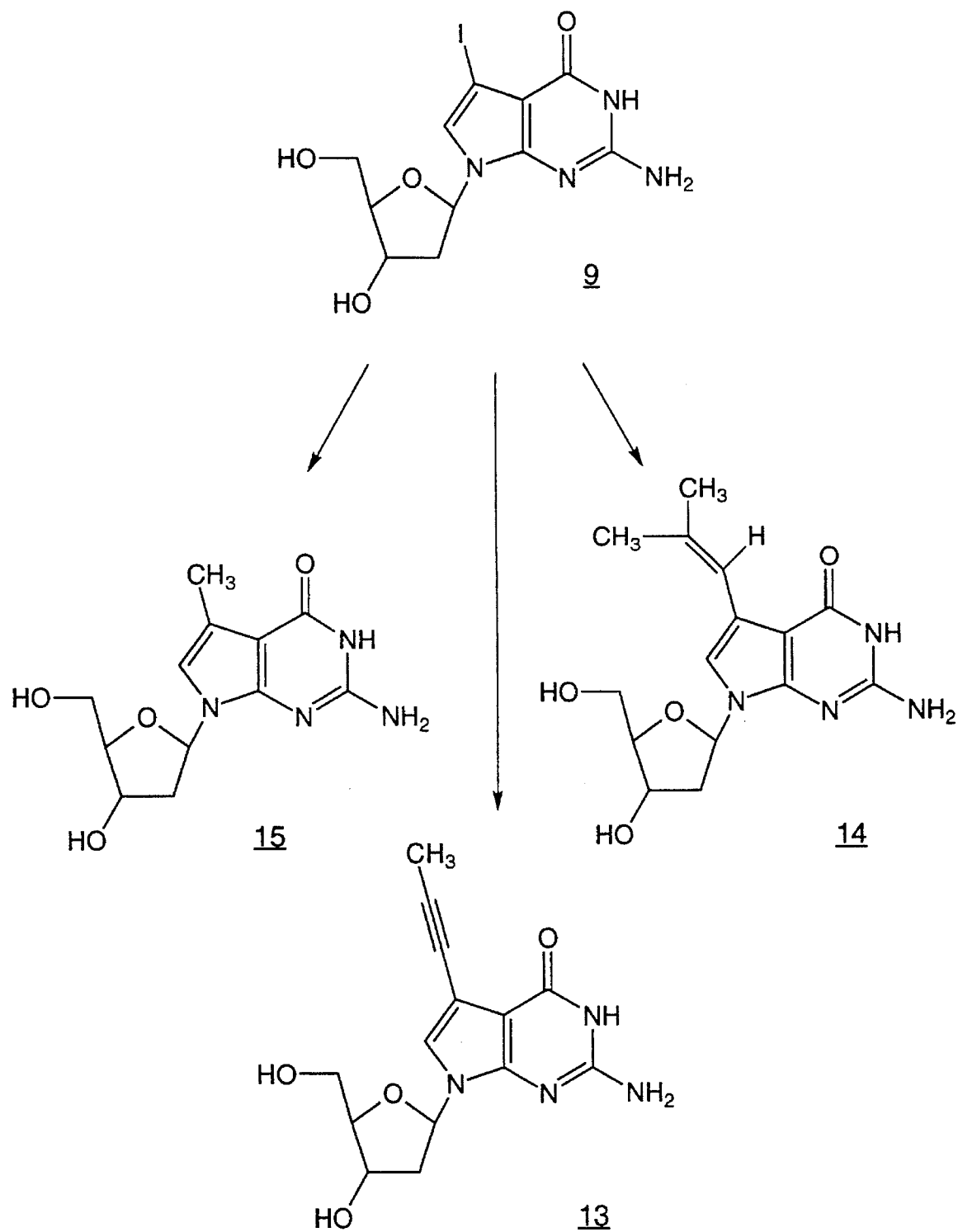

In an additional use of bases (1) and (2) in oligomers of the invention, 2'-O-allyl modified sugar forms of the nucleomonomers containing the 7-deazapurine bases (1) and (2) of the invention are included in the oligomer. Other 2'-O-allyl-substituted nucleomonomers can also be used at other positions in the oligomer (Froehler, B. C., et al., *Tetrahedron Letters* (1993) 34:1003–1006). The 2'-O-allyl nucleomonomers of the invention can be prepared using standard methods. Glycosylation of the 7-deazapurine heterocycles yields a suitably protected nucleomonomer (18) (Ramasamy, K., et al., *Tetrahedron Letters* (1987) 28:5107–5110). Standard synthetic techniques are therefore conveniently employed to prepare the 2'-O-allyl nucleomonomer (19) (FIG. 6) (Sproat, B. S., et al., *Nucleic Acids Res* (1991) 19:733–738; Sproat, B. S., et al., *Nucleic Acids Res* (1990) 18:41–49) which is subsequently deprotected. The desired $R^2$, $R^8$ and $R^9$ substituents are introduced as described herein (FIG. 4 and 5), and the nucleomonomer functionalized for oligonucleotide synthesis.

The nucleomonomers derivatized at the 2'-position can be incorporated into oligomers in the same manner as underivatized forms.

Dimer and Trimer Synthons for Oligomers Containing Substitute Linkages

Oligomers containing substitute linkages that link adjacent nucleomonomer analog residues are preferably synthesized using suitably blocked dimer synthons as a starting material. For dimers wherein one or both base residues are 7-substituted deazapurines or related analogs, synthesis of a formacetal or 3'-thioformacetal-linked dimer is accomplished as described herein. An exemplary dimer containing a formacetal linkage of formula (6) shown in FIG. 1, Y, X, B and $R^3$ are as defined herein.

FIGS. 7 and 8 show synthesis schemes for intermediates in oligomer synthesis. In both Figures, the structure B—I represents 7-iodo deazapurine heterocycle and B—≡—$CH_3$ represents 7-(1-propynyl)deazapurine. Synthesis of a 3'-thioformacetal dimer or a trimer can conveniently be accomplished. As shown in FIG. 7, a 7-iodo deazapurine nucleomonomer protected at the 3'-position by esterification is first reacted with paraformaldehyde in the presence of HCl to obtain the derivatized nucleomonomer containing the substituent ClCHO$_2$— at the 5'-position. The nucleomonomer can be esterified using, for example, a long-chain alkyl or aromatic acid, such a decyl, hexyl, benzoyl, or phenoxyacetyl. In this first step, the 3'-esterified nucleomonomer is treated with an excess of paraformaldehyde in an inert solvent at low temperature and anhydrous HCl is bubbled through the reaction mixture. The solution is conveniently dried and the solvent removed to obtain the intermediate.

The intermediate shown as the chloromethylether (ClCH$_2$O—) at the 5'-position of the nucleoside, is then dissolved in an inert solvent. A solution of a second nucleomonomer protected at the 5'-position, for example by DMT, and bearing an —SH substituent at the 3'-position along with a base, preferably diisopropylethylamine (DIPEA), in an inert solvent, is also prepared. The chloromethyl ether intermediate is added dropwise to this solution and the reaction mixture is stirred for several hours.

The reaction is washed with water, and the organic layer is separated and dried to obtain the dimerized product having the 3'-SCH$_2$O— 5' linkage and protected at the 5'- and 3'-positions, as above. The resulting dimer is deprotected at the 3'-position and then converted to the propyne derivative as shown and described in Example 6. Where the dimer is to be used in standard oligomer synthesis, it is converted to the hydrogen phosphonate using 2-chloro-4H-1,2,3-benzodioxaphosphorin-4-one (van Boom's reagent for phosphytylation (PA)). FIG. 8 shows the synthesis of a 3'-thioformacetal trimer.

Synthesis of Alkenyl, Ethynyl Heteroaryl and Heteroaryl Derivatized Bases

Synthesis of 7-alkenyl and 7-heteroaryl substituted deazapurines is accomplished by the palladium mediated reaction of a suitable 7-deazapurine nucleomonomer, such as 8 or 9, or blocked forms thereof, such as (16), (17), or (20), with the appropriate stannane. Synthesis of alkenylstannanes and heteroarylstannanes is conveniently accomplished (FIGS. 9 and 14) (Leusink, A. J. et al., *J. Organometal. Chem.* (1967) 9:285–294; Bailey, T. R. *Tetrahedron Letters* (1986) 27:4407–4410; Jutzi, P. et al., *J. Organometal. Chem.* (1983) 246:163–168; Molloy, K. C. et al., *J. Organometal. Chem.* (1989) 365:61–73; Saihi, M. L. and Pereyre, M. *Bull. Soc. Chim.* (1977) 1251–1255; and Eaborn, C. and Waters, J. A. *J. Chem. Soc.* (1962) 1131–1132). A 7-iodo-7-deazaadenosine nucleomonomer is reacted with 2-methyl-1-propenyl tributylstannane in the presence of palladium catalyst to effect carbon-carbon bond formation (FIG. 9). The reaction is conveniently carried out in DMF or $CH_3CN$ with $Pd^0$ or $Pd^{II}$ catalyst. The reaction is carried out from room temperature to 65° C. for 2–48 hr. (Crisp, G. T., *Synthetic Communications* (1989) 19:2117–2123). The 7-mercury derivative is useful in the synthesis of 7-alkenyl derivatives of the 7-deazapurines of the invention (Bergstrom, D. E., et al., *J. Org. Chem.* (1981) 46:1423–1431).

Ethynyl heteroaryl derivatives are prepared from ethynyltrimethylsilane and an appropriate heteroaryl as described (Austin, W. B., et al., *J Org. Chem* (1981) 46:2280–2286) (FIG. 14). The deprotected ethynyl is then introduced into the nucleomonomer by standard procedures, as described in Example 6.

Utility and Administration

As the oligomers of the invention are capable of significant single-stranded or double-stranded target nucleic acid binding activity to form duplexes, triplexes or other forms of stable association, these oligomers are useful in diagnosis of diseases that are associated with expression of one or more genes such as those associated with pathological conditions.

Delivery of oligomers of the invention into cells can be enhanced by any suitable method including calcium phosphate, DMSO, glycerol or dextran transfection, electroporation or by the use of cationic anionic and/or neutral lipid compositions or liposomes by methods described (International Publication Nos. WO 90/14074, WO 91/16024, WO 91/17424, U.S. Pat. No. 4,897,355). The oligomers can be introduced into cells by complexation with cationic lipids such as DOTMA (which may or may not form liposomes) which complex is then contacted with the cells. Suitable cationic lipids include but are not limited to N-(2,3-di(9-(Z)-octadecenyloxyl))-prop-1-yl-N,N,N-trimethylammonium (DOTMA) and its salts, 1-O-oleyl-2-O-oleyl-3-dimethylaminopropyl-β-hydroxyethylammonium and its salts and 1,2-bis(oleyloxy)-3-(trimethylammonio)propane and its salts.

Enhanced delivery of the invention oligomers can also be mediated by the use of (i) viruses such as Sendai virus (Bartzatt, R., *Biotechnol Appl Biochem* (1989) 11:133–135) or adenovirus (Wagner, E., et al., *Proc Natl Acad Sci* (1992) 89:6099–6013; (ii) polyamine or polycation conjugates using compounds such as polylysine, protamine or N1,N12-bis(ethyl)spermine (Wagner, E., et al., *Proc Natl Acad Sci* (1991) 88:4255–4259; Zenke, M., et al., *Proc Natl Acad Sci* (1990) 87:3655–3659; Chank, B. K., et al., *Biochem Biophys Res Commun* (1988) 157:264–270; U.S. Pat. No. 5,138,045); (iii) lipopolyamine complexes using compounds such as lipospermine (Behr, J.-P., et al., *Proc Natl Acad Sci* (1989) 86:6982–6986; Loeffler, J. P., et al., *J Neurochem* (1990) 54:1812–1815); (iv) anionic, neutral or pH sensitive lipids using compounds including anionic phospholipids such as phosphatidyl glycerol, cardiolipin, phosphatidic acid or phosphatidylethanolamine (Lee, K.-D., et al., *Biochim Biophys ACTA* (1992) 1103:185–197; Cheddar, G., et al., *Arch Biochem Biophys* (1992) 294:188–192; Yoshimura, T., et al., *Biochem Int* (1990) 20:697–706); (v) conjugates with compounds such as transferrin or biotin or (vi) conjugates with compounds such as serum proteins (including albumin or antibodies), glycoproteins or polymers (including polyethylene glycol) that enhance pharmacokinetic properties of oligomers in a subject. As used herein, transfection refers to any method that is suitable for enhanced delivery of oligomers into cells. Any reagent such as a lipid or any agent such as a virus that can be used in transfection protocols is collectively referred to herein as a "permeation enhancing agent". Delivery of the oligomers into cells can be via cotransfection with other nucleic acids such as (i) expressable DNA fragments encoding a protein(s) or a protein fragment or (ii) translatable RNAs that encode a protein(s) or a protein fragment.

The oligomers can thus be incorporated into any suitable formulation that enhances delivery of the oligomers into cells.

The invention oligomers can be conveniently used as reagents for research or production purposes where inhibition of gene expression is desired. There are currently very few reagents available that efficiently and specifically inhibit the expression of a target gene by any mechanism. Oligomers that have been previously reported to inhibit target gene expression frequently have nonspecific effects and/or do not reduce target gene expression to very low levels (less than about 40% of uninhibited levels).

Thus, the oligomers as described herein constitute a reagent that can be used in methods of inhibiting expression of a selected protein or proteins in cells wherein the proteins are encoded by DNA sequences and the proteins are translated from RNA sequences, comprising the steps of: introducing an oligomer of the invention into the cells; and permitting the oligomer to form a duplex with the DNA or RNA whereby expression of the protein or proteins is inhibited.

RNase H "competent" or RNase H "incompetent" oligomers can be easily designed using the substitute linkages of the invention. RNase H competent oligomers can comprise one or more RNase H competent domains comprised of linked RNase H competent nucleomonomers. Oligomers having modifications such as 2'-substitutions (2'-O-allyl and the like) or certain uncharged linkages (methylphosphonate, phosphoramidate and the like) are usually incompetent as a substrate that is recognized by and/or acted on by RNase H. RNase H competence can facilitate antisense oligomer function by degrading the target RNA in an RNA-oligomer duplex (Dagle, J. M., et al., *Nucl Acids Res* (1990) 18:4751–4757; Walder, J. A. et al., International Publication Number WO 89/05358). The enzyme cleaves RNA in RNA-DNA duplexes.

In order to retain RNase H competence, an oligomer requires a RNase H competent domain of three or more competent contiguous nucleomonomers located within it (Quartin, R. S., et al., *Nucl Acids Res* (1989) 17:7253–7262). Design of oligomers resistant to nuclease digestion will have terminal linkage, sugar and/or base modifications to effect nuclease resistance. Thus, the oligomers can be designed to have modified nucleomonomer residues at either or both the 5'- and/or 3'-ends, while having an internal RNase H competent domain.

Exemplary oligomers that retain RNase H competence would generally have uniform polarity and would comprise about 2 to about 12 nucleomonomers at the 5'-end and at the 3'-end which stabilize the oligomer to nuclease degradation and about three to about 26 nucleomonomers that function as a RNase H competent domain between the RNase H incompetent 3'- and 5'-ends. Variations on such an oligomer would include (1) a shorter RNase H competent domain comprising 1 or 2 RNase H competent linkages or substitute linkages, (2) a longer RNase H incompetent domain comprising up to 15, 20 or more substitute linkages or nucleomonomers, (3) a longer RNase H competent domain comprising up to 30, 40 or more linkages, (4) oligomers with only a single RNase H incompetent domain at the 3' end or at the 5' end, or (5) oligomers having more than one RNase H competent domain. RNase H competence also applies as a consideration to oligomers having one or more regions of inverted polarity, to circular oligomers and to other types of oligomers.

Oligomers containing substitute linkages of the invention can be conveniently circularized as described (International Publication No. WO 92/19732; Kool, E. T. *J Am Chem Soc* (1991) 113:6265–6266; Prakash, G., et al., *J Am Chem Soc* (1992) 114:3523–3527). Such oligomers are suitable for binding to single-stranded or double-stranded nucleic acid targets. Circular oligomers can be of various sizes. Such oligomers in a size range of about 22–50 nucleomonomers can be conveniently prepared. The circular oligomers can have from about three to about six nucleomonomer residues in the loop region that separate binding domains of the oligomer as described (Prakash, G. ibid). Oligomers can be enzymatically circularized through a terminal phosphate by ligase or by chemical means via linkage through the 5'- and 3'-terminal sugars and/or bases.

In addition, the oligomers of the invention can also be applied as diagnostic agents that function by direct displacement of one strand in a duplex nucleic acid. Displacement of a strand in a natural duplex such as chromosomal DNA or duplex viral DNA, RNA or hybrid DNA/RNA is possible for oligomers with a high binding affinity for their complementary target sequences. Therapeutic applications of oligomers by this method of use, referred to herein as D-looping or "D-loop therapy" has not previously been possible because the affinity of natural DNA or RNA for its complementary sequence is not great enough to efficiently displace a DNA or RNA strand in a duplex. Therapeutic efficacy of oligomers that function by D-looping would result from high affinity binding to a complementary sequence that results in modulation of the normal biological function associated with the nucleic acid target. Types of target nucleic acids (DNA or RNA) include but are not limited to (i) gene sequences including exons, introns, exon/intron junctions, promoter/enhancer regions and 5' or 3' untranslated regions, (ii) regions of nucleic acids that utilize secondary structure in order to function (e.g. the HIV TAR stem-loop element or tRNAs), (iii) nucleic acids that serve structural or other functions such as telomeres, centromeres or replication origins (virus, bacteria and the like) and (iv) any other duplex region. It is clear that oligomers can be synthesized with discrete functional domains wherein one region of an oligomer binds to a target by D-looping while an adjacent region binds a target molecule by say, forming a triple helix or binding as an aptamer to a protein. Alternatively, a D-looping oligomer can bind to each strand in a duplex by switching the strand to which the oligomer binds (i.e. by having one region of the oligomer that binds to one strand and another region that binds to the complementary strand).

The controlling elements that dictate the mode of binding (i.e. triple helix or D-loop) are the sequence of the oligomer and the inherent affinity built into the oligomer. Base recognition rules in Watson-Crick duplex binding differ from those in Hoogsteen controlled triplex binding. Because of this, the oligomer base sequence can be used to dictate the type of binding rules an oligomer will utilize.

D-loop structures are formed in nature by enzyme-mediated processes (Harris, L. D. et al., *J Biol Chem* (1987) 262: 9285–9292) or are associated with regions where DNA replication occurs (Jacobs, H. T. et al., *Nucl Acids Res* (1989) 17:8949–8966). D-loops that arise from the binding of oligomers can result from a one or two step process. Direct displacement of a target strand will give rise to a D-loop by a single binding event. However, D-looping can also occur by forming a triple helix which facilitates a strand displacement event leading to the D-loop.

Ribozymes containing substitute linkages of the invention can be designed in order to design species with altered characteristics. Ribozymes that cleave single stranded RNA or DNA (Robertson, D. L., et al., *Nature* (1990) 544:467–468) have been described. Secondary or tertiary structure necessary for ribozyme function can be affected by design of appropriate oligomer sequences. For example, ribozymes having nuclease stable targeting domains containing substitute bases of the invention can have higher affinity, while maintaining base pairing specificity, for target sequences. Because of the higher affinity and/or nuclease stability of the invention oligomers shorter recognition domains in a ribozyme (an advantage in manufacturing) can be designed which can lead to more favorable substrate turnover (an advantage in ribozyme function).

In addition the oligomers of the invention can be used as diagnostic reagents to detect the presence, absence or amount of the target nucleic acid sequences to which they specifically bind. The enhanced binding affinity of the invention oligomers is an advantage for their use as primers and probes. Diagnostic tests can be conducted by hybridization through either double or triple helix formation which is then detected by conventional means. For example, the oligomers can be labeled using radioactive (including $^3$H, $^{32}$P, $^{35}$S, $^{14}$C and $^{125}$I), fluorescent, or chromogenic labels and the presence of label bound to solid support detected. Alternatively, the presence of a double or triple helix can be detected by antibodies which specifically recognize these forms. Means for conducting assays using such oligomers as probes are generally known.

The use of oligomers containing the invention substitute linkages as diagnostic agents by triple helix formation is advantageous since triple helices form under mild conditions and the assays can thus be carried out without subjecting test specimens to harsh conditions. Diagnostic assays based on detection of RNA for identification of bacteria, fungi or protozoa sequences often require isolation of RNA from samples or organisms grown in the laboratory, which is laborious and time consuming, as RNA is extremely sensitive to ubiquitous nucleases.

The oligomer probes can also incorporate additional modifications such as modified sugars and/or substitute linkages that render the oligomer especially nuclease stable, and would thus be useful for assays conducted in the presence of cell or tissue extracts which normally contain nuclease activity. Oligomers containing terminal modifications often retain their capacity to bind to complementary sequences without loss of specificity (Uhlmann et al., *Chemical Reviews* (1990) 90:543–584). As set forth above, the invention probes can also contain linkers that permit specific binding to alternate DNA strands by incorporating a switchback linker that permits such binding (Froehler, B. C., et al., *Biochemistry* (1992) 31:1603–1609); Horne et al., *J Am Chem Soc* (1990) 112:2435–2437).

Incorporation of base analogs of the present invention into probes that also contain covalent crosslinking agents has the potential to increase sensitivity and reduce background in diagnostic or detection assays. In addition, the use of crosslinking agents will permit novel assay modifications such as (1) the use of the crosslink to increase probe discrimination, (2) incorporation of a denaturing wash step to reduce background and (3) carrying out hybridization and crosslinking at or near the melting temperature of the hybrid to reduce secondary structure in the target and to increase probe specificity. Modifications of hybridization conditions have been previously described (Gamper et al., *Nucleic Acids Res* (1986) 14:9943).

Oligomers of the invention are suitable for use in diagnostic assays that employ methods wherein either the oligomer or nucleic acid to be detected are covalently attached to a solid support as described (U.S. Pat. No. 4,775,619). The oligomers are also suitable for use in diagnostic assays that rely on polymerase chain reaction techniques to amplify target sequences according to described methods (European Patent Publication No. 0 393 744). Oligomers of the invention containing a 3' terminus that can serve as a primer are compatible with polymerases used in polymerase chain reaction methods such as the Taq or Vent™ (New England Biolabs) polymerase. Oligomers of the invention can thus be utilized as primers in PCR protocols.

The oligomers are useful as primers that are discrete sequences or as primers with a random sequence. Random sequence primers can be generally about 6, 7, or 8 nucleomonomers in length. Such primers can be used in various nucleic acid amplification protocols (PCR, ligase chain reaction, etc) or in cloning protocols. The substitute linkages of the invention generally do not interfere with the capacity of the oligomer to function as a primer. Oligomers of the invention having 2'-modifications at sites other than the 3' terminal residue, other modifications that render the oligomer RNase H incompetent or otherwise nuclease stable can be advantageously used as probes or primers for RNA or DNA sequences in cellular extracts or other solutions that contain nucleases. Thus, the oligomers can be used in protocols for amplifying nucleic acid in a sample by mixing the oligomer with a sample containing target nucleic acid, followed by hybridization of the oligomer with the target nucleic acid and amplifying the target nucleic acid by PCR, LCR or other suitable methods.

The oligomers derivatized to chelating agents such as EDTA, DTPA or analogs of 1,2-diaminocyclohexane acetic acid can be utilized in various in vitro diagnostic assays as described (U.S. Pat. Nos. 4,772,548, 4,707,440 and 4,707,352). Alternatively, oligomers of the invention can be derivatized with crosslinking agents such as 5-(3-iodoacetamidopropyn-1-yl)-2'-deoxyuridine or 5-(3-(4-bromobutyramido)propyn-1-yl)-2'-deoxyuridine and used in various assay methods or kits as described (International Publication No. WO 90/14353).

In addition to the foregoing uses, the ability of the oligomers to inhibit gene expression can be verified in in vitro systems by measuring the levels of expression in subject cells or in recombinant systems, by any suitable method (Graessmann, M., et al., *Nucleic Acids Res* (1991) 19:53–59).

All references cited herein are incorporated herein by reference in their entirety.

The following examples are intended to illustrate, but not to limit, the invention. Efforts have been made to insure accuracy with respect to numbers used (e.g., amounts, temperatures, etc.), but some experimental errors and deviations should be taken into account. Unless indicated otherwise, parts are parts by weight, temperature is in degrees Centigrade, and pressure is at or near atmospheric.

EXAMPLES

Example 1

Preparation of 7-deaza-2'-deoxyxanthosine

To a solution of 600 mg of 7-(2'-deoxy-β-D-erythro-pentofuranosyl)-2,4-dimethoxy- 7H-pyrrolo[2,3-d]pyrimidine in 20 mL of THF containing 1.2 g of sodium iodide was added 1.0 mL of trimethylsilyl chloride. The sealed reaction mixture was stirred for 20 hours at room temperature and then quenched with 50 mL of acetonitrile/water 9:1, and the resulting solution was chromatographed on a silica gel column using acetonitrile/water 9:1. The product-containing fraction was evaporated, and the residue was crystallized from water to yield 382 g of the title product.

Example 2

5'-dimethoxytrityl-7-deaza-2'-deoxyxanthosine-3'-H-phosphonate, triethylamine salt To a solution of 380 mg of 7-deaza-2'-deoxyxanthosine in 50 mL pyridine was added 950 mg of 4,4'-dimethoxytrityl chloride. The reaction was stirred for 0.5 h, then partitioned between water and ethyl acetate. The organic layer was washed with water and brine, then evaporated. The residue was chromatographed on a silica gel column using methylene chloride/methanol 9:1 to afford 520 mg of a crisp foam. This foam was dissolved in 25 mL of pyridine and the resulting solution was chilled to 0°. The cold solution was treated with 1.5 mL of a 1M solution of 2-chloro-4H-1,3, 2-benzodioxaphosphorin-4-one in methylene chloride. After 15 min, the solution was quenched with 40 mL of ice-cold triethyl ammonium bicarbonate buffer pH 7.5, and the mixture was extracted with methylene chloride. The organic extracts were evaporated and the residue was chromatographed on a silica gel column using acetonitrile/water 9:1 v:v (2% triethylamine) to afford 360 mg of the phosphonate.

Example 3

Preparation of Oligomers Containing 7-deaza-2'-deoxyguanosine

In a manner similar to that set forth in Example 2, 2'-deoxy-7-deazaguanosine was converted to the 5'-DMT-blocked 3'-H-phosphonate monomer incorporated into oligomers.

Example 4

Binding of Oligomers of the Invention to Target Sequences
The double-stranded HER-2 target sequence used was:

| | |
|---|---|
| 5' AGGAGAAGGAGGAGG 3' | (SEQ ID NO:1) |
| 3' TCCTCTTCCTCCTCC 5' | (SEQ ID NO:2) |

The GT oligomer sequence used was

| | |
|---|---|
| 5' GGTGGTGGTTGTGGTY 3' | (SEQ ID NO:3) |
| 5' GGXGGXGGXXGXGGXY 3' | (SEQ ID NO:4) |

Y is anthraquinone and was incorporated into oligomers as described (Lin, K. et al., *Nucleic Acids Res* (1991) 19:3111–3114). The anthraquinone moiety did not affect binding of the oligomer to duplex target DNA.

Both oligomers were footprinted, the GX oligomer footprinted at 1 µm; no binding was observed with the GT control oligomer. Triplex formation conditions were 20 mM MOPS, pH 7.2, 140 mM KCl, 1 mM spermine, and 1 mM $MgCl_2$. Thus, triplex formation was observed under physiological ion conditions due to the presence of 2'-deoxy-7-deazaxanthosine residues.

A G*T oligomer synthesized was

5' G*G*TG*G*TG*G*TTG*TG*G*T 3'    (SEQ ID NO:5)

Example 5

Testing Oligomers Containing Bases of the Invention for Binding to Single-Stranded RNA or DNA The following oligomers are prepared:

Target Sequence:

5' ATA TAT ATT ATT TTT 3'    (SEQ ID NO:6)

ON-1

5' XXX XAU AAU AUA UAU 3'    (SEQ ID NO:7)

ON-2

5' AAA AAU XAU AUA UAU 3'    (SEQ ID NO:8)

ON-3

5' AAA AAU AXU AUA UAU 3'    (SEQ ID NO:9)

ON-4

5' AAA AAU AAU XUA UAU 3'    (SEQ ID NO:10)

ON-5

5' AAA AAU AXU XUX UXU 3'    (SEQ ID NO:11)

ON-6

5' AAA AAU AAU AUA UAU 3'    (SEQ ID NO:12)

X=position of 7-substituted deazapurine nucleomonomer
A=2'-deoxyadenosine
U=T, 5-(1-propynyl)-2'-deoxyuridine (pdU), or other suitable pyrimidines
ODN-1 allows for the assessment of a 5' XXX context for binding to a target sequence, in which U=pdU or thymidine.
ODN-2 allows for the assessment of a 5' UX context, in which U=pdU or thymidine.
ODN-3 allows for the assessment of a 5' XU context, in which U=pdU or thymidine.
ODN-4 allows for the assessment of a 5' UXU context, in which U=pdU or thymidine.
ODN-5 allows for the assessment of an alternating context of pyrimidine/purine, in which U=pdU or thymidine.

Example 6

Preparation of 7-deaza-7-(1-propylyl)-2'-deoxyadenosine
In a 25 mL round bottom flask was placed:

a) 376 mg (1 mmole) 7-deaza-7-iodo-2'-deoxyadenosine;

b) 5 mL anhydrous DMF;

c) 38 mg (0.2 mmole) CuI;

d) 278 µL (2 mmole) $Et_3N$;

e) 115 mg (0.1 mmole) $(Ph_3P)_4Pd$;

f) and the solution saturated with propyne gas.

The reaction mixture was stirred overnight, at room temperature, and to this was added Dowex ion-exchange resin ($HCO_3^-$ form), 5 mL MeOH, 5 mL $CH_2Cl_2$, and stirring continued for 2 hr. The resin was filtered, washed with MeOH and evaporated to an oil. Silica gel chromatography yield 109 mg (0.38 mmole, 38%) of 13. See: Hobbs, *J. Org. Chem.* (1989) 54:3420–3422.

Example 7

Preparation of 5'-dimethoxytrityl-N6-di-n-butylformamidine-7-deaza-7-(1-propynyl)-2'-deoxyadenosine The nucleoside from Example 6 was dissolved into anhydrous DMF (5 mL) and to this was added di-n-butylformamide dimethyl acetal (400 µL). The reaction mixture was stirred at room temperature for 24 hr., evaporated and purified by silica gel chromatography. The nucleoside was evaporated from anhydrous pyridine (5 mL), taken-up in anhydrous pyridine (5 mL) and to this was added DMT-Cl (135 mg, 0.4 mmole). After 24 hr. MeOH (2 mL) was added, the reaction mixture evaporated to ~2 mL, diluted with $CH_2Cl_2$, washed with $NaHCO_3$, dried over $Na_2SO_4$ and evaporated. Silica gel chromatography yielded 180 mg (0.25 mmole, 66%) of product.

Example 8

Preparation of 2-methyl-1-propenyl tributylstannane

In a 500 mL 3-neck flask was placed magnesium (5.7 g, 240 mmole) and anhydrous THF (200 mL). A solution of 1-bromo-2-methyl propene (25 mL, 242 mmole) in anhydrous THF (60 mL) was added dropwise at reflux, the reaction mixture maintained at reflux for 10 hr., and cooled to room temperature. To the resulting suspension was added tributyl tin chloride (69 mL, 241 mmole) dropwise, and the reaction mixture heated at reflux for 18 hr. The mixture was cooled to room temperature, diluted with diethyl ether, filtered through celite, washed with 5% aq. $NH_4Cl$ (2×150 mL), $H_2O$ (2×150 mL), saturated NaCl (2×150 mL), dried over $Na_2SO_4$ and evaporated. Fractional distillation yielded 67.5 g (195 mmole, 82%) of 16 (b.p.=92°–96° C. @ 0.27 mmHg). The title compound is then incorporated into nucleomonomers as shown in FIG. 9.

The instant invention is shown and described herein in what is considered to be the most practical and preferred embodiments. It is recognized, however, that departures can be made therefrom which are within the scope of the invention, and that modifications will occur to those skilled in the art upon reading this disclosure.

We claim:

1. An oligomer comprising from 2 to 30 nucleomonomers wherein at least one of said nucleomonomers comprises a base having the formula (1) or (2):

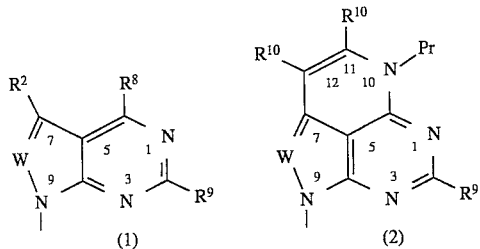

wherein

Pr is hydrogen or a monovalent or divalent protecting group;

W is N or CH;

$R^2$ is aryl, heteroaryl or 1-alkynylheteroaryl;

$R^8$ is OH, SH, NPr, NHPr or $NH_2$;

$R^9$ is H, OH, SH, NPr, NHPr or $NH_2$;

$R^{10}$ is independently H, OH, CN, F, Cl, Br, I, alkyl (C1–12), alkenyl (C2–12), alkynyl (C2–12), aryl (C6–9), heteroaryl (C4–9), or both $R^{10}$, taken together with the carbon atoms to which they are linked at positions 11 and 12, form (a) a 5 or 6 membered carbocyclic ring or, (b) a 5 or 6 membered heterocyclic ring comprising 1–3 N, O or S ring atoms, provided that no 2 adjacent ring atoms are O—O, S—S, O—S or S—O, and wherein any unsaturated C atom of the carbocyclic or heterocyclic ring is substituted by $R^{11}$ and any saturated carbons contain 2 $R^{11}$ substituents, wherein;

$R^{11}$ is independently H, alkyl (C1–4), alkenyl (C2–4), alkynyl (C2–4), $OR^{12}$, $SR^{12}$, or $N(R^{12})_2$ or halogen provided that there are no more than four halogens per 5 or 6 member ring;

$R^{12}$ is independently H, or alkyl (C1–4);

and salts thereof.

2. The oligomer of claim 1 wherein at least one base has the formula (2) and $R^{10}$ at position 11 is H and $R^{10}$ at position 12 is methyl, $R^{10}$ at position 12 is H or $R^{10}$ at position 11 is methyl, or $R^{10}$ at position 11 is H and $R^{10}$ at position 12 is 1-propynyl.

3. The oligomer of claim 1 wherein adjacent nucleomonomers are linked by linkages or substitute linkages and the oligomer contains at least one substitute linkage.

4. The oligomer of claim 3 wherein the substitute linkage is selected from the group consisting of phosphoramidate, phosphorothioate, methylphosphonate, riboacetal, 3'-N-methylhydroxylamine, thionomethylphosphonate, phosphorodithioate, 2'-thioformacetal, formacetal, and 3'-thioformacetal.

5. The oligomer of claim 4 wherein the substitute linkage is a phosphorothioate, formacetal or 3'-thioformacetal linkage.

6. The oligomer of claim 1 wherein at least one base has the formula (1) and $R^2$ is phenyl, 2-s-triazinyl, 2-, 3- or 4-pyridyl, 2-, 4- or 5-pyrimidinyl, 2- or 3-thienyl, 2-, 4- or 5-thiazolyl, 2- or 4-imidazolyl, 2-, 4- or 5-oxazoyl, 2- or 3-furanyl, 2- or 3-pyrrolyl, phenyl-ethynyl, 2-, 3- or 4-pyridine-ethyl, 2-, 4- or 5-pyrimidine-ethynyl, 2-, or 3-thiophene-ethynyl, 2-, 4- or 5-thiazole-ethynyl, 2- or 4-imidazole-ethynyl, s-triazine-ethynyl, 2- or 3-furan-ethynyl, 2-, 4- or 5-oxazole-ethynyl or 2- or 3-pyrrol-ethynyl.

7. The oligomer of claim 1 having from 8 to 30 nucleomonomers and uniform polarity.

8. The oligomer of claim 7 having 2 to 12 substitute linkages or nucleomonomers at the 5'-end and at the 3'-end which comprise nuclease stable domains, and 3 to 26 substitute linkages or nucleomonomers which comprise at least one RNase H competent domain consisting of 3 or more contiguous substitute linkages selected from the group consisting of phosphorothioate and phosphorodithioate linkages disposed between the nuclease stable domains.

9. The oligomer of claim 1 comprising 2, 3, 4, 5 or 6 nucleomonomers.

10. A method of synthesizing the oligomer of claim 1, comprising the steps of:

synthesizing a protected nucleomonomer synthon having a protecting group and a base and further having a coupling group capable of coupling to a nucleomonomer or oligomer;

coupling the nucleomonomer synthon to an acceptor nucleomonomer or oligomer;

removing the protecting group; and repeating the cycle until said oligomer is synthesized.

11. The method of claim 10 wherein the coupling group is a phosphoramidite or a hydrogen phosphonate coupling group.

12. The oligomer of claim 1 wherein at least one base has the formula (2) and both $R^{10}$ are taken together with the carbon atoms to which they are linked at positions 11 and 12 to form a 6-membered ring, said base having the formula (23) or (25)

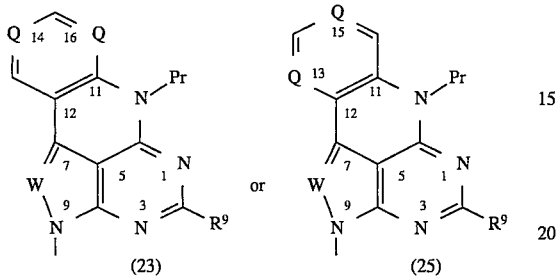

wherein each Q is independently N or $CR^{11}$.

13. The oligomer of claim 12 wherein adjacent nucleomonomers are linked by linkages or substitute linkages and at least one nucleomonomer linkage is a substitute linkage.

14. The oligomer of claim 12 wherein adjacent nucleomonomers are linked by linkages or substitute linkages and at least one nucleomonomer linkage is a phosphorothioate linkage.

15. The oligomer of claim 12 wherein adjacent nucleomonomers are linked by substitute linkages and all nucleomonomer substitute linkages are phosphorothioate linkages.

16. The oligomer of claim 13 wherein the substitute linkage is selected from the group consisting of phosphoramidite, phosphorothioate, methylphosphonate, riboacetal, 3'-N-methylhydroxylamine, thionomethylphosphonate, phosphorodithioate, 2'-thioformacetal, formacetal, and 3'-thioformacetal.

17. The oligomer of claim 12 complexed with a cationic lipid.

18. The oligomer of claim 12 having from 8 to 30 nucleomonomers and uniform polarity.

19. The oligomer of claim 18 having 2 to 12 substitute linkages or nucleomonomers at the 5'-end and at the 3'-end which comprise nuclease stable domains, and 3 to 26 substitute linkages or nucleomonomers which comprise at least one RNase H competent domain consisting of 3 or more contiguous substitute linkages selected from the group consisting of phosphorothioate and phosphorodithioate linkages disposed between the nuclease stable domains.

20. An oligomer of the formula (5);

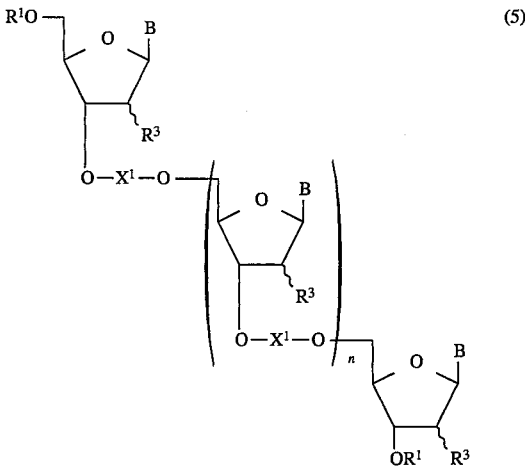

wherein
each $R^1$ is independently H, $PO_3^{-2}$, or a blocking group;
each $R^3$ is independently selected from the group consisting of H, OH, F, $NH_2$, $OCH_3$, $OC_2H_5$, $OC_3H_7$, $SCH_3$, $SC_2H_5$, $SC_3H_7$, $OC_3H_5$, and $SC_3H_5$;
each $X^1$ is independently selected from the group consisting of —P(S)(O)—, —P(S)(S)—, —P(O)(O)—, —P($CH_3$)(O)— and —P($CH_3$)(S)—;
n is an integer from 0 to 98; and
B is a base, provided that at least one B is of formula (1) or (2):

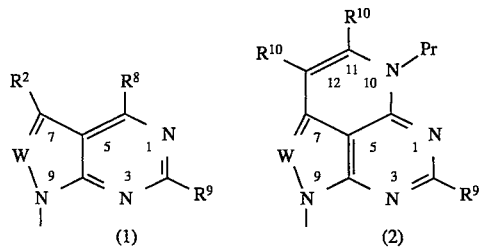

wherein
Pr is H or a monovalent or divalent protecting group;
W is N or CH;
$R^2$ is aryl, heteroaryl or 1-alkynylheteroaryl;
$R^8$ is OH, SH, a NPr or $NH_2$;
$R^9$ is H, OH, SH, NPr, NHPr or $NH_2$;
$R^{10}$ is independently H, OH, CN, halogen (F, Cl, Br, I), alkyl (C1–12), alkenyl (C2–12), alkynyl (C2–12), aryl (C6–9), heteroaryl (C4–9), or both $R^{10}$, taken together with the carbon atoms to which they are linked at positions 11 and 12, form
(a) a 5 or 6 membered carbocyclic ring or,
(b) a 5 or 6 membered heterocyclic ring comprising 1–3 N, O or S ring atoms, provided that no 2 adjacent ring atoms are O—O, S—S, O—S or S—O,
and wherein any unsaturated C atom of the carbocyclic or heterocyclic ring is substituted by $R^{11}$ and any saturated carbons contain 2 $R^{11}$ substituents, wherein;

49

$R^{11}$ is independently H, alkyl (C1–4), alkenyl (C2–4), alkynyl (C2–4), $OR^{12}$, $SR^{12}$, or $N(R^{12})_2$ or halogen provided that there are no more than four halogens per 5 or 6 member ring; and $R^{12}$ is independently H, or alkyl (C1–4).

21. The oligomer of claim 20 wherein at least one $R^1$ is H, $PO_3^{-2}$, DMT, MMT, H-phosphonate, methyl phosphoramidite, methylphosphoramidite, β-cyanoethylphosphoramidite or alkylphosphoramidite.

22. The oligomer of claim 20 wherein each $R^3$ is independently H, OH, F or O-allyl.

23. The oligomer of claim 20 wherein at least one $R^3$ is O-methyl, O-ethyl or O-propyl.

24. The oligomer of claim 20 wherein at least one base has the formula (2) and $R^{10}$ at position 11 is H and $R^{10}$ at position 12 is methyl, $R^{10}$ at position 12 is H or $R^{10}$ at position 11 is methyl, or $R^{10}$ at position 11 is H and $R^{10}$ at position 12 is 1-propynyl.

25. The oligomer of claim 20 wherein at least one base has the formula (2) and both $R^{10}$ are taken together with the carbon atoms to which they are linked at positions 11 and 12 to form a 6-membered ring, said base having the formula (23) or (25)

wherein each Q is independently N or $CR^{11}$.

26. The oligomer of claim 20 having a covalent link between the 5'-nucleomonomer and the 3' nucleomonomer whereby a circular oligomer is formed.

27. The oligomer of claim 20 conjugated to a solid support or label.

28. The oligomer of claim 20 which is a dimer, trimer, tetramer, pentamer or hexamer.

29. The oligomer of claim 20 complexed with a cationic lipid.

30. A method of synthesizing the oligomer of claim 20, comprising the steps of:

synthesizing a protected nucleomonomer synthon having a protecting group and a base and further having a coupling group capable of coupling to a nucleomonomer or oligomer;

coupling the nucleomonomer synthon to an acceptor nucleomonomer or oligomer;

removing the protecting group; and repeating the cycle until said oligomer is synthesized.

31. The method of claim 30 wherein the coupling group is a phosphoramidite or a hydrogen phosphonate coupling group.

32. A nucleomonomer having the structural formula (3) or (4):

50 wherein each $R^1$ is independently H or a blocking group;

$R^2$ is aryl, heteroaryl or 1-alkynylheteroaryl;

$R^3$ is selected from the group consisting of H, OH, F, $NH_2$, $OCH_3$, $OC_2H_5$, $OC_3H_7$, $SCH_3$, $SC_2H_5$, $SC_3H_7$, $OC_3H_5$, and $SC_3H_5$;

$R^8$ is OH, SH, NPr, NHPr or $NH_2$;

$R^9$ is H, OH, SH, NPr, NHPr or $NH_2$;

$R^{10}$ is independently H, OH, CN, halogen (F, Cl, Br, I), alkyl (C1–2), alkenyl (C2–12), alkynyl (C2–12), aryl (C6–9), heteroaryl (C4–9), or both $R^{10}$, taken together with the carbon atoms to which they are linked at positions 11 and 12, form
 (a) a 5 or 6 membered carbocyclic ring or,
 (b) a 5 or 6 membered heterocyclic ring comprising 1–3 N, O or S ring atoms, provided that no 2 adjacent ring atoms are O—O, S—S, O—S or S—O,
 and wherein any unsaturated C atom of the carbocyclic or heterocyclic ring is substituted by $R^{11}$ and any saturated carbons contain 2 $R^{11}$ substituents, wherein;

$R^{11}$ is independently H, alkyl (C1–4), alkenyl (C2–4), alkynyl (C2–4), $OR^{12}$, $SR^{12}$, or $N(R^{12})_2$ or halogen provided that there are no more than four halogens per 5 or 6 member ring;

$R^{12}$ is independently H, or alkyl (C1–4);

W is CH or N; and

Pr is H or a monovalent or divalent protecting group.

33. The nucleomonomer of claim 32 wherein $R^3$ is hydrogen, hydroxy fluorine, O-methyl or O-allyl.

34. The nucleomonomer of claim 32 wherein $R^1$ is a blocking group selected from the group consisting of DMT, MMT, FMOC, phenoxyacetyl, a silyl ether, hydrogen phosphonate, methylphosphonamidite, methylphosphoramidite and β-cyanoethylphosphoramidite.

35. The nucleomonomer of claim 32 wherein $R^1$ at the 3' position is selected from the group consisting of hydrogen phosphonate, N,N-diisopropylamino-β-cyanoethoxyphosphine, N,N-diisopropyl-aminomethoxyphosphine, N,N-diethylamino-β-cyanoethoxyphosphine, N,N-morpholino-β-cyanoethoxyphosphine, N,N-morpholino-methoxyphosphine, N,N-diisopropylaminomethylphosphonamidite, N,N-diethylaminomethylphosphonamidite, bis-morpholino-phosphine, N,N-dimethylamino-β-cyanoethyl-mercaptophosphine, 2-chlorophenyl phosphate, 4-chlorophenyl phosphate, 2,4-dichlorophenyl phosphate, 2,4-dibromophenyl phosphate, 2-chlorophenyl thiophosphate, 4-chlorophenyl thiophosphate, 2,4-dichlorophenyl thiophosphate, and 2,4-dibromophenyl thiophosphate.

36. The nucleomonomer of claim 32 having a structure of formula (4) wherein each $R^{10}$ is independently H, OH, CN, halogen, alkyl (C1–9), 1-alkenyl (C2–8), 1-alkynyl (C2–8), aryl (C6–7), or heteroaryl (C4–6).

37. The nucleomonomer of claim 32 of the formula:

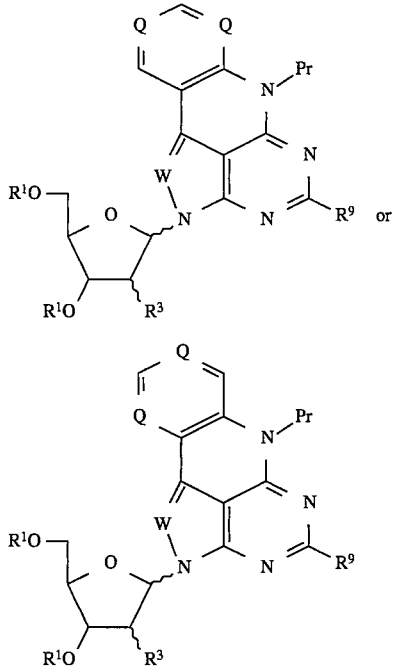

wherein Q is independently N or $CR^{11}$.

38. The nucleomonomer of claim 37 wherein $R^3$ is hydrogen, hydroxy fluorine, or O-allyl.

39. The nucleomonomer of claim 37 wherein both $R^1$ are hydrogen and $R^3$ is hydroxy.

40. The nucleomonomer of claim 38 wherein both $R^1$ are hydrogen and $R^3$ is hydroxy.

41. The nucleomonomer of claim 37 wherein $R^1$ is a blocking group selected from the group consisting of DMT, MMT, FMOC, phenoxyacetyl, a silyl ether, hydrogen phosphonate, methylphosphonamidite, methylphosphoramidite and β-cyanoethylphosphoramidite.

42. The nucleomonomer of claim 37 wherein $R^1$ at the 3' position is selected from the group consisting of hydrogen phosphonate, N,N-diisopropylamino-β-cyanoethoxyphosphine, N,N-diisopropyl-aminomethoxyphosphine, N,N-diethylamino-β-cyanoethoxyphosphine, N,N-morpholino-β-cyanoethoxyphosphine, N,N-morpholino-methoxyphosphine, N,N-diisopropylaminomethyl-phosphonamidite, N,N-diethylamino-methylphosphonamidite, bis-morpholino-phosphine, N,N-dimethylamino-β-cyanoethyl-mercaptophosphine, 2-chlorophenyl phosphate, 4-chlorophenyl phosphate, 2,4-dichlorophenyl phosphate, 2,4-dibromophenyl phosphate, 2-chlorophenyl thiophosphate, 4-chlorophenyl thiophosphate, 2,4-dichlorophenyl thiophosphate, and 2,4-dibromophenyl thiophosphate.

43. The nucleomonomer of claim 37 wherein both $R^1$ are hydrogen and $R^3$ is hydrogen.

44. The nucleomonomer of claim 32 wherein both $R^1$ are hydrogen and $R^3$ is hydrogen.

45. An oligomer comprising from 2 to 30 nucleomonomers wherein at least one of said nucleomonomers comprises a base having the formula:

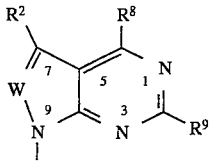

wherein

Pr is H or a monovalent or divalent protecting group;

$R^2$ is 1-propynyl;

$R^8$ is OH, SH, NPr, NHPr or $NH_2$;

$R^9$ is H, OH, SH, NPr, NHPr or $NH_2$; and

W is N or CH and salts thereof.

46. The oligomer of claim 45 wherein adjacent nucleomonomers are linked by linkages or substitute linkages and the oligomer contains at least one substitute linkage.

47. The oligomer of claim 45 having from 8 to 30 nucleomonomers and uniform polarity.

48. The oligomer of claim 45 wherein the substitute linkage is selected from the group consisting of phosphoramidate, phosphorothioate, methylphosphonate, riboacetal, 3'-N-methylhydroxylamine, thionomethylphosphonate, phosphorodithioate, 2'-thioformacetal, formacetal, and 3'-thioformacetal.

49. The oligomer of claim 48 wherein the substitute linkage is selected from the group consisting of phosphorothioate and formacetal.

50. The oligomer of claim 45 wherein $R^8$ is OH and $R^9$ is $NH_2$ or NHPr.

51. The oligomer of claim 45 complexed with a cationic lipid.

52. An oligomer of the formula (5):

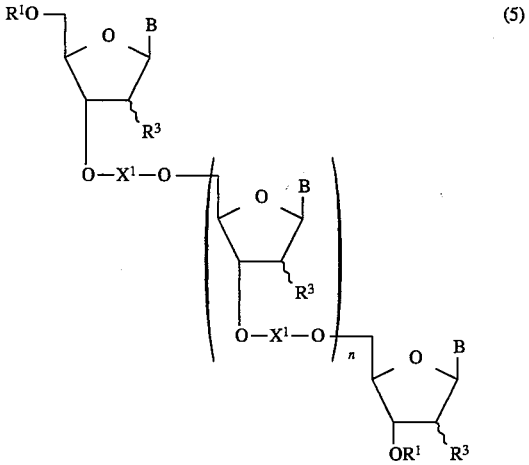

wherein each $R^1$ is independently H, $PO_3^{-2}$, or a blocking group;

each $R^3$ is independently selected from the group consisting of H, OH, F, $NH_2$, $OCH_3$, $OC_2H_5$, $OC_3H_7$, $SCH_3$, $SC_2H_5$, $SC_3H_7$, $OC_3H_5$, and $SC_3H_5$;

each $X^1$ is independently selected from the group consisting of —P(S)(O)—, —P(S)(S)—, —P(O)(O)—, —P(CH_3)(O)— and —P(CH_3)(S)—;

n is an integer from 0 to 98; and

B is a base, provided that at least one B is of formula:

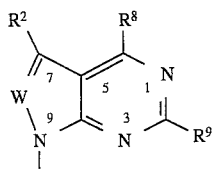

wherein $R^2$ is 1-propynyl;

$R^8$ is OH or SH;

$R^9$ is NPr, NHPr or $NH_2$;

Pr is H or a monovalent or divalent protecting group; and

W is N or CH.

53. The oligomer of claim 52 wherein at least one $R^1$ is H, $PO_3^{-2}$, DMT, MMT, H-phosphonate, methyl phosphonamidite, methylphosphoramidite, β-cyanoethylphosphoramidite or alkylphosphoramidite.

54. The oligomer of claim 53 wherein each $X^1$ is —P(S)(O)—.

55. The oligomer of claim 54 complexed with a cationic lipid.

56. The oligomer of claim 52 wherein each $R^3$ is independently H, OH, F or O-allyl.

57. The oligomer of claim 52 wherein at least one $R^3$ is O-methyl, O-ethyl or O-propyl.

58. The oligomer of claim 52 complexed with a cationic lipid.

* * * * *